US010568963B2

(12) United States Patent
Pandey et al.

(10) Patent No.: US 10,568,963 B2
(45) Date of Patent: *Feb. 25, 2020

(54) MULTIFUNCTIONAL NANOPLATFORMS FOR FLUORESCENCE IMAGING AND PHOTODYNAMIC THERAPY DEVELOPED BY POST-LOADING PHOTOSENSITIZER AND FLUOROPHORE TO POLYACRYLAMIDE NANOPARTICLES

(75) Inventors: Ravindra K. Pandey, East Amherst, NY (US); Raoul Kopelman, Ann Arbor, MI (US); Anurag Gupta, Hamburg, NY (US); Munawwar Sajjad, Clarence Center, NY (US)

(73) Assignees: HEALTH RESEARCH, INC., Buffalo, NY (US); HE RESEARCH FOUNDATION OF STATE UNIVERSITY OF NEW YORK, Amherst, NY (US); REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/566,411

(22) Filed: Aug. 3, 2012

(65) Prior Publication Data
US 2013/0202525 A1    Aug. 8, 2013

Related U.S. Application Data

(63) Continuation-in-part of application No. 12/909,573, filed on Oct. 21, 2010, now Pat. No. 8,562,944.

(60) Provisional application No. 61/279,522, filed on Oct. 21, 2009.

(51) Int. Cl.
| | |
|---|---|
| *A61K 41/00* | (2006.01) |
| *A61K 49/00* | (2006.01) |
| *B82Y 15/00* | (2011.01) |
| *A61K 51/04* | (2006.01) |
| *A61K 51/12* | (2006.01) |
| *A61K 47/69* | (2017.01) |

(52) U.S. Cl.
CPC ...... *A61K 41/0057* (2013.01); *A61K 41/0071* (2013.01); *A61K 47/6933* (2017.08); *A61K 49/0002* (2013.01); *A61K 49/0032* (2013.01); *A61K 49/0052* (2013.01); *A61K 49/0093* (2013.01); *A61K 51/0451* (2013.01); *A61K 51/1244* (2013.01); *B82Y 15/00* (2013.01)

(58) Field of Classification Search
CPC ........... A61K 41/0071; A61K 49/0017; A61K 41/0057; A61K 47/6933; A61K 51/1244; A61K 49/0093; A61K 49/0052; A61K 49/0032; A61K 49/0002; A61K 51/0451; B82Y 15/00
See application file for complete search history.

(56) References Cited

U.S. PATENT DOCUMENTS

| | | | |
|---|---|---|---|
| 2005/0196343 | A1 | 9/2005 | Reddy et al. |
| 2009/0043090 | A1* | 2/2009 | Pandey et al. ............... 540/135 |
| 2011/0022129 | A1 | 1/2011 | Prudhomme et al. |
| 2011/0091373 | A1 | 4/2011 | Pandey et al. |

FOREIGN PATENT DOCUMENTS

| | | | | |
|---|---|---|---|---|
| WO | WO2009105209 | * | 8/2009 | ........... A61K 31/695 |
| WO | WO2009105209 A1 | | 8/2009 | |

OTHER PUBLICATIONS

Huang (Rev. Prog. Clin. PDT, Technol. Cancer. Res. Treat. 2005, p. 283.*
Photos. Clin. PDT, Photodia. Photodyna. Thera. 2004, p. 27-42.*
Kopelman, Raoul, et al. "Multifunctional Nanoparticle Platforms for in Vivo MRI Enhancement and Photodynamic Therapy of a Rat Brain Cancer", Journal of Magnetism and Magnetic Materials 293, pp. 404-410, Copyright 2005.
Daubresse, Catherine, et al., "Enzyme Immobilization in Nanoparticles Produced by Inverse Microemulsion Polymerization", Journal of Colloid and Interface Science 168, pp. 222-229, Copyright 1994.
Ross, B. et al. "Photonic and magnetic nonexplorers for biomedicaluse: from subcellar imaging to cancer diagnostics and therapy", University of Michigan, Ann arbor, MI 48109; Molecular Therapeutics, Inc., Ann Arbor, MI 48109; Text Center for Molecular Imaging Research, Massachusetts General Hospital, Charlestown, MA 02129.
Reddy, G.R. et al., "Vascular targeted nonoparticles for imaging and treatment of brain tumors", Clinical Cancer Research Nov. 15, 2006 US LNKD-DOI:10.1158/1078-0432.CCR-06-0946, vol. 12, No. 22, Nov. 15, 2006, pp. 6677-6686, XP002643835.
Koo, Photonic explorers based on multifunctional nanoplatforms for biosensing and photodynamic therapy, Applied Optics, 46/10, pp. 1924-1930, 2007.
Gupta et al., "Multifunctional ORMOSIL and PAA Nanoparticles", Photodynamic Therapy: Back To the Future, Edited by Kessel, David H., Proceedings of the SPIE, vol. 7380 (2009), pp. 73805H-73805H-12 (2009).
Shouyan Wang, et al. "Novel Methods to Incorporate Photosensitizers into Nanocarriers for Cancer Treatment by Photodynamic Therapy"; Lasers in Surgery and Medicine 43:686-695 (2011);Department of Medicine, University of Michigan, Ann Arbor Michigan, 48109; PDT Center and Department of Dermatology; Roswell Park Cancer Institute; Buffalo, New York, 14263.

* cited by examiner

*Primary Examiner* — Matthew P Coughlin
*Assistant Examiner* — Thurman Wheeler
(74) *Attorney, Agent, or Firm* — Michael L. Dunn

(57) ABSTRACT

A composition comprising PAA nanoparticles containing a post loaded tetrapyrollic photosensitizer and a postloaded imaging agent and methods for making and using same.

28 Claims, 45 Drawing Sheets

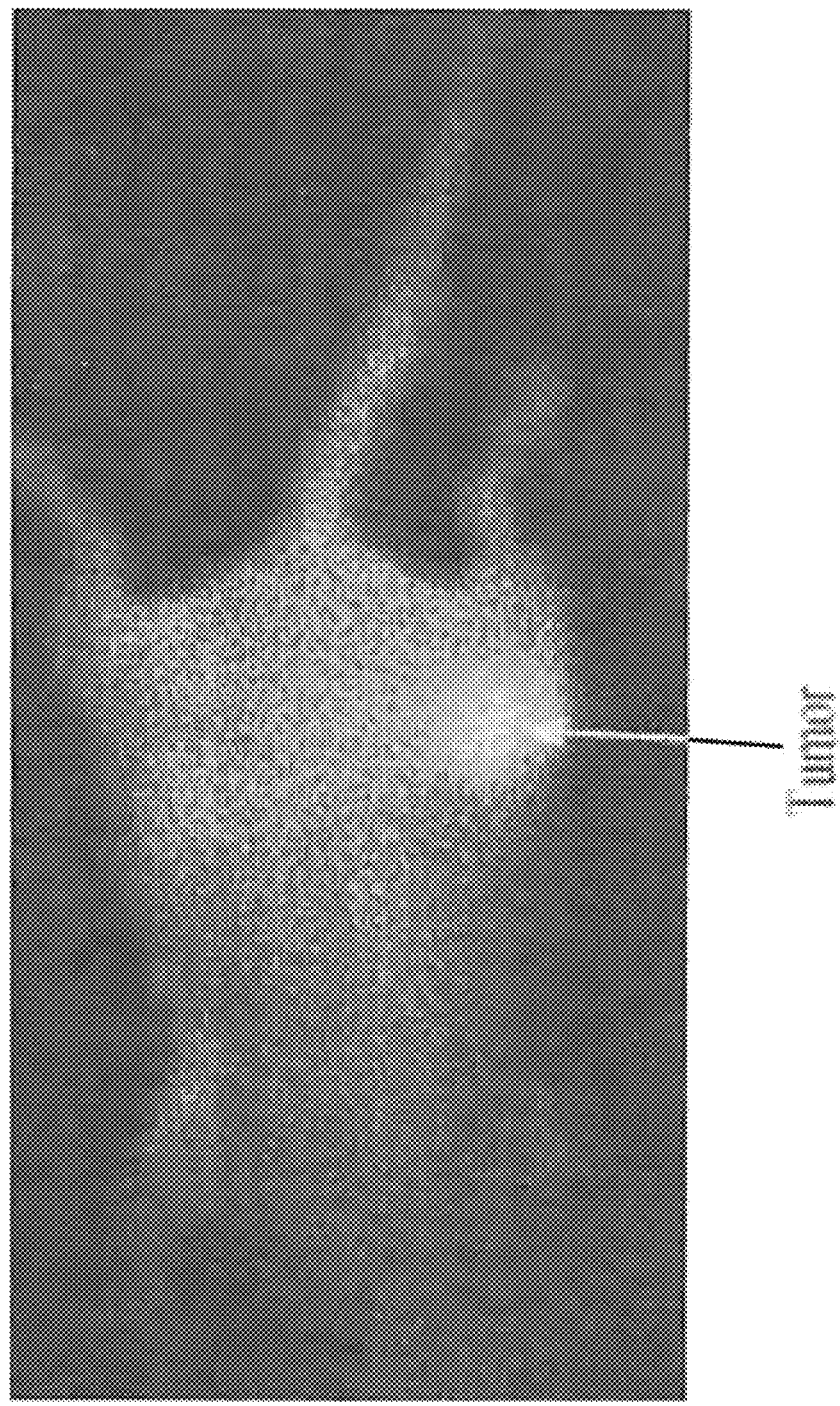

Whole Body Fluorescence Imaging ($\lambda_{ex}$ 782nm and $\lambda_{em}$ >830nm)

MULTIFUNCTIONAL NANOPLATFORMS FOR FLUORESCENCE IMAGING AND PHOTODYNAMIC THERAPY DEVELOPED BY POST-LOADING PHOTOSENSITIZER AND FLUOROPHORE TO POLYACRYLAMIDE NANOPARTICLES

CROSS-REFERENCE TO RELATED APPLICATIONS

This application is a continuation-in-part of U.S. patent application Ser. No. 12/909,573 filed Oct. 21, 2010 which in turn claims the benefit under 35 U.S.C. § 119(e) of U.S. Provisional Application No. 61/279,522, filed Oct. 21, 2009, which applications are incorporated by reference herein in their entirety.

STATEMENT REGARDING FEDERALLY SPONSORED RESEARCH OR DEVELOPMENT

This invention was made with government support under Grant Numbers CA119358 and CA114053 awarded by the National Institutes of Health. The government has certain rights in the invention.

BACKGROUND OF THE INVENTION

A major challenge of cancer therapy is preferential destruction of malignant cells with sparing of normal tissue. Critical for successful eradication of malignant disease are early detection and selective ablation of the malignancy. Photodynamic therapy (PDT) is a clinically effective and still evolving locally selective therapy for cancers. The utility of PDT has been demonstrated with various photosensitizers for multiple types of disease. It is FDA approved for early and late stage lung cancer, obstructive esophageal cancer, high-grade dysplasia associated with Barrett's esophagus, age-related macular degeneration and actinic keratoses. PDT employs tumor localizing photosensitizers that produce reactive singlet oxygen upon absorption of light which is believed to be responsible for the destruction of the tumor. Subsequent oxidation-reduction reactions also can produce superoxide anions, hydrogen peroxide and hydroxyl radicals which contribute to tumor ablation4. Photosensitizers have been designed which localize relatively specifically to certain subcellular structures such as mitochondria, which are highly sensitive targets. On the tumor tissue level, direct photodynamic tumor cell kill, destruction of the tumor supporting vasculature and possibly activation of the innate and adaptive anti-tumor immune system interact to destroy the malignant tissue6. The preferential killing of the targeted cells (e.g. tumor), rather than adjacent normal tissues, is essential for PDT, and the preferential target damage achieved in clinical applications is a major driving force behind the use of the modality. The success of PDT relies on development of tumor-avid molecules that are preferentially retained in malignant cells but cleared from normal tissues.

In efforts to develop effective photosensitizers with the required photophysical characteristics, compounds having a tetrapyrollic core ring were used. Usually, chlorophyll-a and bacteriochlorophyll-a were used as intermediates in synthesis. Extensive QSAR studies on a series of the alkyl ether derivatives of pyropheophorbide-a (660 nm) led to selection of HPPH (hexyl ether derivative), now in promising Phase II clinical trials. Photosensitizer development now extends to purpurinimide (700 nm) and bacteriopurpurinimde (780-800 nm) series with high singlet oxygen producing capability. Long wavelength absorption is important for treating large deep seated tumors, because longer wavelength light increases penetration and minimizes the number of optical fibers needed for light delivery within the tumor.

Various efforts have been made to target tumor cells so that an agent may destroy the tumor cells while sparing normal cells. Such systems are reliant upon specific receptors and as such must reach receptor location. This is a disadvantage since even though the agent may reach the targeted cell, it may not be effective unless the particular receptor is reached and bound.

Multiple, complementary techniques for tumor detection, including magnetic resonance, scintigraphic and optical imaging are under active development. Each approach has particular strengths and advantages. Optical imaging includes measurement of absorption of endogenous molecules (e.g. hemoglobin) or administered dyes, detection of bioluminescence in preclinical models, and detection of fluorescence from endogenous fluorophores or from targeted exogenous molecules.

Fluorescence imaging is a non-invasive and non-ionizing imaging technique that requires only nanomoles of fluorophores for contrast enhancement. The NIR spectral range (~650-950 nm) is known as the "biological window" for optical imaging since light absorption due to water, deoxygenated hemoglobin and oxygenated hemoglobin is minimized in this region, as well as tissue autofluorescence and light scattering.

Fluorescence, the emission of absorbed light at a longer wavelength, can be highly sensitive: a typical cyanine dye with a lifetime of 0.6 nsec can emit up to 1032 photons/second/mole. A sensitive optical detector can image<103 photons/second. Thus even with low excitation power, low levels of fluorescent molecular beacons can be detected. A challenge is to deliver the dyes selectively and in high enough concentration to detect small tumors. Use of ICG alone to image hypervascular or "leaky" angiogenic vessels around tumors has been disappointing, due to its limited intrinsic tumor selectivity. Multiple approaches have been employed to improve optical probe-localization, including administering it in a quenched form that is activated within tumors, or coupling it to antibodies or small molecules such as receptor ligands. Recent studies have focused on developing dye conjugates of small bioactive molecules, to improve rapid diffusion to target tissue and use combinatorial and high throughput strategies to identify, optimize, and enhance in vivo stability of the new probes. Some peptide analogs of ICG derivatives have moderate tumor specificity and are entering pre-clinical studies. However, none of these compounds are designed for both tumor detection and therapy. It is important to develop targeting strategies that cope with the heterogeneity of tumors in vivo, where there are inconsistent and varying expressions of targetable sites.

Photosensitizers (photosensitizer) generally fluoresce and their fluorescence properties in vivo has been exploited for the detection of early-stage cancers in the lung, bladder and other sites. For treatment of early disease or for deep seated tumors the fluorescence can be used to guide the activating light. However, photosensitizer are not optimal fluorophores for tumor detection for several reasons: (i) They have low fluorescence quantum yields (especially the long wavelength photosensitizers related to bacteriochlorins). Efficient photosensitizer tend to have lower fluorescence efficiency (quantum yield) than compounds designed to be fluorophores, such as cyanine dyes because the excited singlet state energy emitted as fluorescence is instead transferred to the triplet state and then to molecular oxygen. (ii) They have small Stokes shifts. Porphyrin-based photosensitizer have a relatively small difference between the long wavelength absorption band and the fluorescence wavelength (Stokes shift), which makes it technically difficult to separate the fluorescence from the excitation wavelength. (iii) Most photosensitizers have relatively short fluorescent wavelengths, <800 nm, which are not optimal for detection deep in tissues.

Attempts have been made to develop bifunctional conjugates that use tumor-avid photosensitizer to target the NIR fluorophores to the tumor. The function of the fluorophore is to visualize the tumor location and treatment site. The presence of the photosensitizer allows subsequent tumor ablation. The optical imaging allows the clinician performing PDT to continuously acquire and display patient data in real-time. This "see and treat" approach may determine where to treat superficial carcinomas and how to reach deep-seated tumors in sites such as the breast, lung and brain with optical fibers delivering the photo-activating light. A similar approach was also used for developing potential PDT/MRI conjugates in which HPPH was conjugated with Gd(III)DTPA Due to a significant difference between imaging and therapeutic doses, the use of a single molecule that includes both modalities is problematic.

Positron emission tomography (PET) is a technique that permits non-invasive use of radioisotope labeled molecular imaging probes to image and assay biochemical processes at the level of cellular function in living subjects20. PET predominately has been used as a metabolic marker, without specific targeting to malignancies. Recently, there has been growing use of radiolabeled peptide ligands to target malignancies. Currently, PET is important in clinical care and is a critical component in biomedical research, supporting a wide range of applications, including studies of tumor hypoxia, apoptosis and angiogenesis21. For targeting, a long circulation time may be desirable, as it can increase delivery of the agent into tumors. HPPH and the iodobenzyl pheophorbide-a have plasma half lives ~25 h. The long radiological half life of $^{124}$I is well matched to the pheophorbides; it permits sequential imaging with time for clearance from normal tissue. Labeling techniques with radioiodine are well defined with good yield and radiochemical purity22. Despite the complex decay scheme of $^{124}$I which results in only 25% abundance of positron (compared with 100% positron emission of 18F), in vivo quantitative imaging with $^{124}$I labeled antibodies has been successfully carried out under realistic conditions using a PET/CT scanner A variety of biomolecules have been labeled with $^{124}$I. We have devised a coupling reaction which rapidly and efficiently links $^{124}$I to a tumor-avid photosensitizer23-25, and used the conjugate to target and image murine breast tumor and its metastasis to lung Acquisition of clinical PET images can be slow, but combination PET-CT scanners allow real time guidance of therapeutic interventions. Also, new developments in tracking may permit real time interventions guided by PET data sets.

Both cancer detection and treatment depend on selective delivery of appropriate agents to the malignancy. Photodynamic therapy (PDT), a relatively new modality for the treatment of a variety of oncological, cardiovascular, dermatological and ophthalmic diseases, is based on the preferential localization of photosensitizing molecules, (photosensitizers, PS) in target tissues. Upon light activation, the PS produces reactive singlet oxygen[5] which damages tumor cells and neovasculature, and also initiates antitumor inflammatory and immune responses. We and others have developed relatively tumor-avid PS which selectively accumulate in tumor, and these molecules have been used to carry optical, PET and MR imaging agents to the tumor sites. However, the tumor selectivity of current PS is not always adequate. Approaches that link PS to antibody fragments or receptor ligands have been disappointing because the number of required PS/cell generally is greater than the number of antigen or receptor binding sites. Conversely, the imaging agent carrying capacity of the individual PS molecules is limited.

It has recently been shown that HPPH, developed in our laboratory and currently under Phase I/II clinical trials, when conjugated with certain cyanine dyes can be used for both fluorescence imaging and photodynamic therapy. The conjugate showed potential tumor imaging and PDT efficacy, but compared to the imaging dose the required therapeutic dose was 8-fold higher. Increasing the number of HPPH moieties in synthetic photosensitizer-cyanine dye (PS-CD) conjugates did not minimize the therapeutic dose.

Nanoscience is being developed in conjunction with advanced medical science for further precision in diagnosis and treatment. Nanoplatforms and nanovectors that deliver a therapeutic or imaging agent for biomedical applications show promise for cancer diagnosis and therapy. Therapeutic examples include nanoparticles containing PDT agents, folate receptor-targeted, boron containing dendrimers for neutron capture and nanoparticle-directed thermal therapy.

Nanoparticles have had disadvantages when considered for use in photodynamic therapy (PDT). In particular, certain nanoparticles have no relatively large knowledge base on cancer imaging, PDT, chemical sensing, stability and biodegradation. (2) have in in-vivo toxicity. (3) Have short plasma circulation time without surface modification and unstable or uncontrollable biodegradation and bioelimination rates (4) Have problems associated with scale-up and are not storage stabile over extended periods. And (5) have additional limitations including relative difficulty in incorporating hydrophobic compounds, leaching of small hydrophilic components unless they are "anchored", and unknown limitation on bulk tumor permeability because of hydrogel swelling.

Nevertheless, nanoparticles (NP) are uniquely promising in that (i) their hydrophilicity and charge can be altered; (ii) they possess enormous surface area which can be modified with functional groups possessing a diverse array of chemical and biochemical properties, including tumor-selective ligands; (iii) owing to their sub-cellular and sub-micron size, they can penetrate deep into tissues and are generally taken up efficiently by cells.

BRIEF SUMMARY OF THE INVENTION

The present invention relates to polyacrylic acid (PAA) nanoparticles containing a photosensitizer and an imaging enhancing agent.

In accordance with the invention, therapeutic and imaging potential of encaphotosensitizerulated, post-loaded and covalently linked photosensitizer-nanoparticles have been evaluated. In PAA nanoparticle the post-loading efficiency showed enhanced in vitro/in vivo therapeutic and imaging potential. PAA nanoparticle have core matrixes that can readily incorporate molecular or small nanoparticle payloads, and can be prepared in 10-150 nm sizes, with good control of size distributions. The surfaces of nanoparticles can be readily functionalized, to permit attachment of targeting ligands, and both are stable to singlet oxygen (1O2) produced during photodynamic therapy (PDT). PAA-nanoparticles, i.e. poly(acrylic acid) nanoparticles, have the advantages of (1) A relatively large knowledge base on cancer imaging, PDT, chemical sensing, stability and biodegradation. (2) No known in-vivo toxicity. (3) Long plasma circulation time without surface modification, but with biodegradation and bioelimination rates controllable via the type and amount of selective cross-linking (introduced during polymerization inside reverse micelles). (4) Scale-up to 400 g material has been demonstrated, as well as storage stability over extended periods. Limitations have included relative difficulty in incorporating hydrophobic compounds, leaching of small hydrophilic components unless they are "anchored", and unknown limitation on bulk tumor permeability because of hydrogel swelling.

In accordance with the invention, photosensitizers have several very desirable properties as therapeutic agents deliverable by PAA nanoparticles. In particular, (1) Only a very small fraction of administered targeted non-photodynamic drug makes it to tumor sites and the remainder can cause systemic toxicity. However, PDT provides dual selectivity in that the photosensitizer is inactive in the absence of light and is innocuous without photoactivation. Thus the photosensitizer contained by the nanoparticle can be locally activated at the site of disease. (2) PDT effects are due to production of singlet oxygen, which, in accordance with the compounds and methods of the invention, can readily diffuse from the pores of the nanoparticle. Thus, in contrast to chemotherapeutic agents, release of encaphotosensitizerulated drug from the nanoparticle, is not necessary. Instead, stable nanoparticles with long plasma residence times can be used, which increases the amount of drug delivered to the tumors. (3) PDT is effective regardless of the intracellular location of the photosensitizer. While mitochondria are a principal target of singlet oxygen, photosensitizer incorporated in lysosomes are also active the photodynamic process causes rupture of the lysosomes with release of proteolytic enzymes and redistribution of the photosensitizer within the cytoplasm. nanoparticle platforms also provide significant advantages for PDT: (1) High levels of imaging agents can be combined with the photosensitizer in the nanoparticle permitting a "see and treat" approach, with fluorescence image guided placement of optical fibers to direct the photoactivating light to large or subsurface tumors, or to early non clinically evident disease. (2) It is possible to add targeting moieties, such as cRGD or F3 peptide to the nanoparticle so as to increase the selective delivery of the photosensitizer. (3) The nanoparticle can carry large numbers of photosensitizers, and their surface can be modified to provide the desired hydrophilicity for optimal plasma pharmacokinetics. Thus, they can deliver high levels of photosensitizer to tumors, reducing the amount of light necessary for tumor cure.

The photosensitizer is preferably a tetrapyrollic photosensitizer having the structural formula:

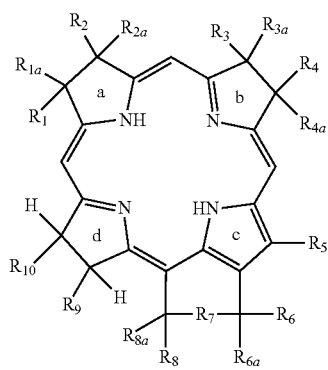

or a pharmaceutically acceptable derivative thereof, wherein:

$R_1$ and $R_2$ are each independently substituted or unsubstituted alkyl, substituted or unsubstituted alkenyl, —C(O)$R_a$ or —COOR$_a$ or —CH(CH$_3$)(OR$_a$) or —CH(CH$_3$)(O(CH$_2$)$_n$XR$_a$) where $R_a$ is hydrogen, substituted or unsubstituted alkyl, substituted or unsubstituted, alkenyl, substituted or unsubstituted alkynyl, or substituted or unsubstituted cycloalkyl; where $R_2$ may be —CH=CH$_2$, —CH(OR$_{20}$)CH$_3$, —C(O)Me, —C(=NR$_{21}$)CH$_3$ or —CH(NHR$_{21}$)CH$_3$;

where X is an aryl or heteroaryl group;

n is an integer of 0 to 6;

where $R_{20}$ is methyl, butyl, heptyl, docecyl or 3,5-bis(trifluoromethyl)-benzyl; and $R_{21}$ is 3,5,-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaralkyl or =NR$_{20}$ where $R_{20}$ in =NR$_{20}$ is 3,5-bis(tri-fluoromethyl)benzyl or —CH$_2$X—R$^1$ or —YR$^1$ where Y is an aryl or heteroaryl group;

$R_8$ and $R_{8a}$ are each independently hydrogen or substituted or unsubstituted alkyl or together form =O;

$R_9$ and $R_{10}$ are each independently hydrogen, or substituted or unsubstituted alkyl and $R_9$ may be —CH$_2$CH$_2$COOR$^2$ where $R^2$ is an alkyl group that may optionally substituted with one or more fluorine atoms;

each of $R_1$-$R_{10}$, when substituted, is substituted with one or more substituents each independently selected from Q, where Q is alkyl, haloalkyl, halo, photosensitizereudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ and each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, photosensitizereudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue.

The photosensitizer may be conjugated with an image enhancing agent prior to incorporation into the nanoparticle, after incorporation into the nanoparticle or the photosensitizer and/or image enhancing agent may chemically bound to the nano particle and/or one or more of the photosensitizer and image enhancing agent may be physically bound to the nanoparticle.

Imaging enhancing agents may be for essentially any imaging process, e.g. Examples of such imaging enhancing agents are discussed in the background of the invention previously discussed and in the list of references incorporated by reference herein as background art.

It is to be understood that other agents may be incorporated into the nanoparticle such as tumor targeting moieties and tumor inhibiting or tumor toxic moieties. In particular, a novel post-loading approach for constructing a multifunctional biodegradable polyacrylamide (PAA) nanoplatform for tumor-imaging (fluorescence) and photodynamic therapy (PDT is provided. This approach provides an opportunity to post-load the imaging and therapeutic agents at desired concentrations. Among the PAA nanoparticles, a formulation containing the photosensitizer, HPPH [3-(1'-hexyloxyethyl)pyropheophorbide-a], and the cyanine dye in a ratio of 2:1 minimized the undesirable quenching of the HPPH electronic excitation energy due to energy migration within the nanoparticles and/or Förster (fluorescence) resonance energy transfer (FRET) between HPPH and cyanine dye. An excellent tumor-imaging (NIR fluorescence) and phototherapeutic efficacy of the nanoconstruct formulation is demonstrated. Under similar treatment parameters the HPPH in 1% Tween 80/5% aqueous dextrose formulation was less effective than the nanoconstruct containing HPPH and cyanine dye in a ratio of 2 to 1. This is the first example showing the utility of the post-loading approach in developing a nanoconstructs for tumor-imaging and therapy.

BRIEF DESCRIPTION OF THE SEVERAL VIEWS OF THE DRAWINGS

As used herein "Figure" and "Fig." are used interchangeably.

FIG. 1C shows a scanned image showing localization of the conjugate 1 in a live mouse 24 h after injection (drug dose 0.3 µmole/kg). (Without PAA NP0

FIGS. 24K and 24L show Release Profiles of PS 1 and cyanine dye 3 from nanoconstruct 7 in a 25% Bovine Calf Serum (BCS) solution at 37° C.

DETAILED DESCRIPTION OF THE INVENTION

Photosensitizers (photosensitizer) generally fluorescence and their fluorescence properties in vivo has been exploited for the detection of early-stage cancers in the lung, bladder and other sites. For treatment of early disease or for deep seated tumors the fluorescence can be used to guide the activating light. However, photosensitizers are not optimal fluorophores for tumor detection for several reasons: (i) They have low fluorescence quantum yields (especially the long wavelength photosensitizers related to bacteriochlorins). Efficient photosensitizer tend to have lower fluorescence efficiency (quantum yield) than compounds designed to be fluorophores, such as cyanine dyes because the excited singlet state energy emitted as fluorescence is instead transferred to the triplet state and then to molecular oxygen. (ii) They have small Stokes shifts. Porphyrin-based photosensitizer have a relatively small difference between the long wavelength absorption band and the fluorescence wavelength (Stokes shift), which makes it technically difficult to separate the fluorescence from the excitation wavelength. (iii) Most photosensitizer have relatively short fluorescent wavelengths, <800 nm, which are not optimal for detection deep in tissues.

Figure 1A:
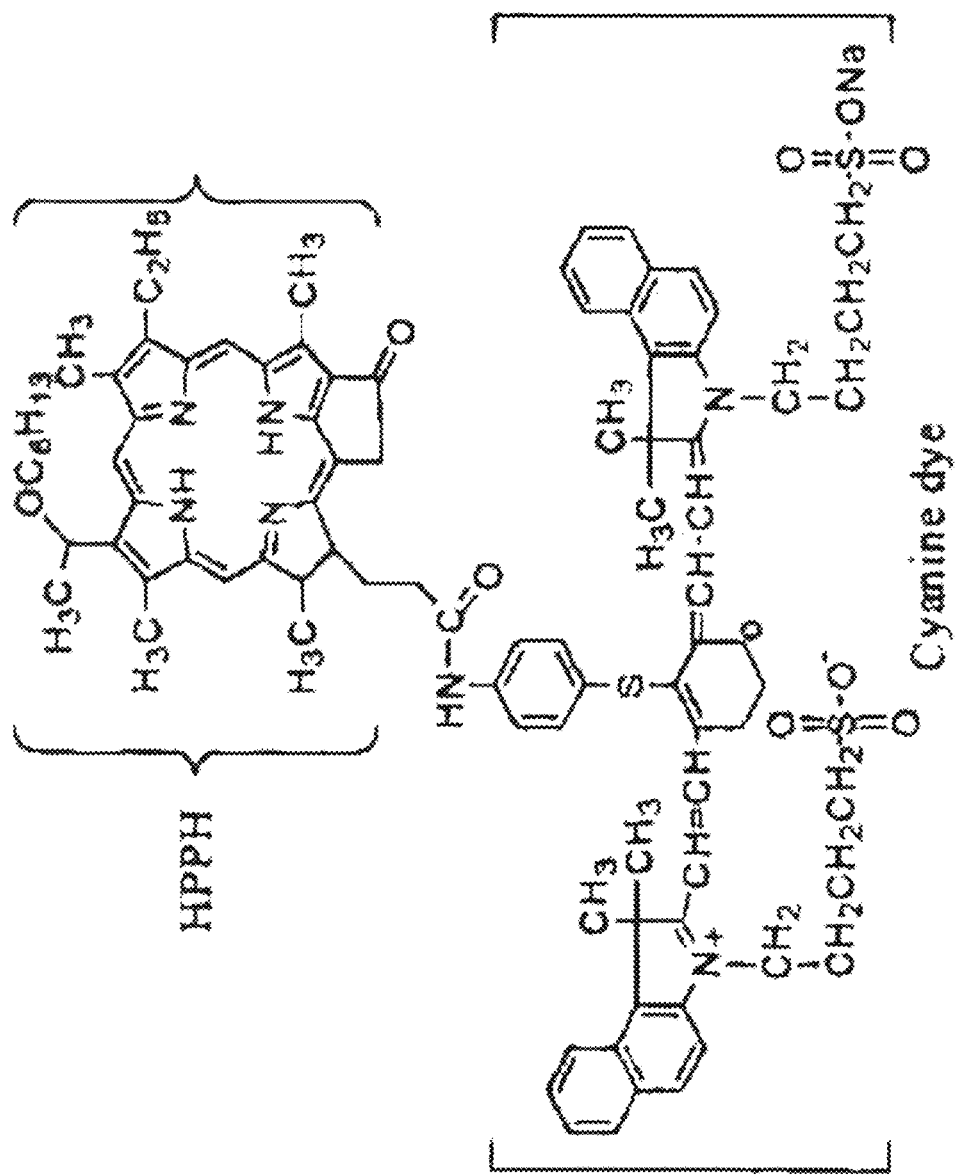
FIG. 1A shows the structural formula of HPPH-CD (cyanine dye) conjugate used as a photosensitizer and imaging agent.
Figure 1B:
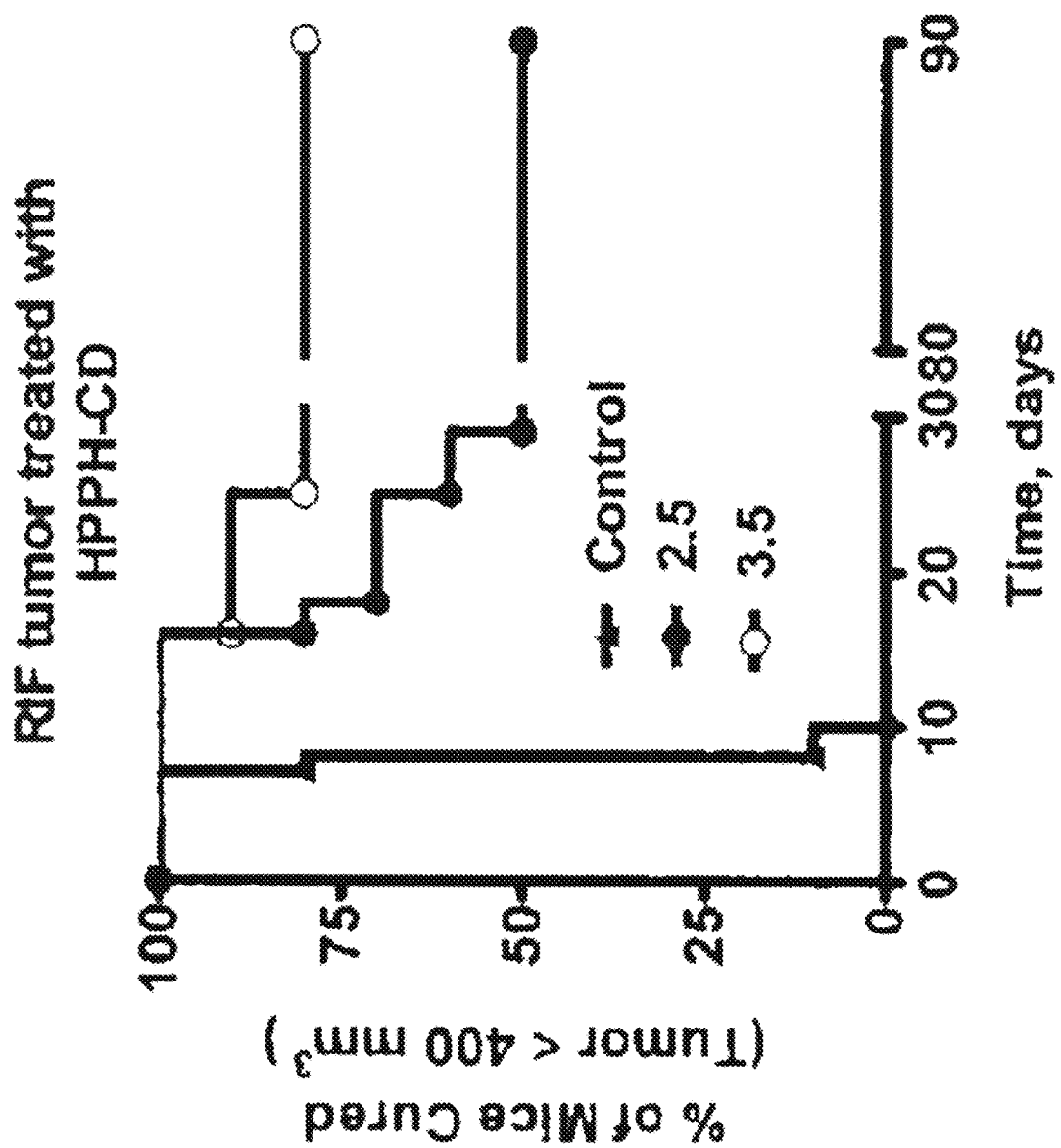
FIG. 1B is a graph showing in vivo photosensitizing efficacy of HPPH-CD conjugate 1 in C3H mice bearing RIF tumors (10 mice/group) at variable drug doses. The tumors were exposed to light (135 J/cm2/75 mW/cm2) at 24 h post-injection.

We have previously shown that certain tumor-avid photosensitizer(s) (e.g., HPPH) conjugated with NIR absorbing fluorophore(s) (non-tumor specific cyanine dyes) can be used as bifunctional agents for tumor-imaging by fluorescence and phototherapy (PDT). Here, HPPH was used as a vehicle to deliver the imaging agent to tumor. The limitation of this approach was that the conjugate exhibited significantly different dose requirements for the two modalities. The imaging dose was approximately 10-fold lower than the phototherapeutic dose (FIGS. 1B and 1C), which could be due to a part of the singlet oxygen (a key cytotoxic agent responsible for the destruction of the tumors) produced on exciting the photosensitizer being quenched by the fluorophore leading to its photo-destruction. Exposing the tumor at 780 nm (excitation wavelength for the cyanine dye) produced in vivo emission at 860 nm and, as expected, no significant photobleaching of the fluorophore (CD) or the photosensitizer (HPPH) was observed.

We have thus developed multifunctional nanovector platforms that can deliver tumor-avid therapeutic photosensitizers that only become active (and toxic) when illuminated by specific wavelengths of light, and, in addition, carry one or more imaging agents; these nano-platforms thus could enable both diagnosis and image guided therapy.

Among the nanoparticles, hydrogel polyacrylamide (PAA) in which the monomeric units are linked together with ester bonds have been of particular interest due to their biocompatibility/biodegradability and low toxicity Using biodegradable polymer based nanoparticles (NPs) avoids multi-step synthesis and has numerous advantages including the ability to create water soluble formulations with desired pharmacokinetic properties, capable of delivering a high payload of the multiple agents (therapeutic PS and imaging agents) to tumors, increased photostability of photoactive agents and fluorophores, and the ability to modify the surface of the NP for conjugation to a variety of biomolecules. NPs and other macromolecular objects can passively target the tumor interstitium, via the "Enhanced Permeability and Retention" (EPR) effect due to the leaky vascular system in tumors.[21a,b] In addition, the poor lymphatic drainage system in tumors causes fluid retention in the tumor interstitial space, which helps to retain polymeric nanoparticles and other macromolecular objects in the tumor compared to normal tissue.[21a,b] For these reasons, NPs are a promising means for delivering therapeutic and other molecular agents to tumors.

Because NPs could deliver a high payload of the drug to tumor, we investigated the use of a PAA-based nanoconstructs for delivering both the near-infrared (NIR) cyanine dye (CD) fluorophore and the red-light absorbing photosensitizer HPPH. The release of the desired imaging and therapeutic agents may also be controlled by creating a nanoparticle that is pH or temperature sensitive, or by modifying the pores of the NP matrix In a parallel study we encapsulated the PS within polymeric NPs, but the retention efficiency was low, therefore a large concentration of NPs was required to achieve the desired therapeutic dose. To increase the retention of the PS within the NP, we decided to form the NPs first and then load the PS into the porous PAA-NPs. This novel loading approach of the desired agents was termed "post-loading". In this procedure, both HPPH (phototherapeutic agent) and the cyanine dye (NIR fluorescence imaging agent) moieties were highly retained in the NPs (confirmed by release kinetics) and provided constructs for non-invasive detection of tumors and delineation of the tumor margins by NIR fluorescence imaging.

Figure 2:
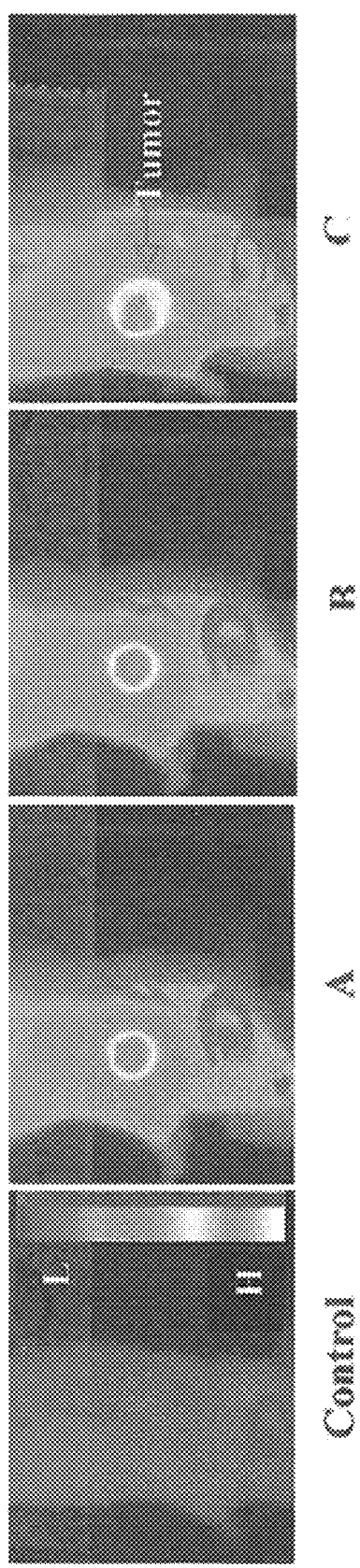
FIG. 2 shows whole body images of BALB/c mice bearing Colon26 tumors with PAA NPs formulations (HPPH and cyanine dye (CD) were post-loaded in 2 to 1 ratio). The CD concentration was kept constant (0.3 µmol/kg) at the images were obtained at variable time points. A=24 h, B=48 h and C=72 h post injection (λex: 785 nm; λEm: 830 nm). L=Low and H=High.
Figure 3:
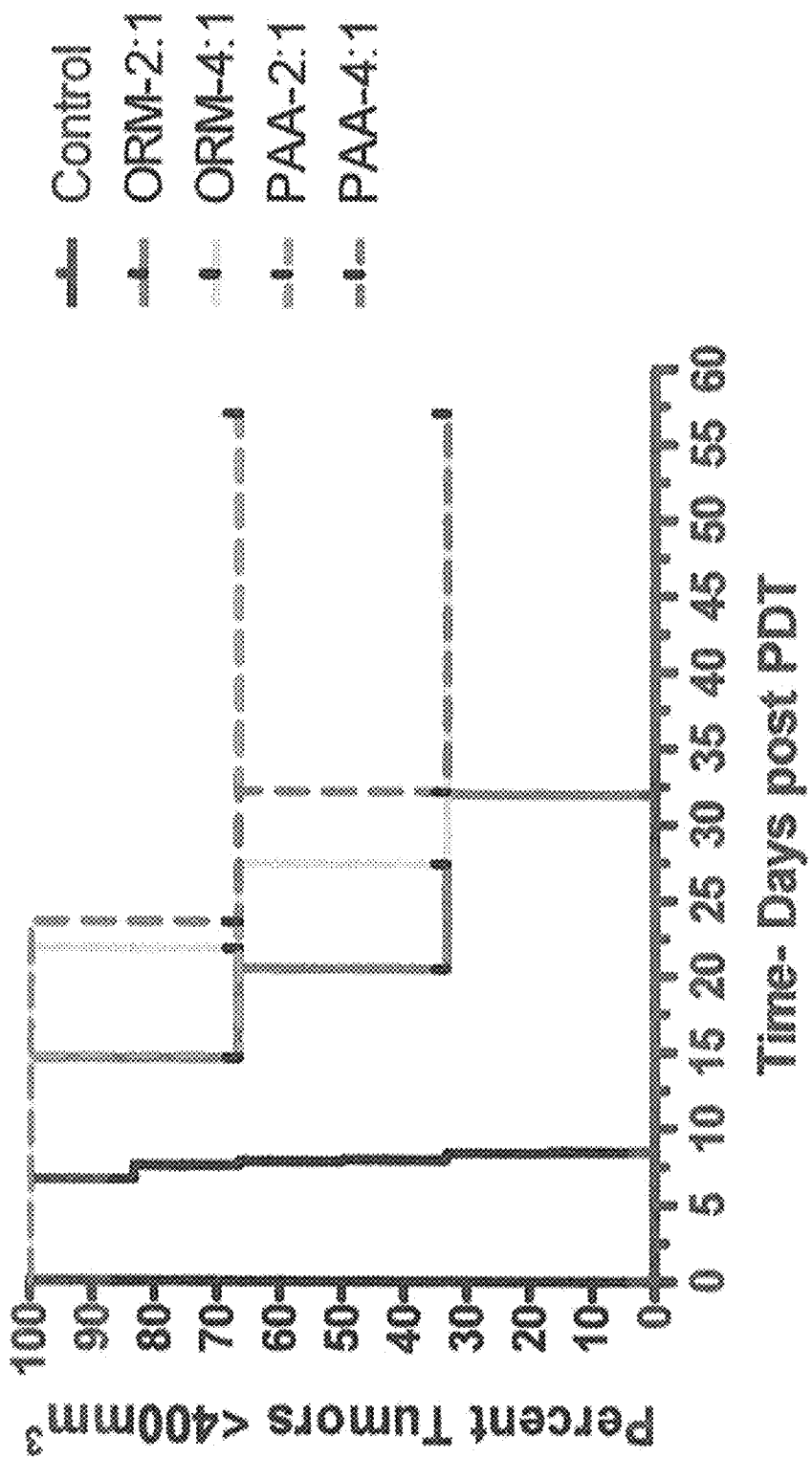
FIG. 3 is a graph showing in vivo PDT efficacy of HPPH and CD post loaded in a ratio of 2:1 and 4:1 in PAA and ORMOSIL NPs. Note: HPPH dose: 0.47 µmol/kg in PAA NPs and 0.78 µmol/kg in ORMOSIL NPs.
Figure 4:
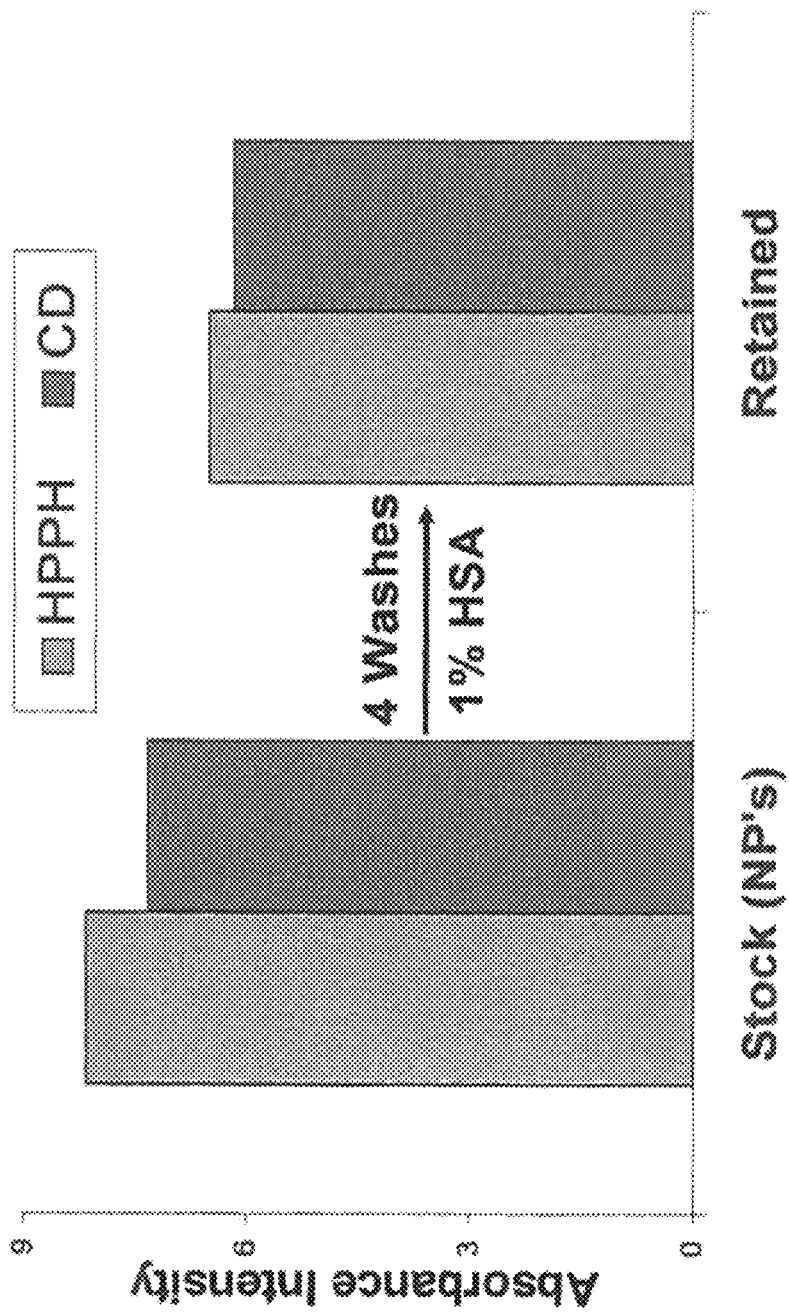
FIG. 4. Slow release of HPPH and CD from PAA NPs (post loaded in 2:1 ratio) after several washes with 1% HSA.
Figure 5A:
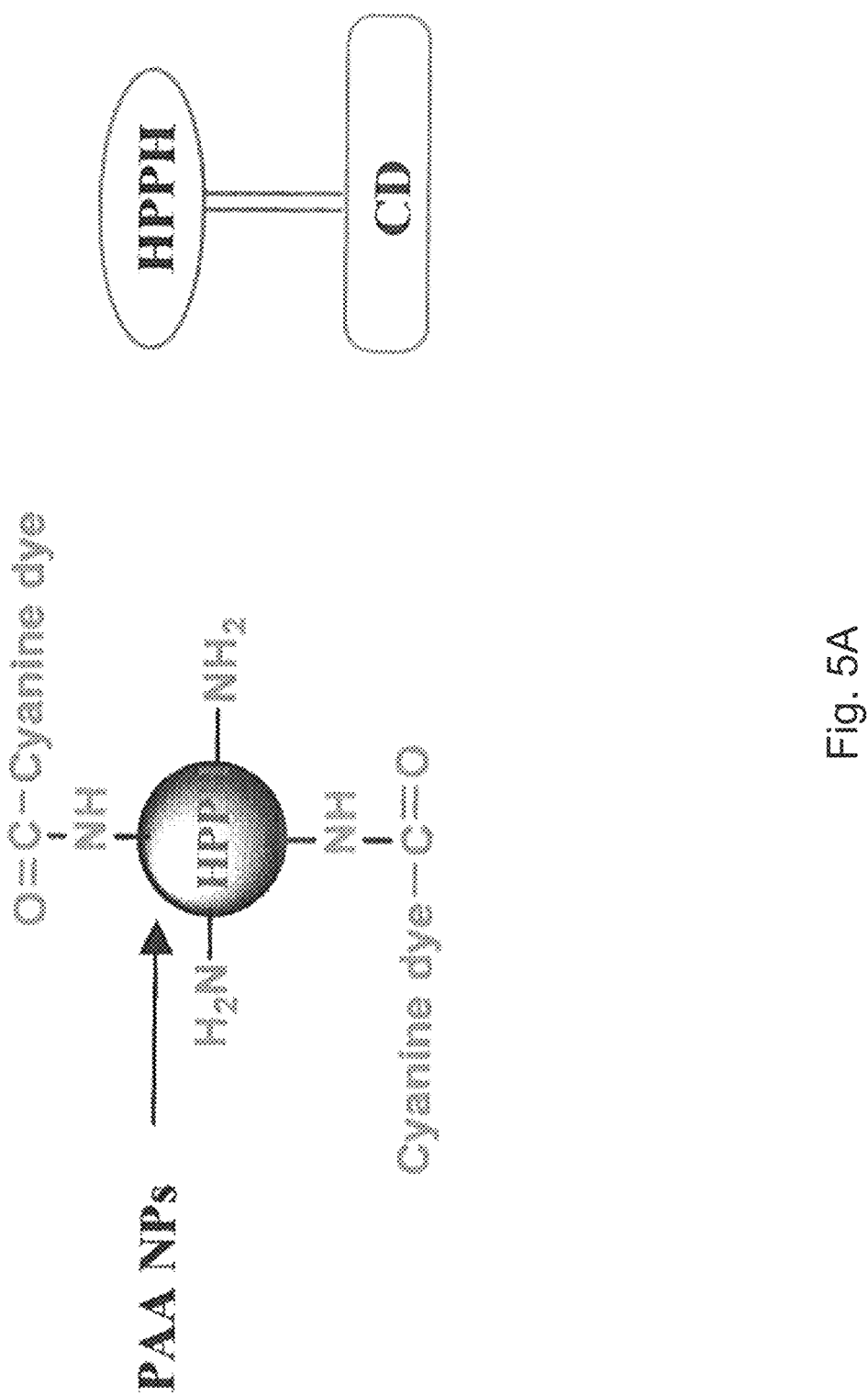
FIG. 5A is a diagram showing structure of PAA nanoparticles (PAA NP's)
Figure 5B:
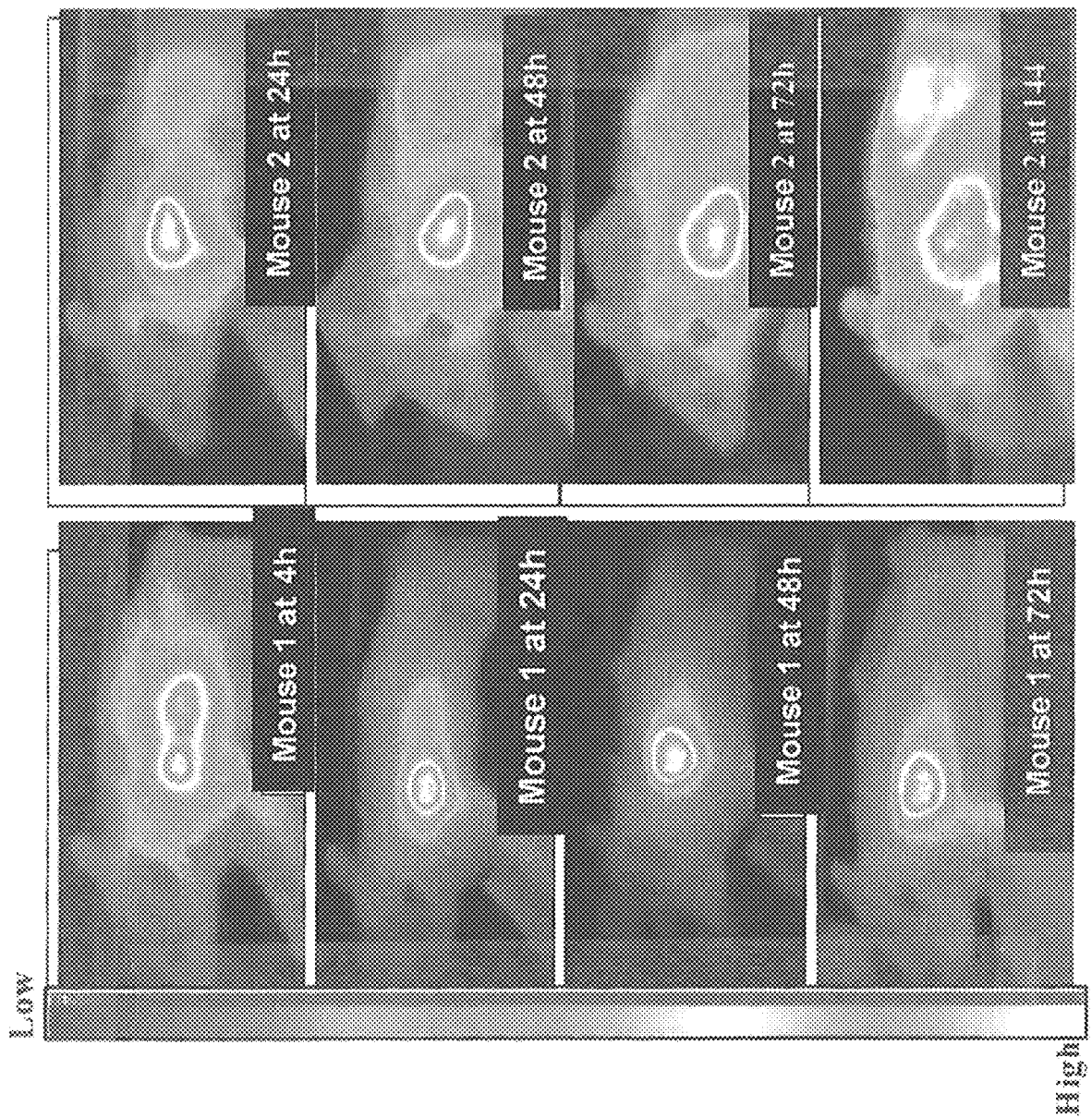
FIG. 5B shows comparative in vivo imaging at variable time points of BALB/c mice bearing Colon 26 tumors with HPPH-CD conjugate 1 and CD-conjugated with PAA NPs/post; -loaded with HPPH. The NPs were more tumor specific. (Mouse 1)

For investigating the utility of PAA nanoparticles three different approaches were used. First HPPH and the cyanine dye (fluorophore) were post-loaded in variable ratios (HPPH to CD: 1:1; 2:1; 3:1 and 4:1 molar concentrations). In brief, HPPH was postloaded to PAA nanoparticles first. Free HPPH was removed by spin filtration and then cyanine dye was postloaded. It was spin-filtered again, washed several times with 1% bovine calf serum and the concentration was measured. The 2:1 formulations produce the best tumor imaging and long-term tumor cure in BALB/c mice bearing Colon26 tumors. This formulation contained in a single dose the therapeutic dose of HPPH (0.47 µmol/kg) and the imaging dose of Cyanine dye (0.27 mol/kg), which were similar to the components used alone for tumor imaging and therapy, but with much more tumor selectivity (skin to tumor ratio of HPPH was 4:1 instead of 2:1 without nanoparticles). Under similar treatment parameters the Ormosil nanoparticles showed a significantly reduced response (imaging and PDT, not shown). The stability of the drugs in PAA nanoparticle was established by repeated washing with aqueous bovine calf serum through Amicon centrifugal filter units with a 100 KDa or larger cut off membrane and drug in the filtrate was measured spectrophotometrically. The comparative in vivo PDT efficacy of the ORMOSIL and PAA formulations, their tumor imaging potential and stability (in vitro release kinetics) is shown in FIGS. 2-4, which clearly illustrate the advantages of PAA nanoparticles in reducing the therapeutic dose by almost 8-fold without diminishing the tumor-imaging potential and also avoiding the Tween-80 formulation required for the HPPH-CD conjugate 1. In the $2^{nd}$ approach the HPPH CD conjugate 1 was post-loaded to PAA nanoparticles, which certainly enhanced the tumor imaging, but the therapeutic dose was still 10-fold higher (similar to the HPPH CD conjugate, FIG. 5B). In the 3rd approach the cyanine dye was conjugated peripherally to the PAA nanoparticles first and then HPPH was post loaded. Again, compared to HPPH-CD conjugate 1, the PAA formulation showed enhanced tumor-specificity (imaging) (FIG. 5B).

Effect of Nanoparticles on Tumor Selectivity

A photosensitizer (photosensitizer) with increased selectivity and longer wavelength could be a more suitable candidate for brain and deeply seated tumors (especially breast, brain and lung). The evolution of light sources and delivery systems is also critical to the progression of photodynamic therapy (PDT) in the medical field. Two different techniques: interstitial and intracavitary light delivery have been used for treatment of brain tumors. Powers using interstitial PDT on patients with recurrent brain tumors showed that the majority of patients had tumor recurrence within two months of treatment. However, it was later observed that treatment failures appeared to occur outside the region of the effective light treatment. Chang et al reported an effective radius of tumor cell kill in 22 glioma patients of 8 mm compared with the 1.5 cm depth of necrosis noted by Pierria with the intracavitary illumination method. It is believed that tumor resection is important so that the numbers of tumor cells remaining to treat are minimized. With stereotactic implantation of fibers for interstitial PDT there is no cavity to accommodate swelling and a considerable volume of necrotic tumor which causes cerebral edema. However, cerebral edema can be readily controlled with steroid therapy. Compared to chemotherapy and radiotherapy, patients with brain tumors treated with PDT have definitely shown long-term survival, whereas glioma patients treated with adjuvant chemotherapy or radiotherapy do not seem to show additional benefits. as On the basis of our preliminary data, the$\alpha v\beta 3$ targeted nanoparticles may improve tumor-selectivity and PDT outcome.

Figure 6:
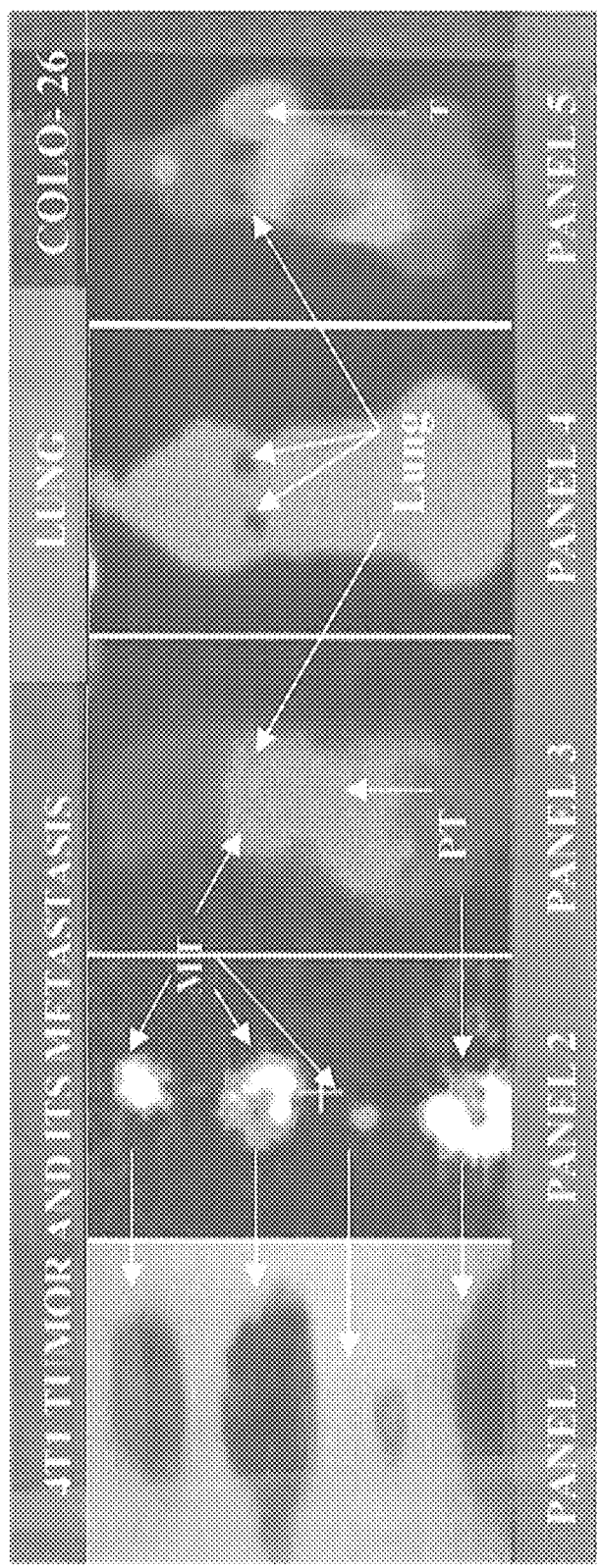
FIG. 6 shows a series of scans wherein Panel 1 (4T1 tumors): Primary (PT) and metastasized tumors (MT) dissected and Panel 2 (4T1 tumors): PET imaging of the dissected primary and metastasized tumors. Panel 3 (BALB/C mouse bearing 4T1 tumor): Whole body PET imaging. The tumor metastasis in lung was clearly observed. Panel 4: The position of the lung is shown by the transmission scan using 57Co source in mice with no lung metastasis. Panel 5: (BALB/C mouse bearing Colo-26 (non-metastatic tumor): Whole body imaging by PET. A high accumulation of the 124I-photosensitizer in tumor is clearly observed without any significant accumulation in lungs (injected dose: 100 µCi). T=Tumor, PT=Primary tumor; MT=Metastatic tumor.
Figure 7:
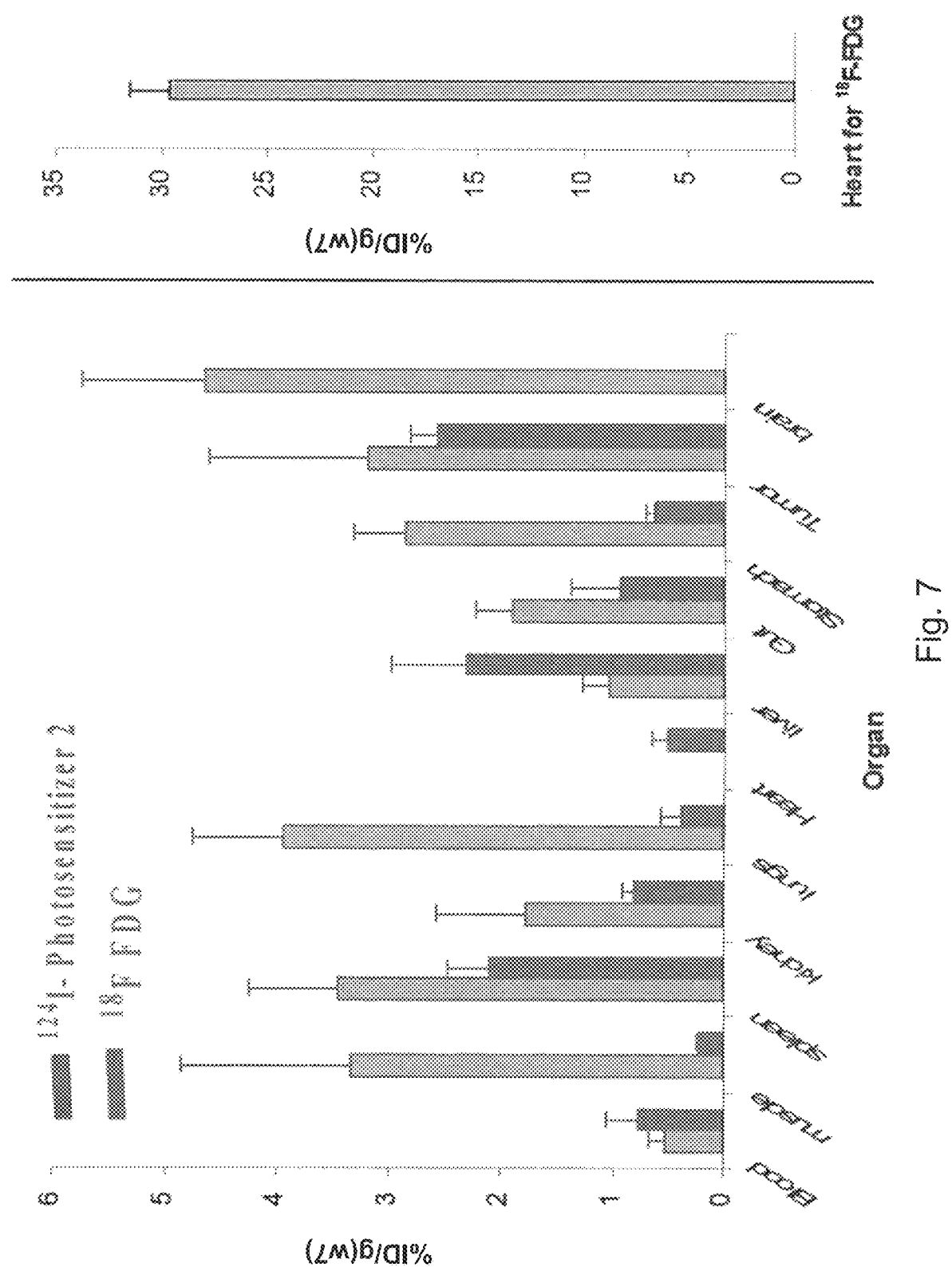
FIG. 7. In vivo biodistribution of 18F-FDG (100 µCi, half-life 2 h) at 110 min and 124I-PS 2 (100 µCi, half-life 4.2 d) at 48 h in BALB/c mice bearing Colon 26 tumor (3 mice/group). Tumor-uptake was similar for both agents. However, the higher uptake of FDG over 124I-PS 2 in normal organs is clearly evident.
Figure 8A:
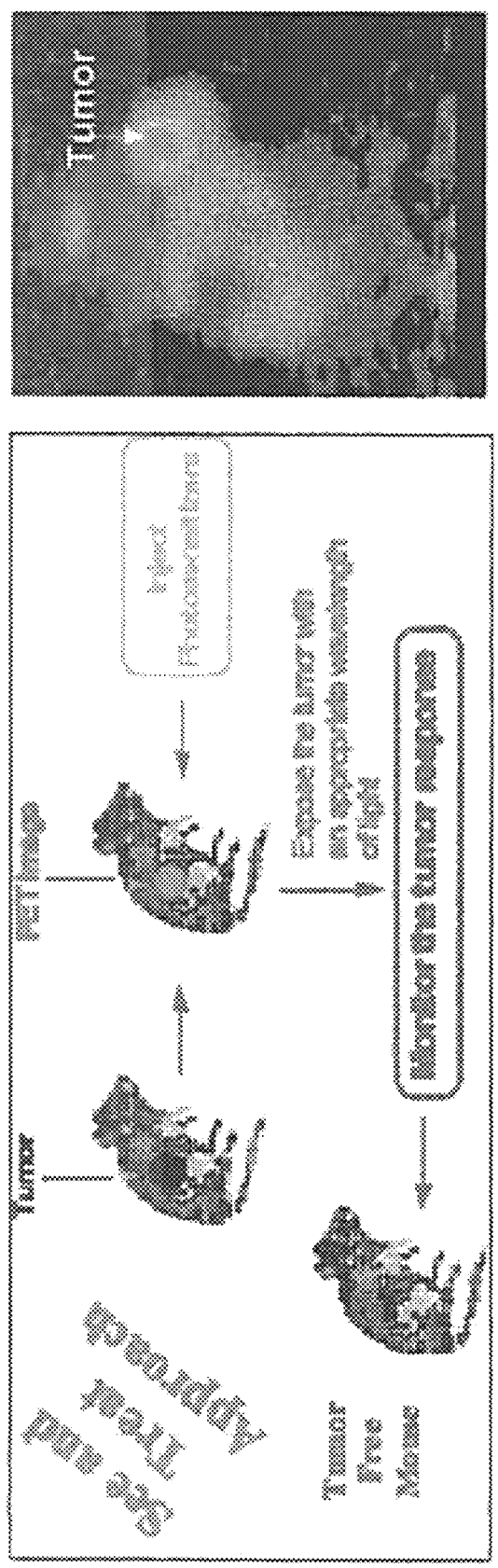
FIG. 8A shows in vivo comparative in vivo PET imaging (72 h post injection) and biodistribution (24 h, 48 h and 72 h postinjection) of 124I-labeled photosensitizer 2 without PAA nanoparticles in BALB/c mice bearing Colon26 tumors (see the text). (Biodistribution of PET imaging agent 2: No PAA, with PAA).
Figure 8B:
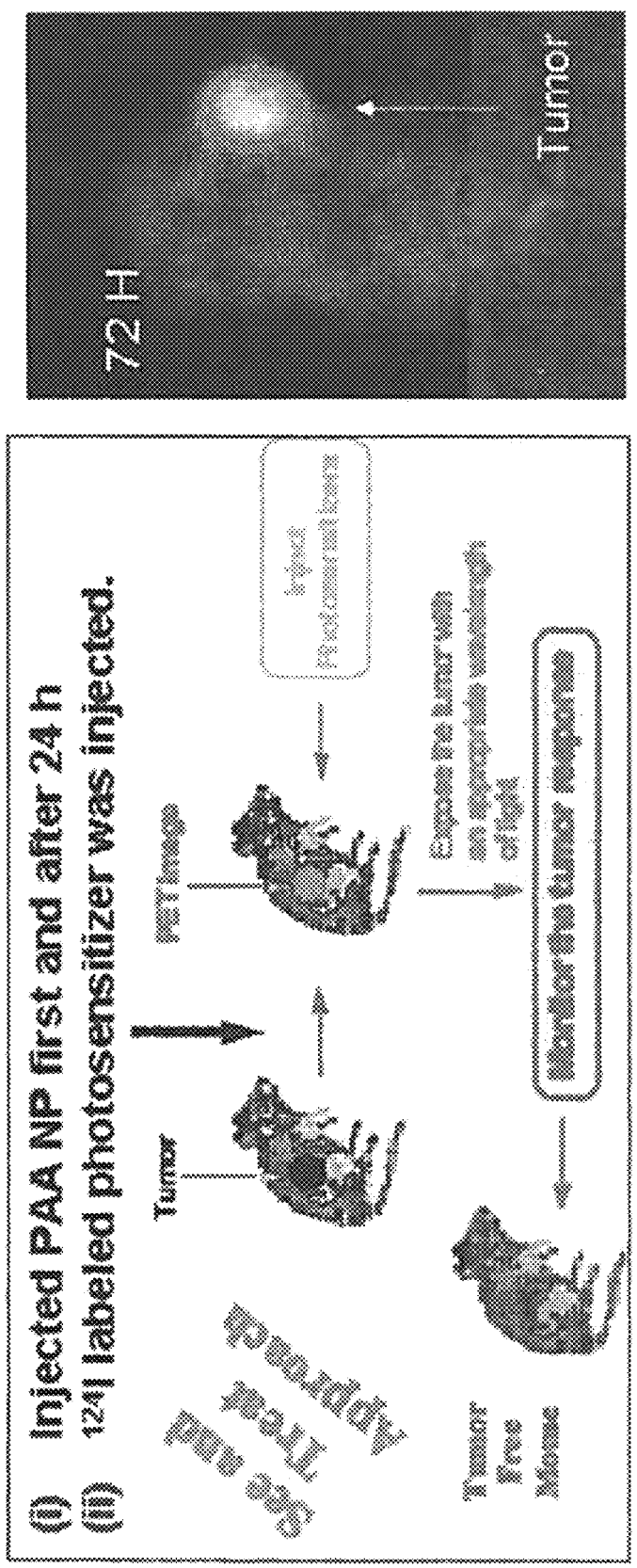
FIG. 8B shows in vivo comparative in vivo PET imaging (72 h post injection) and biodistribution (24 h, 48 h and 72 h postinjection) of 124I-labeled photosensitizer 2 with PAA nanoparticles in BALB/c mice bearing Colon26 tumors (see the text). (Biodistribution of PET imaging agent 2: No PAA, with PAA).
Figure 8C:
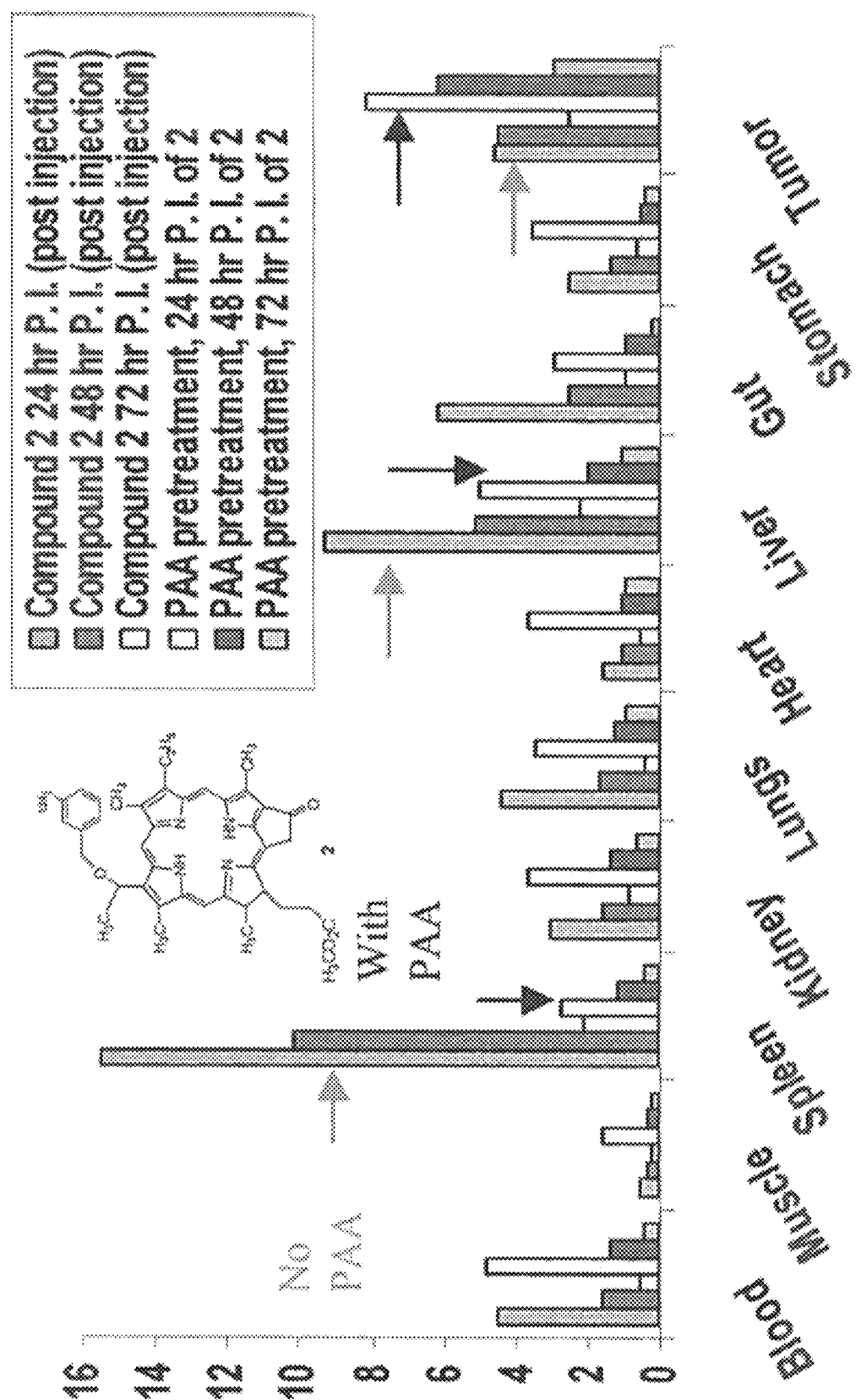
FIG. 8C shows biodistribution of PET imaging agent 2, no PAA and with PAA.

PET Imaging and PDT:

PAA nanoparticles decreased the liver uptake of the 124I-photosensitizer (PET imaging agent) and enhanced the tumor-specificity. Our initial investigation with an 124I-labeled photosensitizer 2 indicates its in vivo PDT efficacy and capability of detecting tumors104-106 (RIF, Colon26, U87, GL261, pancreatic tumor xenograft)) and tumor metastases (BALB/c mice bearing orthotopic 4T1 (breast) tumors) (FIG. 6). Interestingly, compared to 18F FDG photosensitizer 2 showed enhanced contrast in most of the tumors including those where 18F FDG-PET provides limited imaging potential (e.g., brain, lung and pancreatic tumors). See FIG. 7 for comparative biodistribution. This is the first report showing the utility of porphyrin-based compounds as a "BIFUNCTIONAL AGENT" for imaging breast tumor and tumor metastasis. Similar to most nanoparticles, PAA nanoparticles accumulate in liver and spleen. Their clearance rate from most organs is significantly faster than Ormosil nanoparticle and they do not show long-term organ toxicity. Even tumor-avid porphyrinbased photosensitizer exhibit high uptake in liver and spleen, but are non-toxic until exposed to light. The photosensitizer clears from the system quickly (days) without organ toxicity. However, radioactive photosensitizer such as the 124I-labeled analog 2 (superior to 18F-FDG in PET-imaging of lung, brain, breast and pancreas tumors) with a T½ of 4.2 days could cause radiation damage to normal organs. Based on the observation of high uptake of PAA nanoparticles in liver and spleen (below) we postulated that saturating the organs with the non-toxic PAA nanoparticles before injecting the PET agent might reduce uptake and radiation damage by 124I-imaging agent. For proof-of principle blank PAA nanoparticles were first injected (i.v.) into mice bearing Colon26 tumors followed 24 h later by i.v. 124I-analog (100-50 µCi). The mice were imaged at 24, 48 and 72 h post injection and biodistribution studies were performed at each time point summarized in FIGS. 8A-8C (only 72 h images shown).

Figure 9:
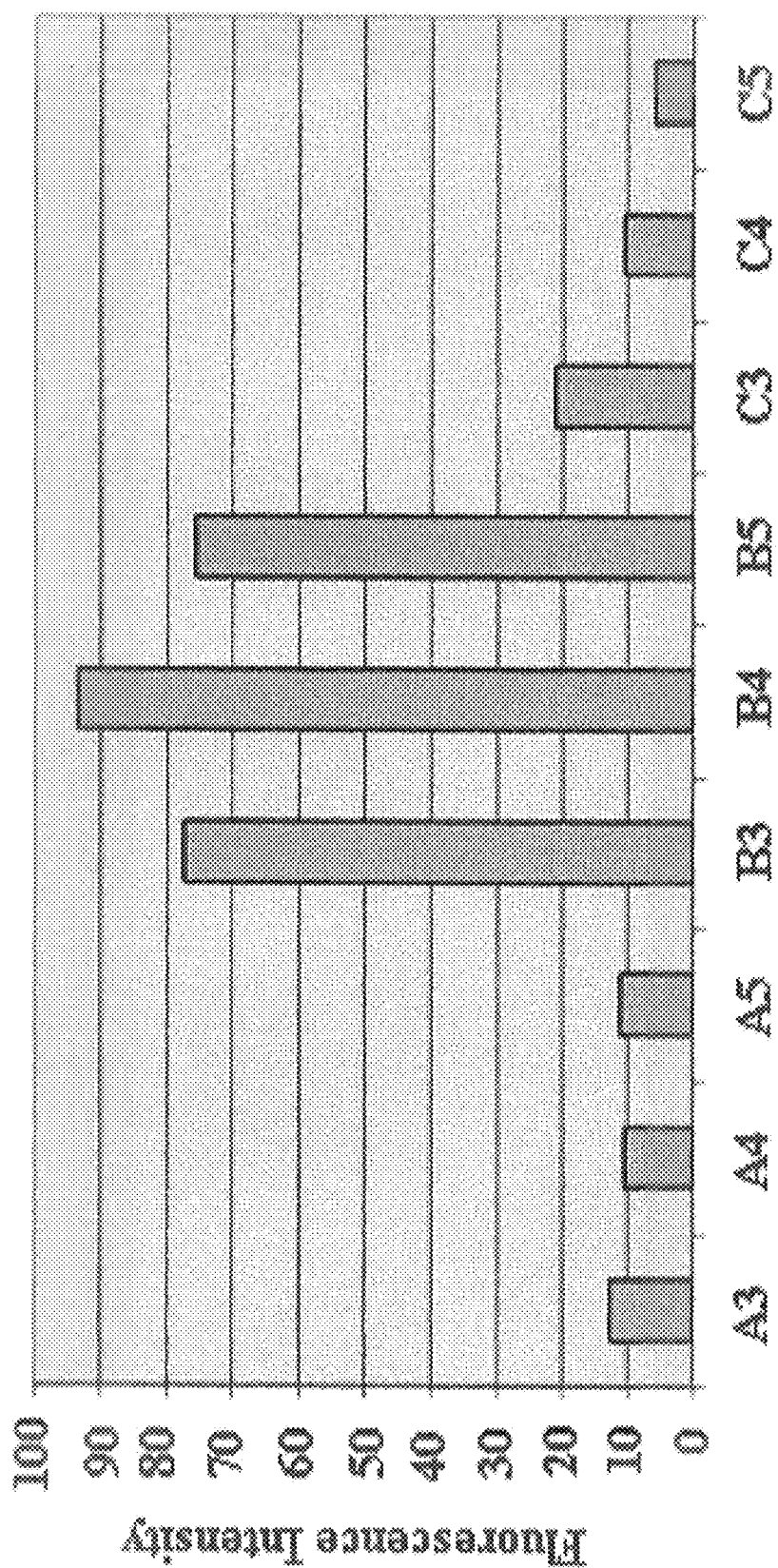
FIG. 9. Fluorescence intensity of cells targeted by F3-targeted (A series), F3-Cys targeted (B series) and nontargeted NPs (F series) in nucleolin rich MDA-MB-435 cell lines.

The presence of PAA nanoparticles made a remarkable difference in tumor contrast with brain, lung and pancreatic tumors). See FIG. 7 for comparative biodistribution. PAA nanoparticles can be targeted to nucleolin with F3-Cys:

F3-targeted nanoparticles were prepared using two kinds of F3 peptides: F3 peptide conjugated to nanoparticle via one of the 8 lysines available in its sequence and F3-Cys peptide conjugated to nanoparticle via cysteine. Cysteine capped nanoparticles served as non-targeted control. Three 25 mg batches of each type of nanoparticle contained: 2.6, 5.1 and 7.7 mg F3, (A3-A5) respectively; 2.7, 5.3 and 8 mg F3-Cys (B3-B5) respectively, and 0.29, 0.58 and 0.87 mg Cys (C3-C5) respectively. The fluorescence intensity from PAA nanoparticle incubated in vitro with nucleolin positive MDA-MB-435 cells is shown in FIG. 9. The F3-Cys conjugated nanoparticles show considerably higher binding efficiency than non-targeted nanoparticles, while F3 conjugated nanoparticles do not. Conjugation via a cysteine link preserves the specificity of F3 peptide for nucleolin. In addition excess cysteine on the nanoparticles helphotosensitizer to minimize the non-specific binding. Additional experiments (not shown) suggested that the amount of F3-Cys peptide (5.3 mg/25 mg nanoparticle) used for B4 nanoparticles was optimal.

Optical properties of post-loaded PAA nanoparticles. The absorption spectrum of PAA nanoparticles post-loaded with both HPPH and cyanine dye (even at 0.5 mg/ml), clearly shows characteristic signatures for both the photosensitizer and dye, without aggregation-induced broadening, while the fluorescence spectrum shows strong signals from both components.

Figure 11:
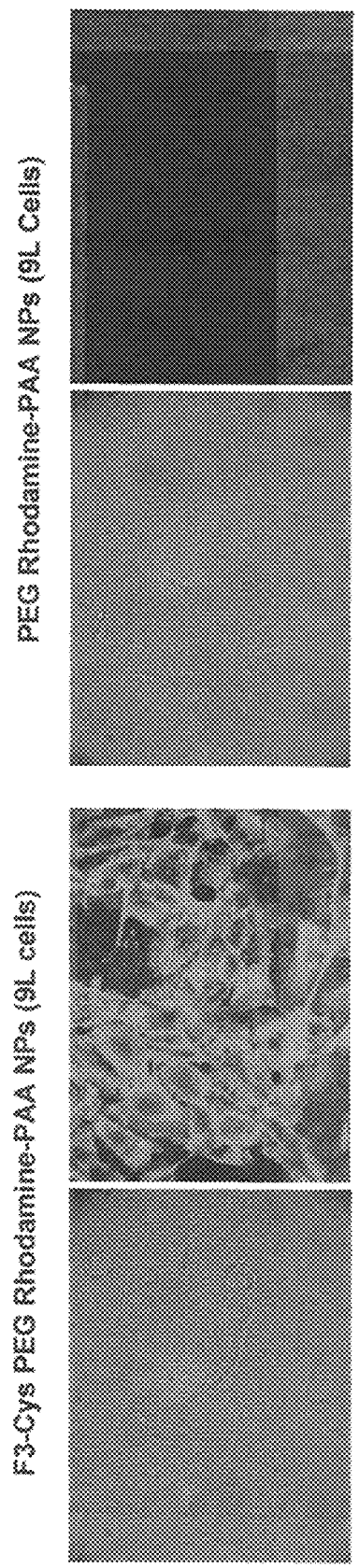
FIG. 11. Confocal images showing the target-specificity of F3-Cys peptide in 9 L Glioma tumor cells. Left: F3-Cys PEG Rhodamine-PAA NPs (9 L cells). Right: PEG Rhodamine-PAA NPs (9 L Cells)

HPPH Conjugated PAA Nanoparticles with F3-Cys Peptide at the Outer Surface Show Targeted Specificity:

F3-mediated specificity is retained in the presence of conjugated HPPH. F3 targeted nanoparticles did targeted nanoparticles did not, indicating that F3-mediated specificity is retained in the presence of conjugated HPPH. F3 targeted nanoparticles did not accumulate in the nucleus. On activation of cells with light at 660 nm only F3-targeted nanoparticle caused cell kill (FIG. 11). Cell internalization of F3-targeted nanoparticles was confirmed by fluorescence confocal microscopy.

Figure 10:
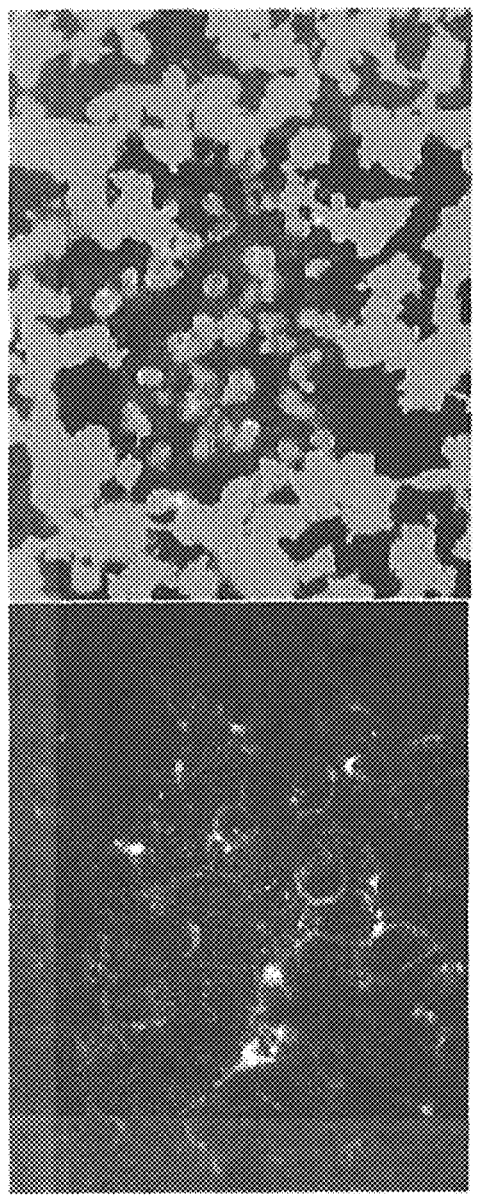
FIG. 10. Fluorescence (left) & Live/dead cell assay (right) of HPPH conjugated PAA NPs+ or −F3-Cys peptide incubated for 15 min with MDA-MB-435 cells.
Figure 10:
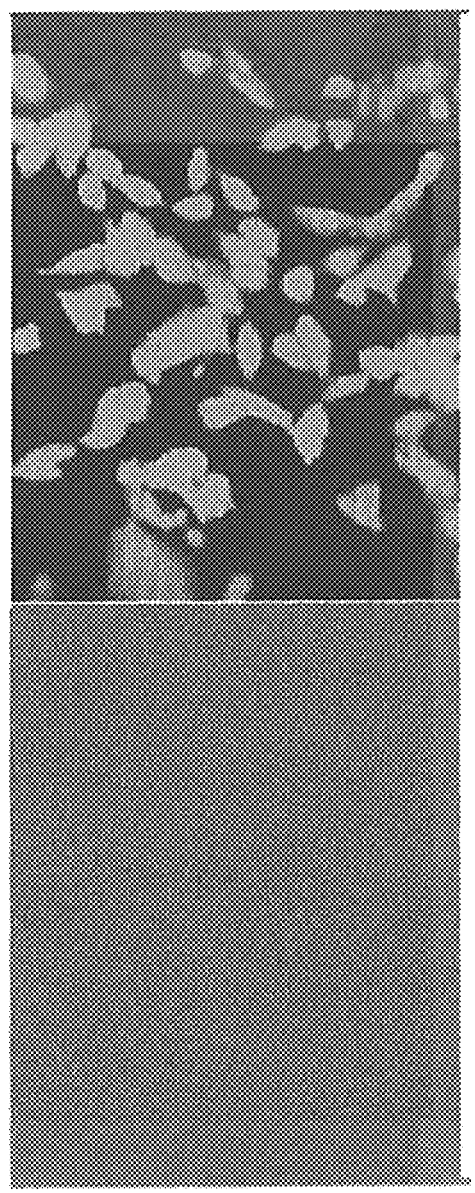

HPPH Conjugated PAA Nanoparticles with F3-Cyspeptide at the Outer Surface Show Targeted Specificity:

The specificity of targeted nanoparticles was tested by fluorescent imaging (FIG. 10). F3 targeted HPPH conjugated PAA nanoparticle specifically bound to MDA-MB-435 cells (expressing nucleolin) while non-targeted nanoparticles did not, indicating that F3-mediated specificity is retained in the presence of conjugated HPPH. F3 targeted nanoparticles did not accumulate in the nucleus. On activation of cells with light at 660 nm only F3-targeted nanoparticle caused cell kill (FIG. 11). Cell internalization of F3-targeted nanoparticles was confirmed by fluorescence confocal microscopy.

F3-Cys Shows Target-Specificity in 9 L Glioma Cells:

Similar to F3-cys, a pegylated form of F3-Cys PEG on PAA nanoparticles also showed remarkable target-specificity in 9 L rat glioma cells which also expresses nucleolin, FIG. 11. (Note: HPPH is replaced with a Rhodamine moiety).

Figure 12:
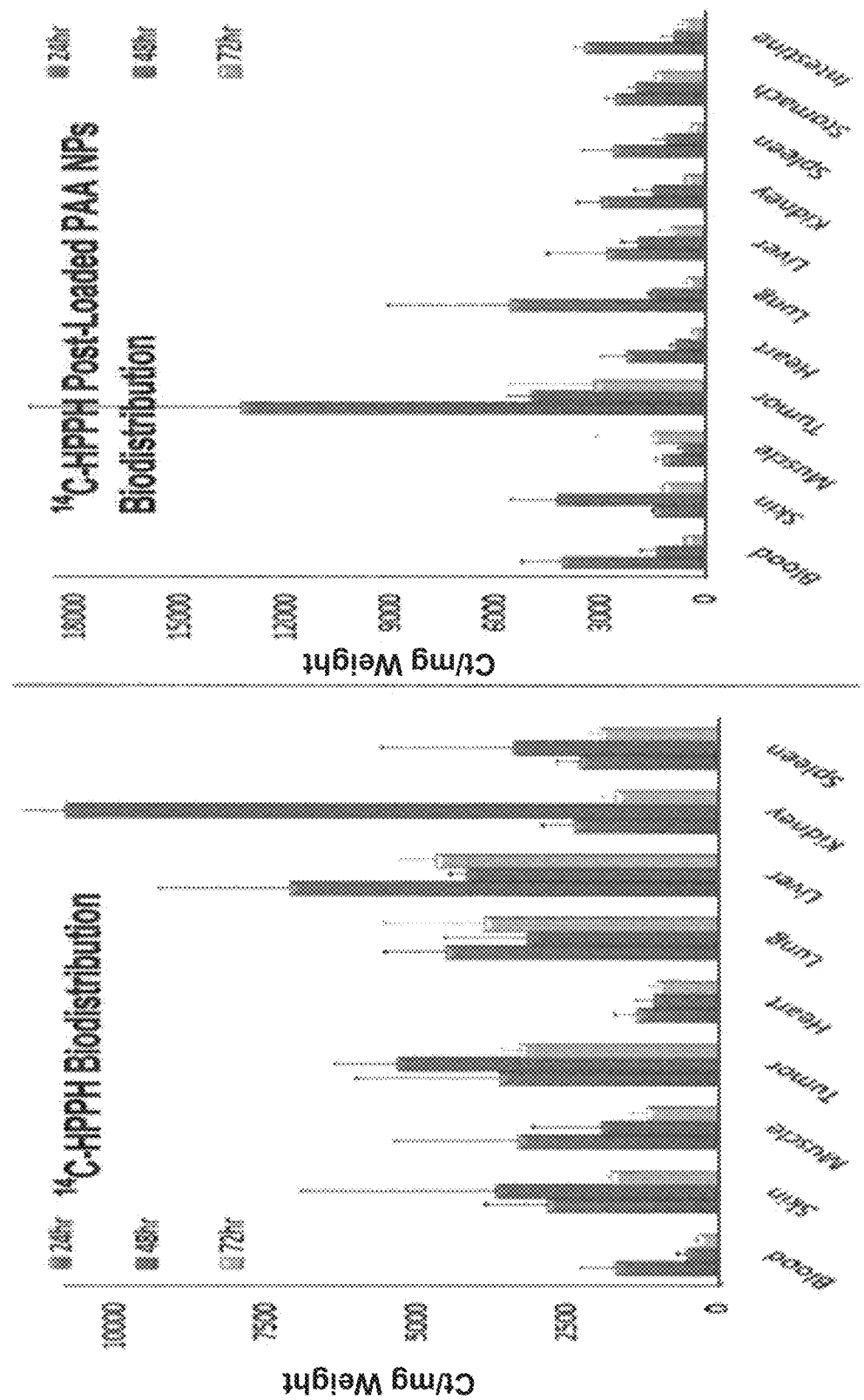
FIG. 12. In vivo biodistribution of 14C-labeled HPPH, and 14C-labeled HPPH post-loaded into PAA NPs in BALB/c mice bearing Colon26 tumors. 14C-labeled PS (3.8 µCi/0.2 mL) were administered to 12 mice/group. At 24, 48, 72 h after injection, three mice/time-point were sacrificed. The organs of interest were removed and the radioactivity was measured. The raw data were converted to counts/gram of tissue.

Biodistribution Studies: PAA Nanoparticle Enhances Tumor Uptake of HPPH:

The biodistbiodistribution of 14C-HPPH and 14C-HPPH post-loaded PAA nanoparticle was performed in BALB/c mice bearing Colon26 tumors at 24, 48 and 72 h post injection (3 mice/time point) and the results are summarized in FIG. 12. As can be seen presence of PAA nanoparticles made a significant increase in tumor uptake with reduced uptake in other organs.

Figure 13A:
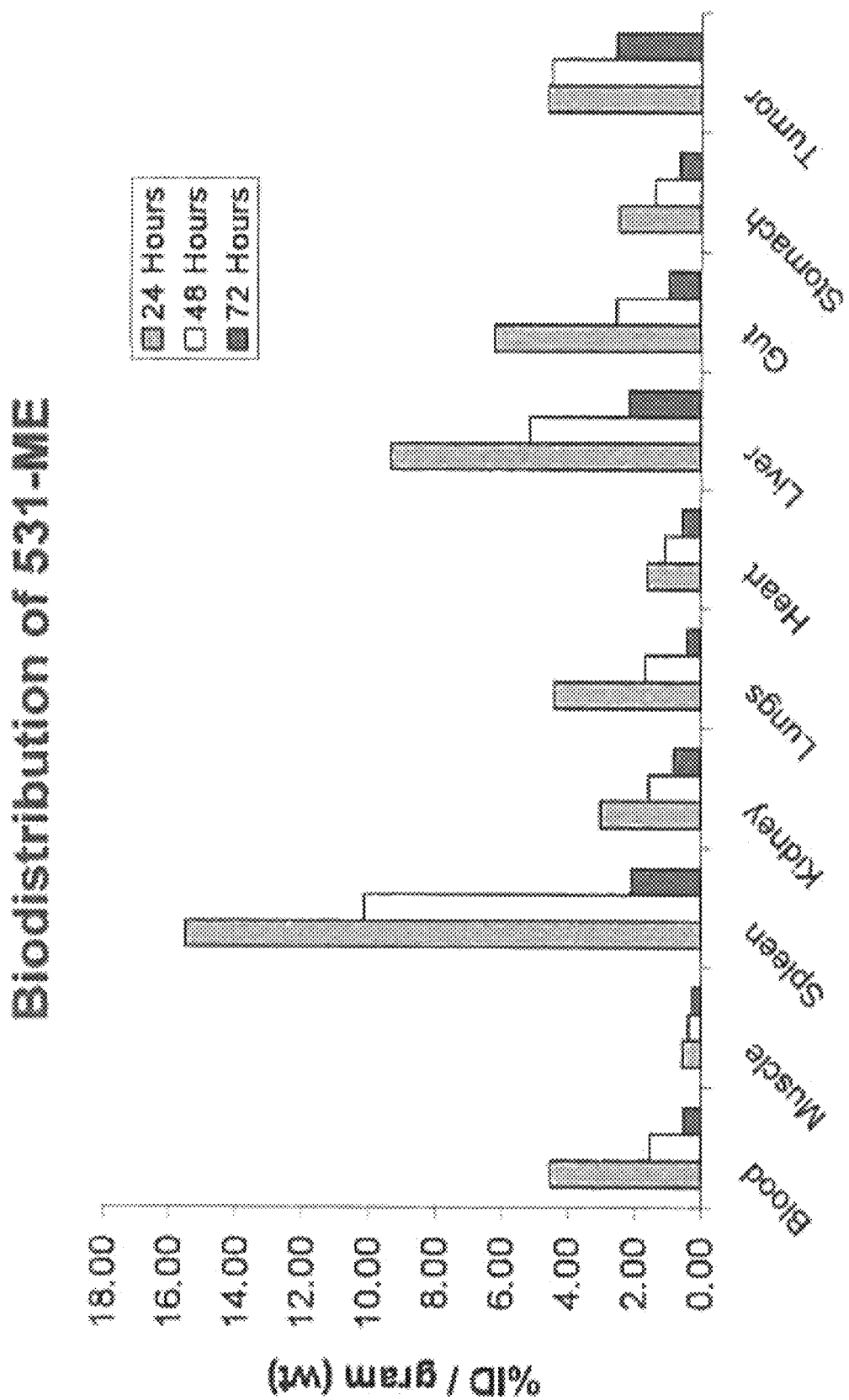
FIG. 13A shows In vivo biodistribution of iodinated photosensitizer at 24, 48 and 72 h post injection
Figure 13B:
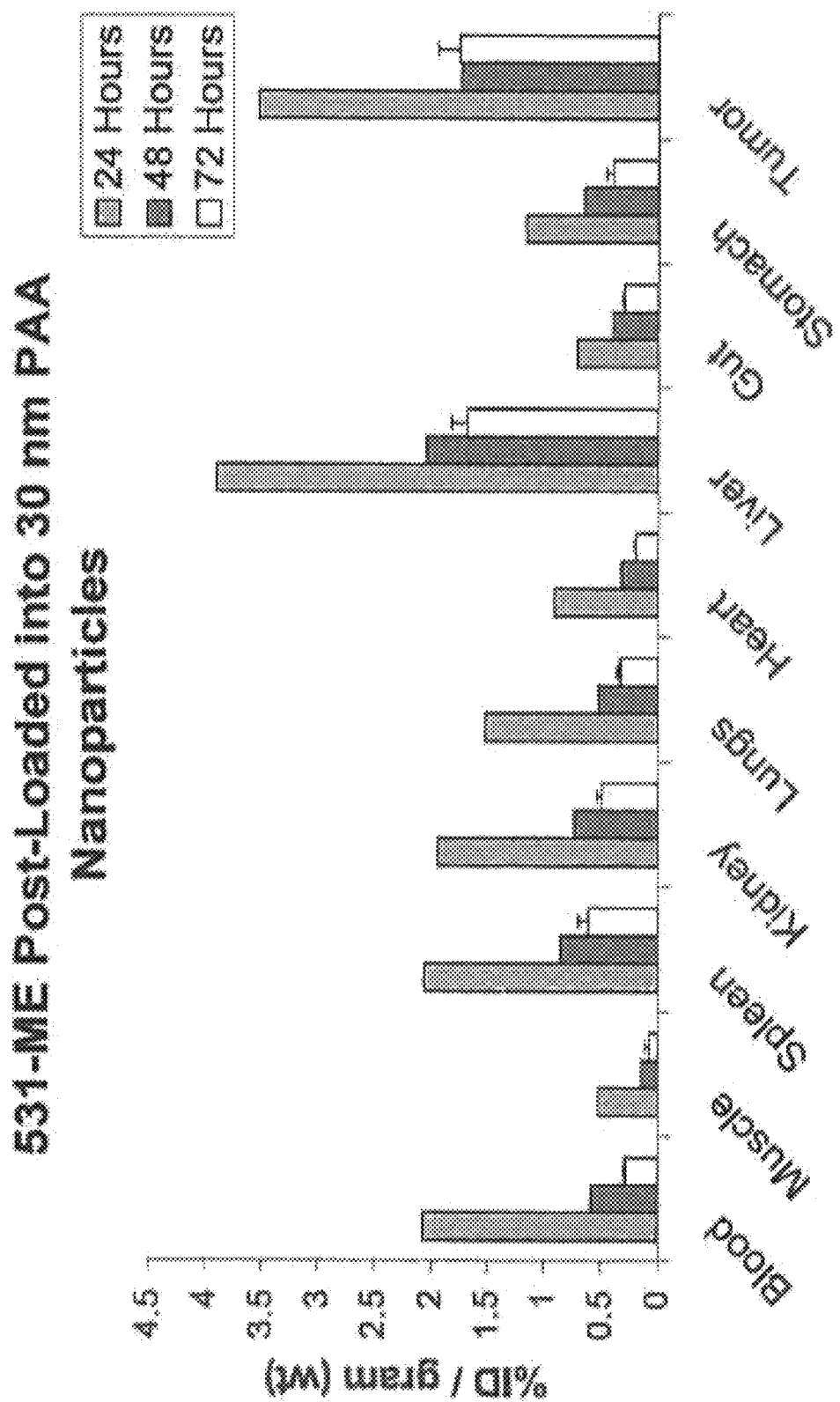
FIG. 13B shows In vivo biodistribution of iodinated photosensitizer using variable sizes of PAA NPs at 24, 48 and 72 h post injection 531-ME Post-Loaded into 30 nm PAA Nanoparticles.
Figure 13C:
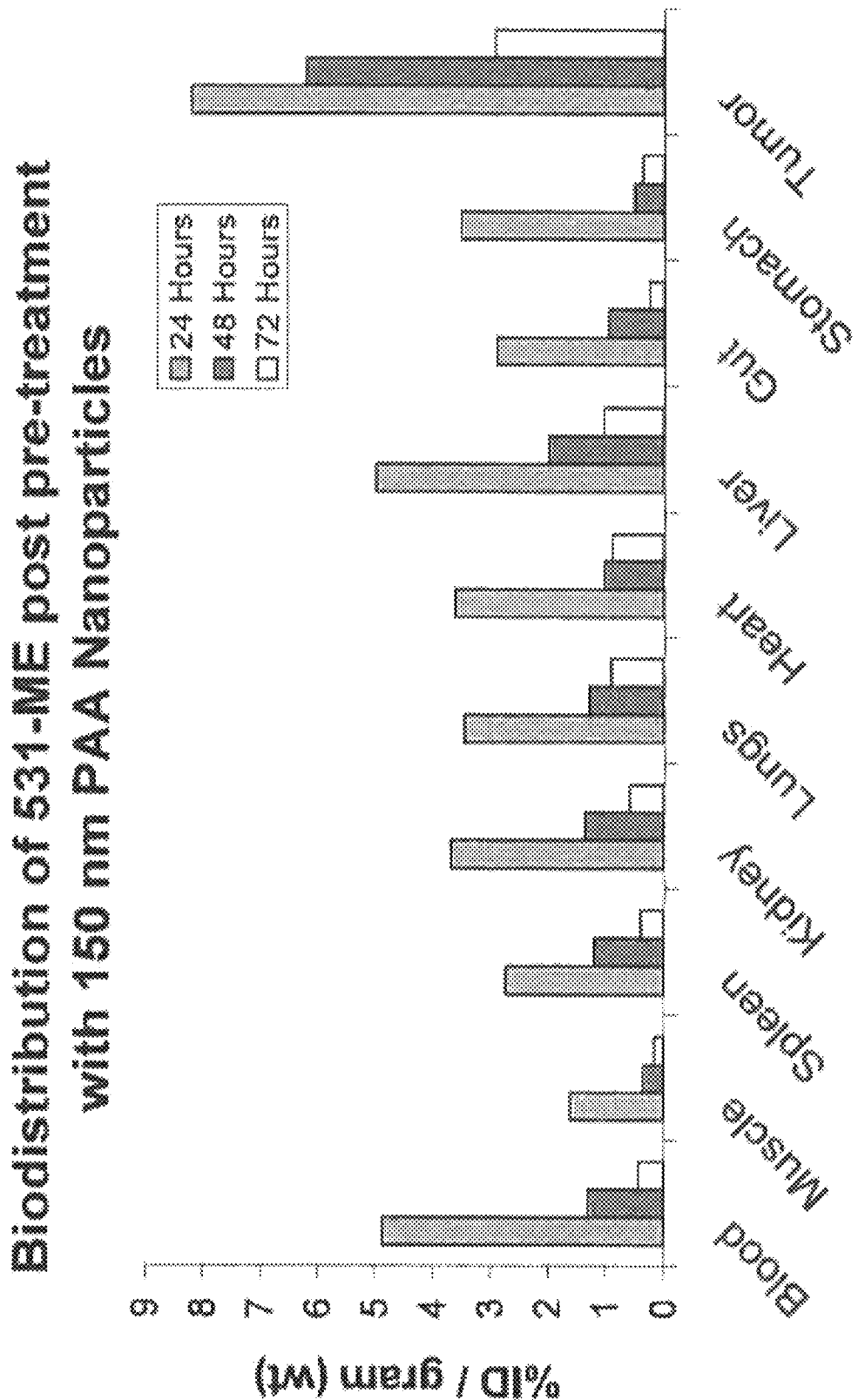
FIG. 13C shows In vivo biodistribution of iodinated photosensitizer using variable sizes of PAA NPs at 24, 48 and 72 h post injection 531-ME Post-Loaded into 150 nm PAA Nanoparticles.
Figure 14:
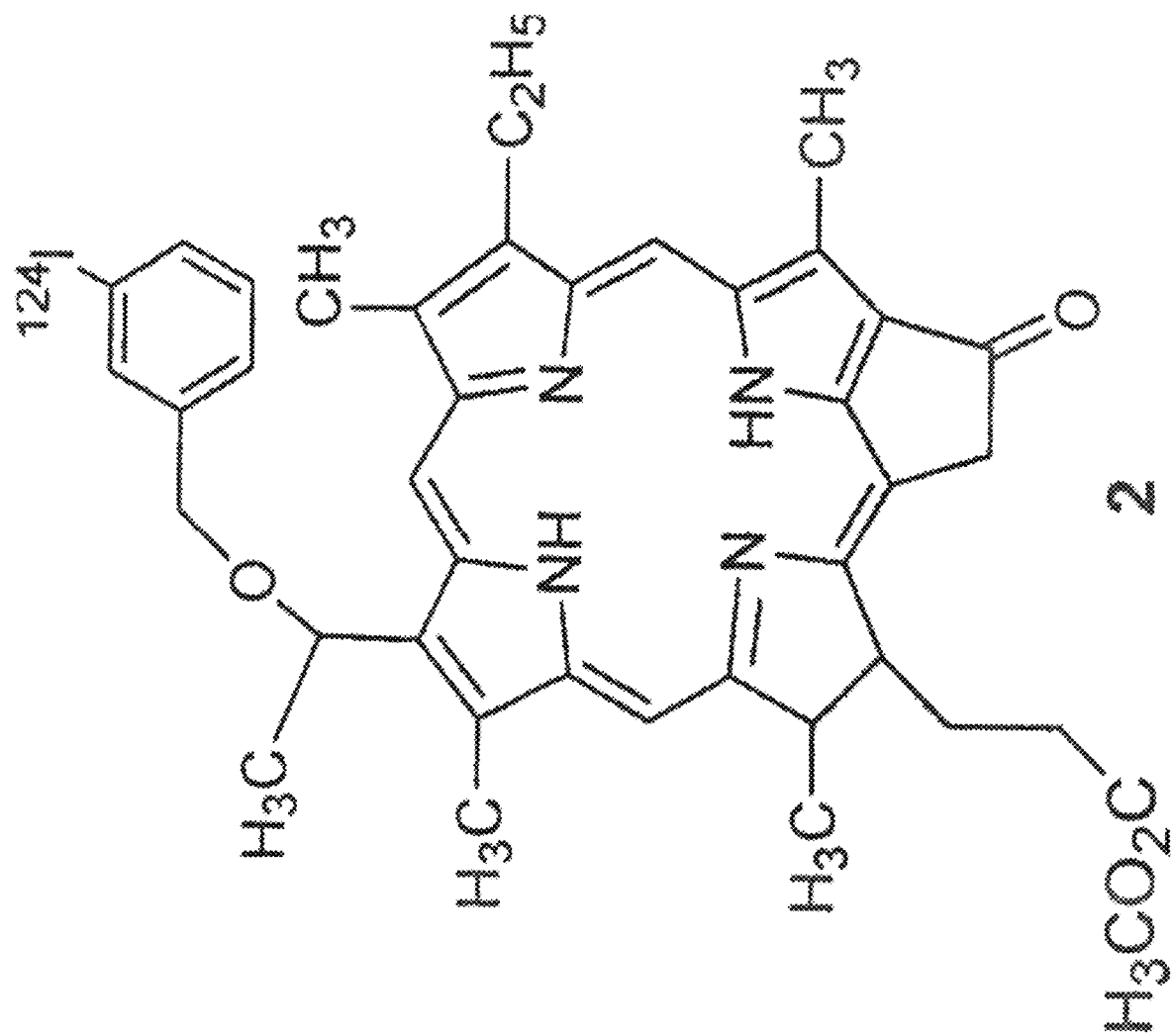
FIG. 14 shows the structural formula of HPPH.
Figure 15:
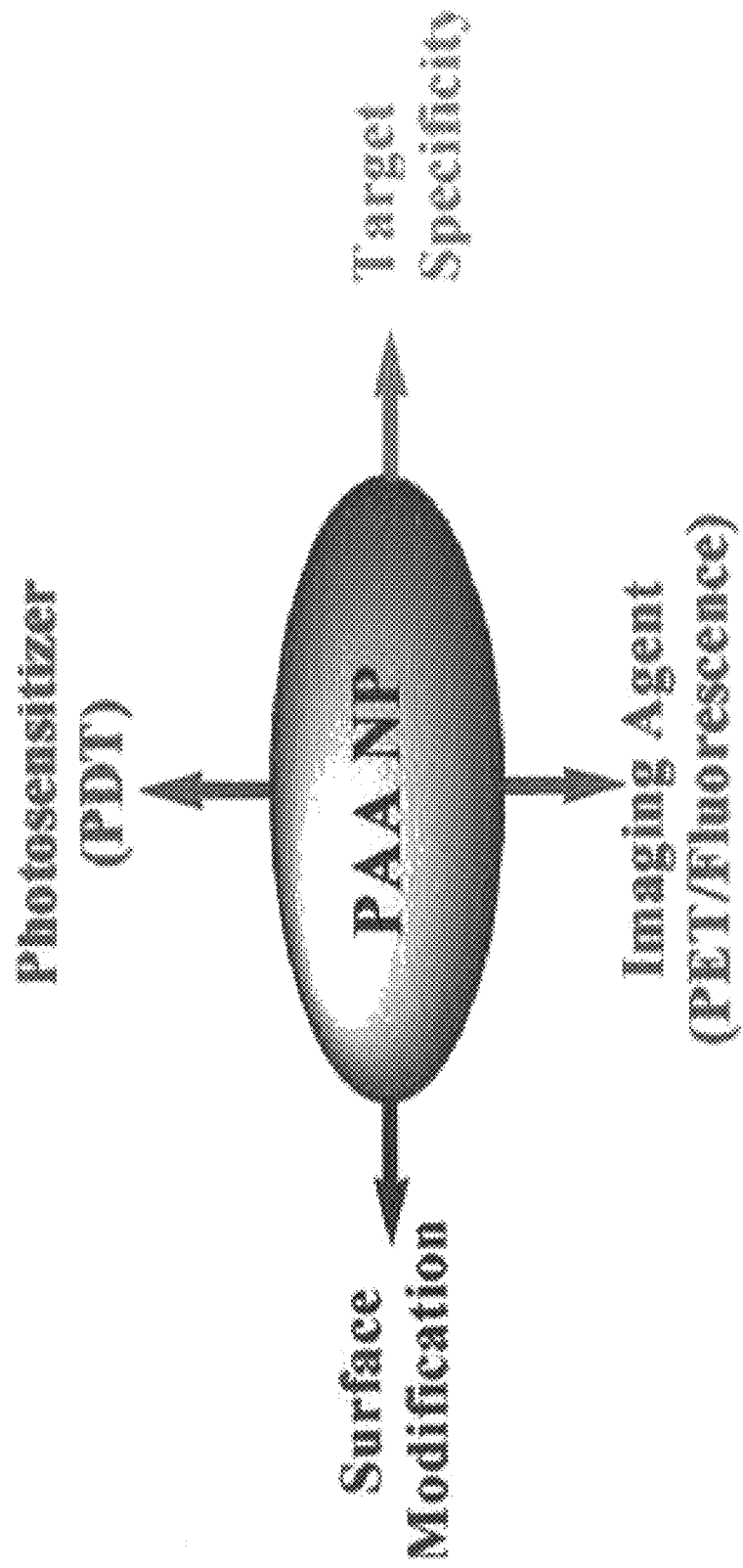
FIG. 15 is a diagram of Multifunctional PAA Nanoparticles.
Figure 16:
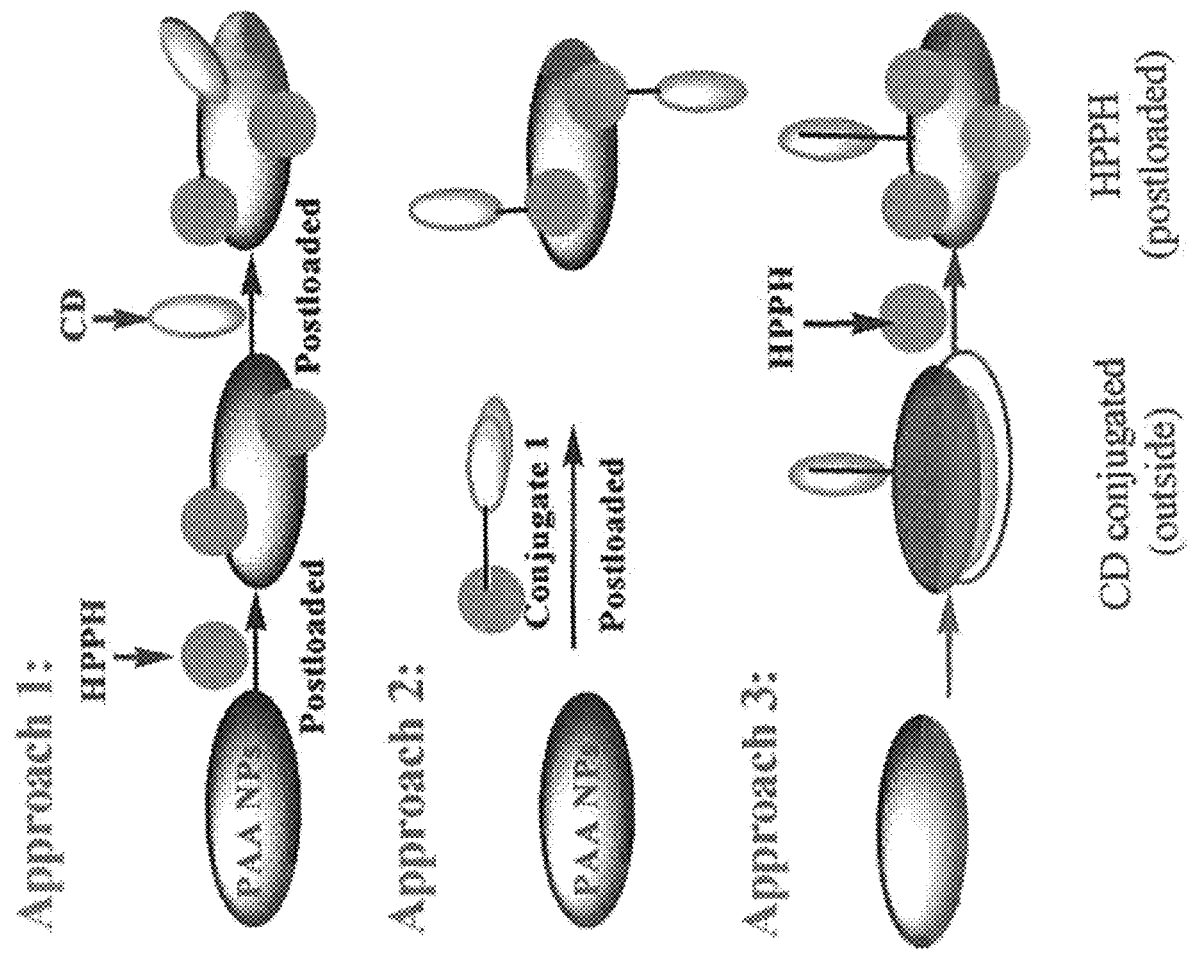
FIG. 16 shows flow diagrams for preparation of post-loaded nanoparticles.

Size of PAA Nanoparticles Made Remarkable Difference in Tumor-Enhancement:

The biodistribution of 124I-photosensitizer was investigated using variable sizes of nanoparticles either injecting the nanoparticles first and then administrating the labeled photosensitizer or postloading the labeled photosensitizer to PAA nanoparticles and then perform in vivo biodistribution in mice at 24, 48 and 72 h. The results summarized in FIGS. 13A-13C clearly indicate that the size of PAA nanoparticles makes a significant impact in tumor enhancement. Experiments related to in vivo PDT efficacy of these formulations are currently in progress.

This invention shows the utility of porphyrin-based compounds in a "bifunctional agent" for imaging breast tumor and tumor metastasis. Similar to most nanoparticles, PAA nanoparticle accumulate in liver and spleen. Their clearance rate from most organs is significantly faster than Ormosil nanoparticle and they do not show long-term organ toxicity. Even tumor-avid porphyrin based photosensitizer exhibit high uptake in liver and spleen, but are non-toxic until exposed to light. The photosensitizer clear from the system quickly (days) without organ toxicity. However, radioactive photosensitizer such as the 124I-labeled analog 2 (superior to 18F-FDG in PET-imaging of lung, brain, breast and pancreas tumors) with a T½ of 4.2 days could cause radiation damage to normal organs. Based on the observation of high uptake of PAA nanoparticles in liver and spleen (below) we postulated that saturating the organs with the non-toxic PAA nanoparticles before injecting the PET agent might reduce uptake and radiation damage by 124I-imaging agent. For proof-of principle blank PAA nanoparticles were first injected (i.v.) into mice bearing Colon26 tumors followed 24 h later by i.v. 124I-analog (100-150 µCi). The mice were imaged at 24, 48 and 72 h post injection and biodistribution studies were performed at each time point summarized in FIGS. 8A-8C (only 72 h images shown).

The presence of PAA nanoparticles makes a remarkable difference in tumor contrast with significantly reduced uptake in spleen and liver and improved tumor-uptake/contrast at 24, 48 and 72 h post injection (3 mice/group Similar studies (tumor-imaging and PDT efficacy) in which the labeled photosensitizer is post-loaded to variable sizes. Similar studies (tumor-imaging and PDT efficacy) in which the labeled photosensitizer is post-loaded to variable sizes PAA nanoparticles are currently in progress.

Importantly, according to the present invention, we compared the photosensitizing and NIR fluorescence imaging potential of several biodegradable PAA nanoparticle formulations, in which the HPPH and CD moieties were post-loaded at a 2 to 1 and a 4 to 1 ratio, respectively. These formulations were significantly different in tumor uptake, in pharmacokinetics and in in vivo imaging and PDT efficacy.

Additional examples and details associated with the post-loading of both the photosensitizer and fluorescent imaging compound are as follows:

Human Serum Albumin, Tween-80 and dimethyl sulfoxide (DMSO) were purchased from Sigma-Aldrich. Bovine Calf Serum (BCS) was purchased and dPBS (pH 7.4, 1×, without calcium and magnesium) were purchased from Cellgro. Ethanol (200 proof) was purchased from Pharmco-Aaper. All solutions were prepared with 18 MΩ water purified by a Millipore Milli-Q Advantage A10 water purification system. 30 and 100 kDa Amicon Ultra-15 and Ultra 4 centrifuge filters were purchased from Fisher Scientific. Animal Studies all Animal Studies were Performed Following the Animal Protocol Guidelines Approved by Institutional Animal Care and Use Committee (IACUC).

The PAA nanoparticles were prepared by following our previous with slight modifications (See e.g. Multifunctional ORMOSIL and PAA nanoparticles, Gupta et al., Photodynamic Therapy Back to the Future. Edited by Kessel, David H. Proceedings of the SPIE, Volume 7380 (2009), pp. 73805H-73805H-12 (2009).

Post-Loading of the Photosensitizer 1, and the cyanine dyes 2, and 3 to blank AFPAA to create nanoconstructs 4, 5, 6, 9, and 10: In brief, 10 mg of lyophilized PAA NPs were suspended in 1 mL of 1% Tween-80/water solution and to this solution 10 μL of 1, 2, or 3 (20 mM in DMSO) is added and magnetically stirred at a constant rpm for 2 hours. The NPs were centrifuge filtered in a 30 kDa Amicon Ultra-15 centrifuge filter for 30 minutes at 5,000 RPM and then the NPs were reconstituted with water. The nanoparticles were syringe filtered with a 0.2 μm regenerated cellulose syringe filter. Nanoformulation 9 and 10 were created by mixing nanoconstruct 1 and 3 such that the molar ratio of 1 to 3 was 2:1 and 4:1, respectively. The NPs are stored at 4° C. until further use. For details see "Supporting Material Information".

Post-Loading of the photosensitizer 1 and the cyanine dye 3 to blank AFPAA to create nanoconstructs 7 and 8: Upon measuring the concentration of PS 1 in nanoconstruct 6, cyanine dye 3 in DMSO (20 mM) was added such that the molar ratio of PS 1 to cyanine dye 3 was either 2:1 or 4:1. Once cyanine dye 3 was added, the procedure is the same as for post-loading, PS 1 or cyanine dye 2 and 3. For detailed procedure see the "Supporting Material Information".

Release Kinetics Procedure: The in vitro release profile of the photosensitizer 1, and the cyanine dye 3 in nanoconstructs/formulations 5-10 was measured. The NPs from all formulations were suspended in a 1% human serum albumin (HSA)—water solution and immediately the absorbance value for the HSA/nanoconstruct solution was measured spectrophotometrically. To measure the release of the photosensitizer 1 and/or the cyanine dye 3 from the NP, the NP solution is centrifuge filtered in a 100 kDa Amicon ultra-4 centrifugation filter for 20 minutes at 4,000 RPM. The absorbance of the PS or fluorophore in the filtrate was spectrophometically measured (filtrate 1). The NPs in the retentate were reconstituted to the original volume with 1% HSA and re-centrifuge filtered (filtrate 2) and measured spectrophotometrically. The amount of 1 and/or 3 retained by the NP was confirmed by measuring the absorbance of the retentate upon reconstitution to the original volume with 1% HSA. If the sum total of all filtrates and the retentate is less than 90% of the stock value for either chromophore then ethanol is added to the centrifuge filter to measure what had adsorbed to the filter. These measurements were taken immediately post-addition of the nanoconstructs in a 1% HSA solution, 4 and 24 hours post addition of the nanoconstructs in the 1% HSA solution. Additionally, the release of PS 1 and cyanine dye 3 in nanoconstruct 7 was measured in 25% bovine calf serum (BCS) at 37° C. The procedure followed for the release of the PS/fluorophore in 25% BCS was similar to that of 1% HSA, except that the measurements were taken at 4, 8, 12, and 24 h post-addition of nanoconstruct 7.

Optical Imaging Setup:

The fluorescence imaging was conducted in accordance with a protocol approved by the Institutional Animal Care and Use Committee IACUC at Roswell Park Cancer Institute and the Guide for the Use of Laboratory Animals. BALB/c mice (3 mice/group) bearing subcutaneous Colon 26 tumors on the right shoulder were injected i. v. (tail-vein) with either cyanine dyes or nanoconstructs/formulations. For a detailed description of the groups of mice imaged along with the dose, see the "Supporting Material Information".

Absorbance, Fluorescence, and Singlet Oxygen Measurements:

The absorbance measurements were performed on a Varian Cary-50 Bio UV-Visible spectrophotometer. The concentrations of the NP formulations were measured in ethanol utilizing 47,500, 200,000 and 207,455 L mol$^{-1}$ cm$^{-1}$ as the respective molar extinction coefficients of 1, 2, and 3.

A SPEX 270M spectrometer (Jobin Yvon) was used for acquisition of fluorescence emission spectra in the far red and NIR spectral ranges, utilizing the first output port equipped with an InGaAs photodetector (Electrooptical Systems Inc., USA). A diode-pumped solid-state laser (Verdi, Coherent) at 532 nm was the excitation source. Generation of singlet oxygen ($^1O_2$) was detected by its phosphorescence emission peaked at 1270 nm. The decays of this emission were acquired using the Infinium oscilloscope (Hewlett-Packard) coupled to the output of the Hamamatsu IR-PMT which is attached to the second output port of the SPEX 270M spectrometer. Nanoconstructs 5-8 in polystyrene cuvettes were placed in front of the entrance to the spectrometer. The emission signal was collected at 90-degrees relative to the exciting laser beam with the use of additional long-pass filters (a 950LP filter and/or a 538AELP filter) to attenuate the scattered light and fluorescence from the samples. A second harmonic (532 nm) from the nanosecond pulsed Nd:YAG laser (Lotis TII, Belarus) operating at 20 Hz was used as the excitation source for time-resolved measurements.

In-Vivo Photodynamic Therapy:

Eight- to twelve-week-old BALB/cAnNCr mice (Jackson Laboratory, Bar Harbor, Me.) were inoculated subcutaneously (s.c.) with 1×10$^6$ Colon 26 cells. When tumors reached 40-70 mm$^3$, mice were injected i.v. (tail vein) with PS 1 (formulated in 1% Tween 80/D5W) or PAA nanoconstructs/formulations 6-10 suspended in water and further diluted in D5W. 24 hours post i.v. injection (dose of PS 1: 0.47 mol/kg), mice (BALB/c mice bearing Colon 26 tumors, 10 mice/group) were restrained in plexiglass holders and tumors were irradiated at 665 nm with a fluence and fluence rate of 135 J/cm$^2$ at 75 mW/cm$^2$, respectively, using a pumped argon-dye laser. The growth of tumors was measured two to three times per week and the mice were monitored for a total of 60 days post PDT treatment. When the tumor regrowth was >400 mm$^3$, the mice were euthanized according to the guidelines of the institute approved animal protocol.

Preparation of HPPH and Near Infrared Cyanine Dye Post-Loaded PAA NPs.

In an ongoing SAR study with a series of cyanine dyes (CD), we modified IR820 2 with limited imaging potential to a highly avid CD 3 in which the chloro-group of IR820 was replaced with a p-aminothiol functionality. CD 3 formulated in 1% Tween 80/5% dextrose was tumor avid, but the corresponding PAA formulation produced enhanced tumor contrast. On the other hand PS 1 (HPPH) and nanoconstruct 6 showed similar PDT efficacy with 40% tumor cure at a dose of 0.47 mol/kg. Although the PAA formulation did not enhance the PDT efficacy at similar treatment parameters, it did show a markedly improved tumor-specificity (determined by fluorescence imaging).[23] Our objective was to prepare a single platform for imaging and therapy, therefore we investigated a synthetic approach in which the PS 1 was conjugated with 3. The resulting product showed excellent tumor-imaging ability (dose: 0.3 mol/kg), but the therapeutic dose was 8- to 10-fold higher. The low activity of the conjugate could be due to a part of the singlet oxygen produced by exposing the tumors with light was quenched by the CD, which reduced its activity and thus required a higher dose of the agent (HPPH-CD) for achieving efficacy similar to PS(HPPH) 1. HPPH-CD conjugate also exhibited significant FRET, which indirectly correlates to singlet oxygen production, a key cytotoxic agent for PDT. In other words molecules with higher FRET should show reduced singlet oxygen production and PDT efficacy.

Therefore, for our present study we were interested in preparing a series of multifunctional PAA nanoplatforms in which the PS and the CD molecules are post-loaded together in variable ratios or separately post-loaded (FIG. 17B, nanoconstructs 4-10) and to investigate their tumor imaging and therapeutic potential. We anticipated that among all the nanoconstructs, the nanoformulation 10 in which PS and CD were separately post-loaded and then mixed in a ratio of 4 to 1 may show enhanced PDT response due to lower singlet oxygen quenching probability by the cyanine dye or the energy transfer between the two chromophores (PS and CD) which could result in higher singlet oxygen production and improved long term tumor cure.

Figure 17A:
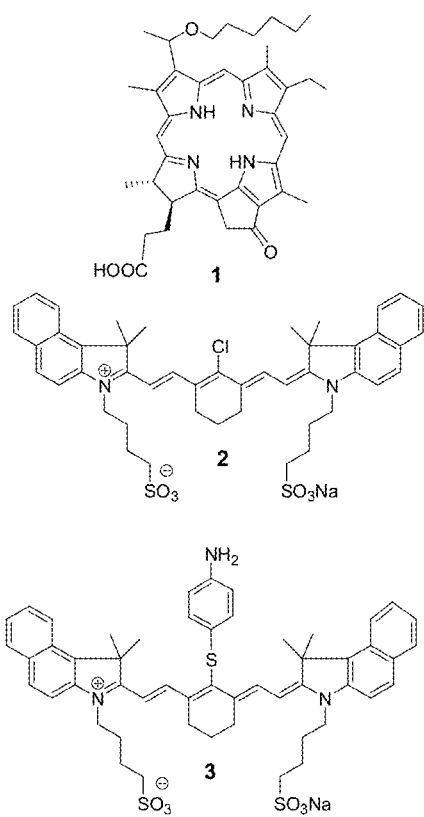
FIG. 17A shows structural formulas for HPPH at 1, IR820 cyanine dye (CD) at 2 and cyanine dye at 3 where the chloro group of IR820 is replaced with p-aminothiol.
Figure 17B:
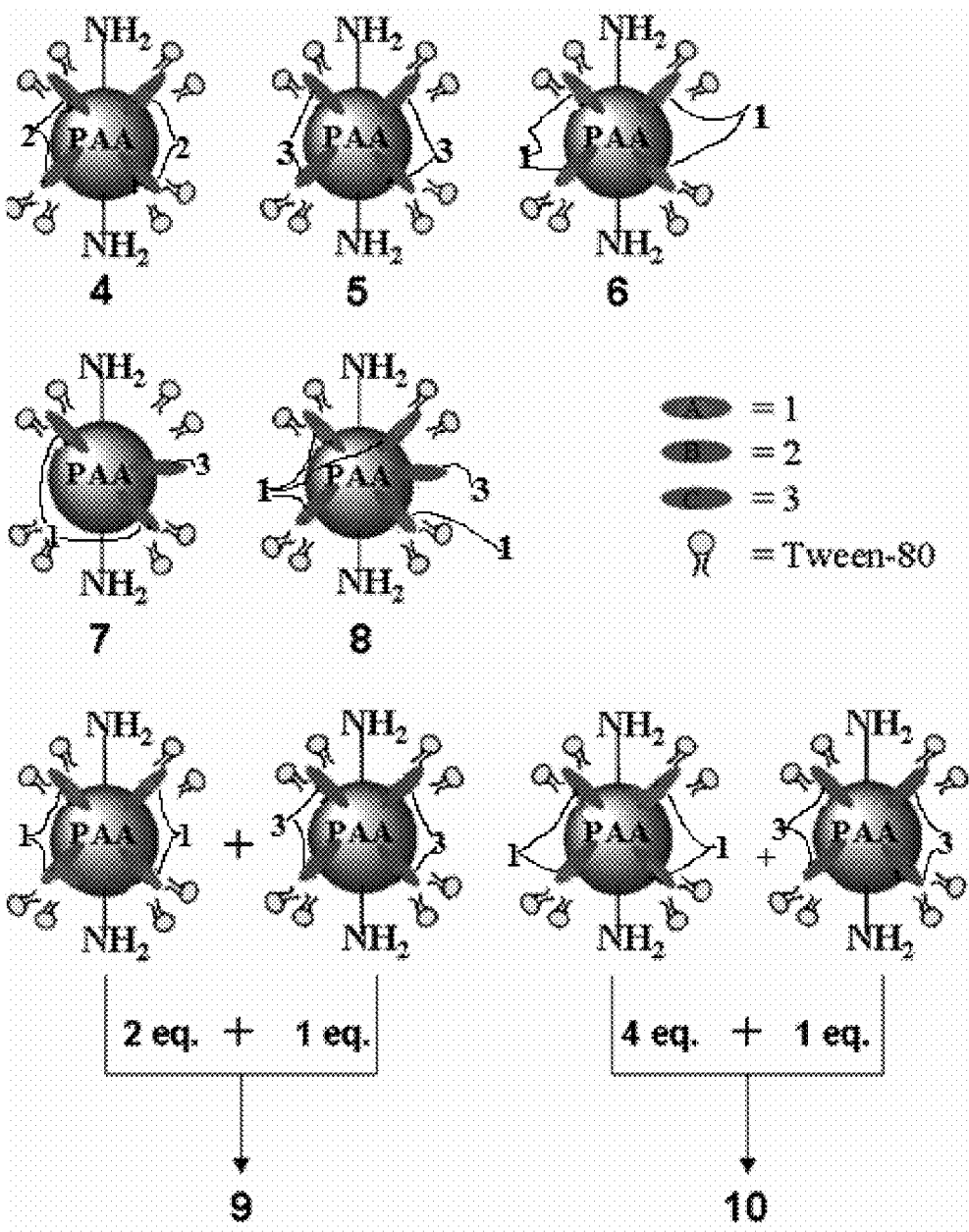
FIG. 17B illustrates various polyacrylamide (PAA) nanoparticles postloaded with HPPH(1), cyanine dye (2) and cyanine dye (3) alone and in different combinations and ratios.

See FIGS. 17A and 17B: Post-loading of amine functionalized PAA NPs with IR-820, cyanine dye 2, nanoconstruct 4; cyanine dye 3, nanoconstruct 5; HPPH, photosensitizer 1: nanoconstruct 6; photosensitizer 1 and cyanine dye 3 at a 2:1 molar ratio, nanoconstruct 7; and HPPH 1 and cyanine dye 3 at a 4:1 molar ratio, nanoconstruct 8. Nanoformulations 9 and 10 are nanoconstruct 6 and 5 mixed such that the molar ratio of 1 to 3 is 2:1 and 4:1, respectively.

To characterize the size and dispersity of the nanoparticles, dynamic light scattering (DLS) and scanning electron microscopy (SEM) was utilized. The DLS showed a mean diameter of 33.5, 32.5, and 35.2 nm for blank nanoparticles, nanoconstruct 6, 5, and 7. The SEM demonstrated that the NPs are uniform and monodisperse, with a mean diameter of ~25 nm (see supplemental).

For PDT, porous nanoparticles are advantageous since release of PS from the NP is not required for the singlet oxygen to diffuse into the tumor cells. However, if the release profile is rapid the NP may not be able to efficiently deliver a high payload of the desired agent to tumor. Therefore, we investigated the release profiles of the photosensitizer 1 and the cyanine dye 3 from nanoconstructs 5-10, respectively, by incubating them in 1% human serum albumin (HSA) at variable time points. The release profiles are summarized in the supplemental section. The release of PS 1 in nanoconstruct 6 showed a two-phase release, where an increase in the release was seen in the first four hours, which subsequently decreased during the following 20 hours. Compared to nanoconstructs 7-10, nanoconstruct 6 showed the highest retention of PS 1 (HPPH) over a 24 hour time period with approximately 87% being retained. When comparing the percentage of PS 1 retained (at the initial time point, time zero), upon addition of 1% HSA, the nanoconstruct 8 and 10 showed the highest retention (~84%) of the PS. To mimic the release of PS 1 and cyanine dye 3 from nanoconstruct 7 in vivo, the nanoformulation 7, which provided the best whole-body fluorescence imaging and PDT response, was also subjected for the release of both the chromophores in 25% bovine calf serum (BCS, 37° C.) at 4, 8, 12, and 24 hours post-addition. The maximum release (3.2%) for PS 1 occurred at 4 h time point, whereas for the cyanine dye 3, the maximum release (2.8%) was observed at 8 h time point. These results were interesting to show a slower release of both the cyanine dye and the PS under physiologically relevant conditions.

Fluorescence Imaging Ability of Various Formulations.

Figure 18A:
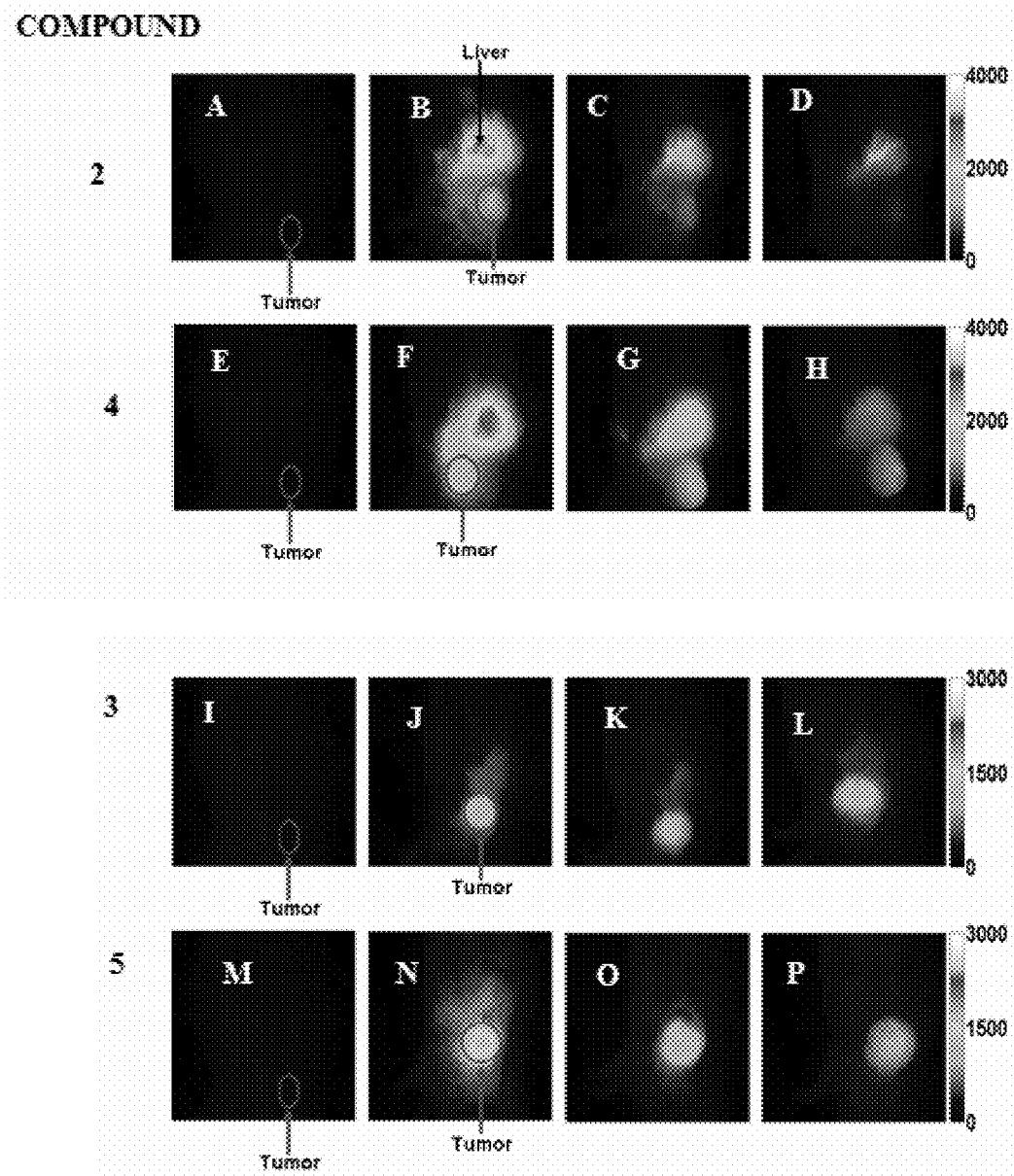
FIG. 18A shows whole body fluorescence images of BALB/c mice bearing Colon-26 tumors. Control mouse (A, E, I, and M), cyanine dye 2 (B-D), nanoconstruct 4 (F-H), cyanine dye 3 (J-L), nanoconstruct 5 (N-P), 24, 48, and 72 h post i.v. injection.
Figure 18B:
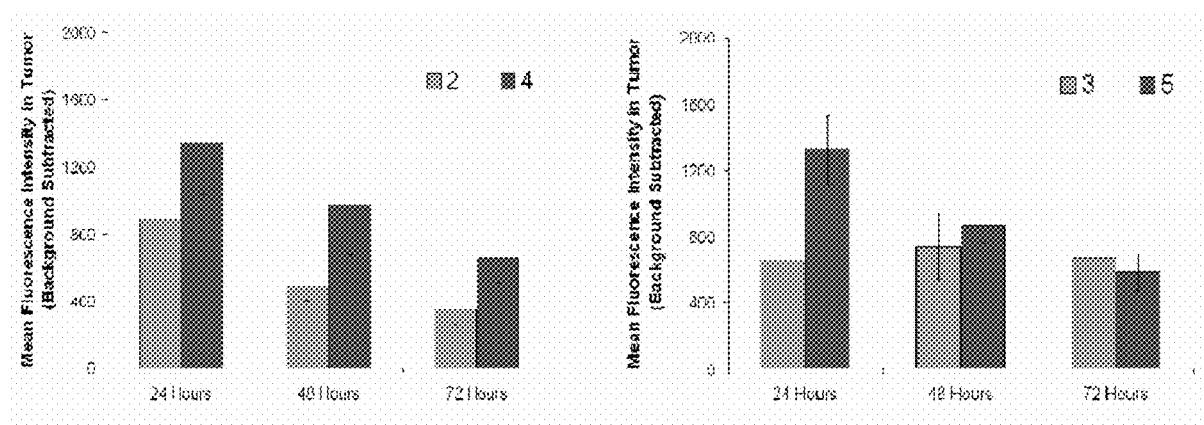
FIG. 18B shows fluorescence intensity values for left, cyanine dye 2 and construct 4 and right, cyanine dye 3 and construct 5.

To show that cyanine dye 2 (IR-820, Aldrich) has poor tumor selectivity, whole body fluorescence imaging of BALB/c mice bearing subcutaneous Colon 26 tumors was performed. FIG. 18A shows whole body fluorescence images of BALB/c mice bearing Colon-26 tumors. Control mouse (A, E, I, and M), cyanine dye 2 (B-D), nanoconstruct 4 (F-H), cyanine dye 3 (J-L), nanoconstruct 5 (N-P), 24, 48, and 72 h post i.v. injection. The fluorescence intensity values shown in FIG. 18B are background subtracted from the control mouse (left, cyanine dye 2 and construct 4 and right, cyanine dye 3 and construct 5), The error bar is the standard deviation of the mean fluorescence intensity in the tumors, n=3. *=statistical significance of the difference in mean fluorescence intensity (P<0.05, student t-test).

The water insoluble fluorophore 2 was formulated in a 1% Tween-80/5% dextrose solution and was injected i.v. at a dose of 0.3 μmole/kg. The mice were imaged at 24, 48, and 72 hours post-injection (FIG. 18A at B-D). Due to the rather poor tumor localization of 2, we post-loaded it into PAA NPs formulation 4 and compared their tumor uptake and fluorescence imaging abilities. The results summarized in FIG. 18B clearly indicate much improved tumor selectivity of the PAA NP formulation 4 over the free fluorophore 2. Under similar imaging parameters, modified cyanine dye 3 and the corresponding nanoconstruct 5 (cyanine dye 3 post-loaded to PAA NPs) were also imaged (FIG. 18A). As can be seen, compared to cyanine dye 2 (FIG. 18A), the modified version 3 showed higher uptake and improved tumor-imaging ability (FIG. 18A, J-L). Upon post-loading the cyanine dye 3 to PAA NPs, its uptake and tumor-imaging ability at 24, 48 and 72 hours post-injection was further enhanced (FIG. 18A at N-P) with the difference in intensity in the tumor for 5 being statistically higher (p<0.05) at 24 hours post-injection. We then decided to investigate further the utility of these biodegradable nanoparticles in developing a "multifunctional" nanoplatform. The fluorescence imaging of PAA nanoconstructs/formulations 7-10 in which HPPH 1 and cyanine dye 3 were post-loaded at a ratio of 2:1 and 4:1 (either in a single nanoparticle 7 and 8 or in separate nanoparticles 9 and 10), respectively, was investigated in BALB/c mice bearing Colon 26 tumors. On comparing the images obtained by using the cyanine dye 3 alone and the corresponding nanoconstructs 5, 7-10 the maximum accumulation in the tumor for 3 was observed at 48 h post injection FIG. 18A at K, whereas the nanoconstructs 5, 7 and 8 (FIGS. 19 and 20) produced the maximum tumor uptake at 24 h post-injection. This could be due to a significant difference in the pharmacokinetic characteristics of the products in two different formulations. In nanoconstructs 7 and 8 in which the PS and CD were post-loaded in a ratio of 2 to 1 and 4 to 1 on excitation of the cyanine dye at 782 nm gave fluorescence at 866 and 870 nm respectively. Interestingly, both nanoconstructs on in vivo excitation at 665 nm produced a significant fluorescence beyond 860 nm, which can be explained by the phenomenon known as the Förster (Fluorescence) Resonance Energy Transfer (FRET), or by the more general phenomena of energy migration, or excitation percolation, followed by energy trapping, analogous to the energy transport and funneling process in photosynthetic antenna. On the basis of imaging results summarized in FIG. 20, the nanoconstruct 7 provided the greatest contrast between the tumor and non-tumor tissues.

Figure 19:
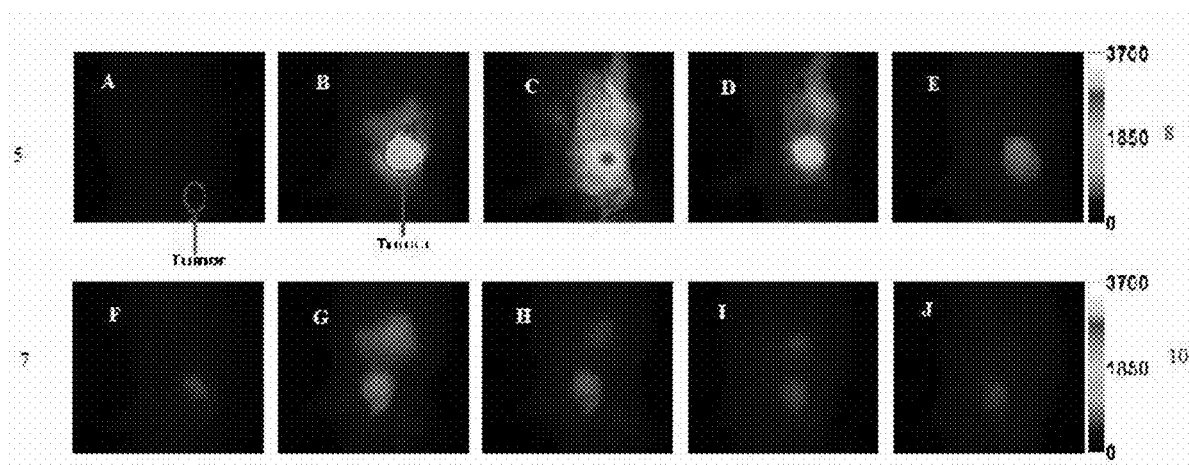
FIG. 19 shows whole body fluorescence images of a control mouse (A), nanoconstructs/formulation 5 (B), 7 (C & D), 8 (E & F), 9 (G & H) and 10 (I & J) in BALB/c mice bearing Colon-26 tumors. For A-J the excitation wavelength was 782 nm. Images A, B, C, E, G, & I and D, F, H, & J were taken 24 and 48 hours post i.v. injection, respectively.
Figure 20:
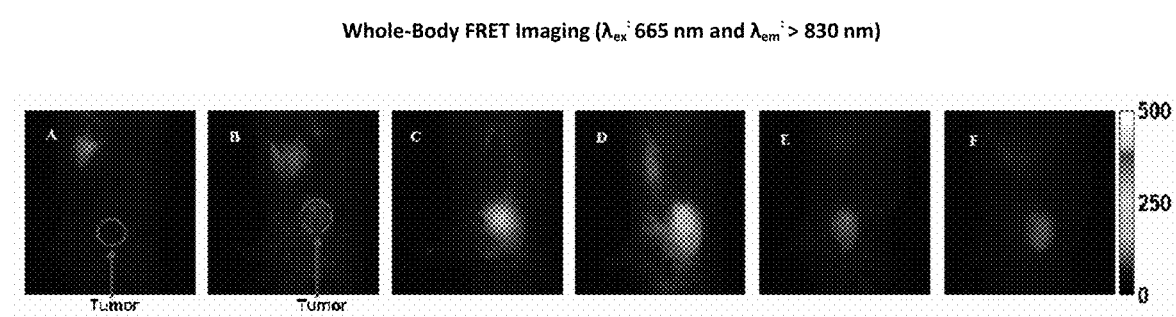
FIG. 20 shows whole body FRET images of a control mouse (A), nanoconstructs/formulation 5 (B), 7 (C), 8 (D), 9 (E) and 10 (F) in BALB/c mice bearing Colon-26 tumors. For A-F the excitation wavelength was 665 nm. Images A-F were taken 24 hours post i.v. injection.

Specifically, FIG. 19 shows whole body fluorescence images of a control mouse (A), nanoconstructs/formulation 5 (B), 7 (C & D), 8 (E & F), 9 (G & H) and 10 (I & J) in BALB/c mice bearing Colon-26 tumors. For A-J the excitation wavelength was 782 nm. Images A, B, C, E, G, & I and D, F, H, & J were taken 24 and 48 hours post i.v. injection, respectively and FIG. 20 shows whole body FRET images of a control mouse (A), nanoconstructs/formulation 5 (B), 7 (C), 8 (D), 9 (E) and 10 (F) in BALB/c mice bearing Colon-26 tumors. For A-F the excitation wavelength was 665 nm. Images A-F were taken 24 hours post i.v. injection.

Figure 21A:
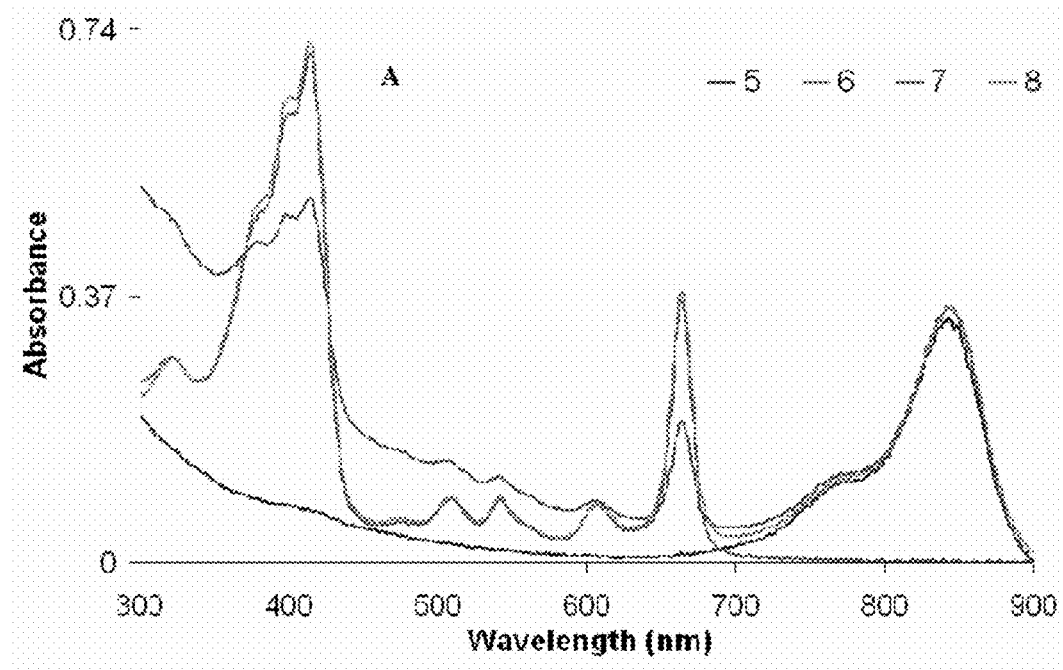
FIG. 21A shows an absorbance curve for constructs 5, 6, 7, and 8 at various wave lengths.
Figure 21B:
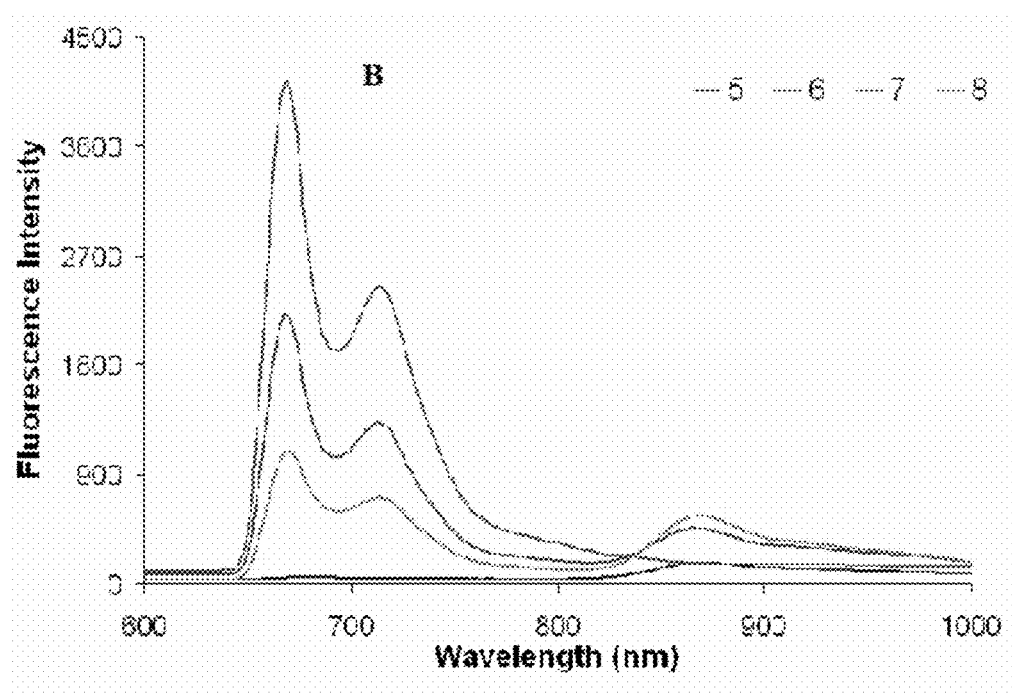
FIG. 21B shows fluorescent intensity for constructs 5, 6, 7, and 8 at 532 nm excitation.
Figure 21C:
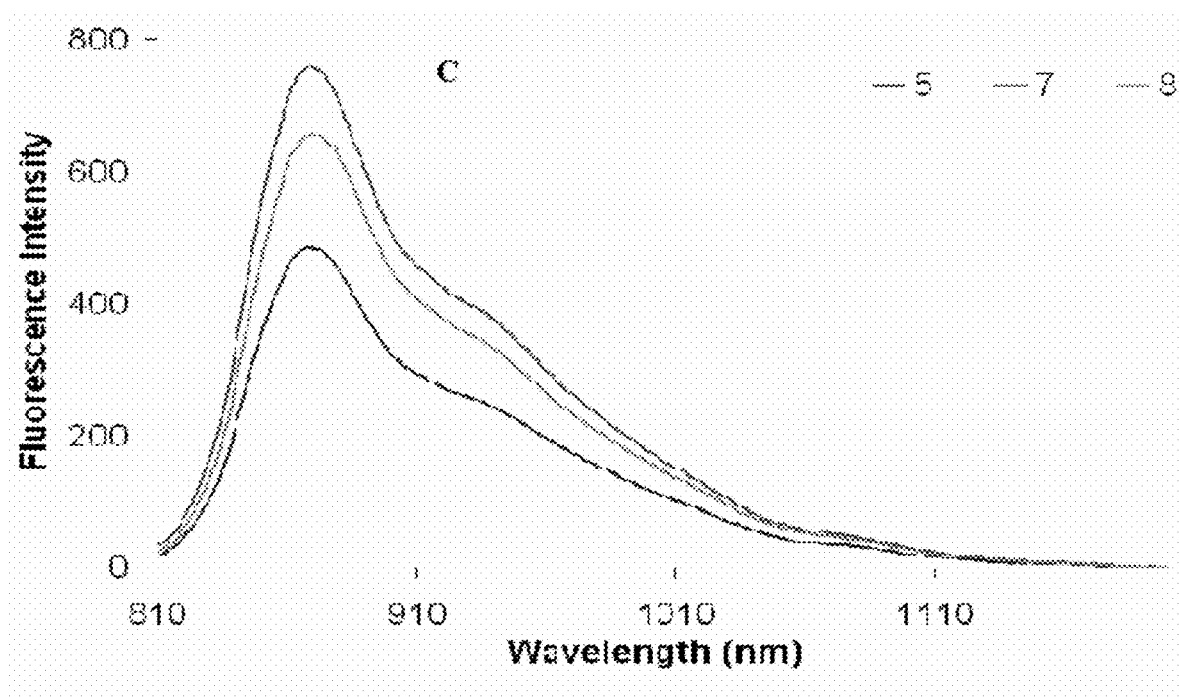
FIG. 21C shows fluorescent intensity for nanoconstructs 5, 7, and 8. Fluorescence was more intense for nanoconstructs 7 and 8 than for pure CD nanoconstruct 5, even if difference in absorption at 785 nm was minimal.

It is known that when a PS is in close proximity to a longer wavelength-absorbing fluorophore, with a spectral overlap between the fluorescence of the PS and the absorbance of the fluorophore, then upon exciting the PS, the PS fluorescence decreases due to the energy transfer to the fluorophore and the singlet oxygen yield also diminishes. This phenomenon was evident for the nanoconstructs containing both the PS and the cyanine dye. To determine the degree of energy transfer between PS and fluorophore, the fluorescence of nanoconstructs 7 and 8 were compared with 5 and 6. The concentration for the cyanine dye was kept constant in all nanoconstructs and the concentration of 1 for nanoconstruct 6 and 8 was kept the same and was two times higher than for nanoconstruct 7. The fluorescence spectrum in FIG. 21B shows the difference in fluorescence intensity for 6, 7, and 8, which resulted from the different efficiency of the PS→CD energy transfer in these nanoconstructs. This energy transfer caused a decrease in intensity of the PS fluorescence along with an increase in CD fluorescence intensity. The energy transfer was strongest for nanoconstruct 8 since the fluorescence spectrum displayed the least intense fluorescence band from PS moiety ($\lambda_{max} \approx 670$ nm) and the most intense fluorescence band from the CD moiety ($\lambda_{max} \approx 870$ nm) upon excitation at 532 nm (FIG. 21A). Also, on excitation of 3 at 785 nm, CD fluorescence was more intense for nanoconstructs 7 and 8 than for pure CD nanoconstruct 5, even if difference in absorption at 785 nm was minimal (FIG. 21C). This was an effect of the post-loaded PS molecules; their presence in the post-loaded PAA nanoparticles could result in a more dense environment for the CD molecules, which, in turn, enhanced the radiative rate for the CD fluorophore. Overall, combination of the facts that the PS fluorescence under 532 nm excitation for 7 and 8 was less intense than for 6 and, at the same time, CD fluorescence under 532 nm excitation was more intense for 7 and 8 than for 5 unambiguously demonstrates that energy transfer PS→CD occurs in nanoconstructs and its efficiency for 8 was higher than that for 7. This higher ET efficiency can be explained by the higher concentration of PS post-loaded to nanoparticles resulting in less average distance between PS chromophores, allowing electronic excitation to migrate from one PS molecule to others, before being trapped by the CD chromophore. Lovell et al[30] had reported a similar observation in a series of pyropheophorbide-a conjugated with quenchers. An increase in concentration of the photosensitizer possibly results in a higher probability of electronic excitation energy percolation causing the trapping of the electronic excitations by lower concentration of the quenchers (cyanine dyes).

Figure 21D:
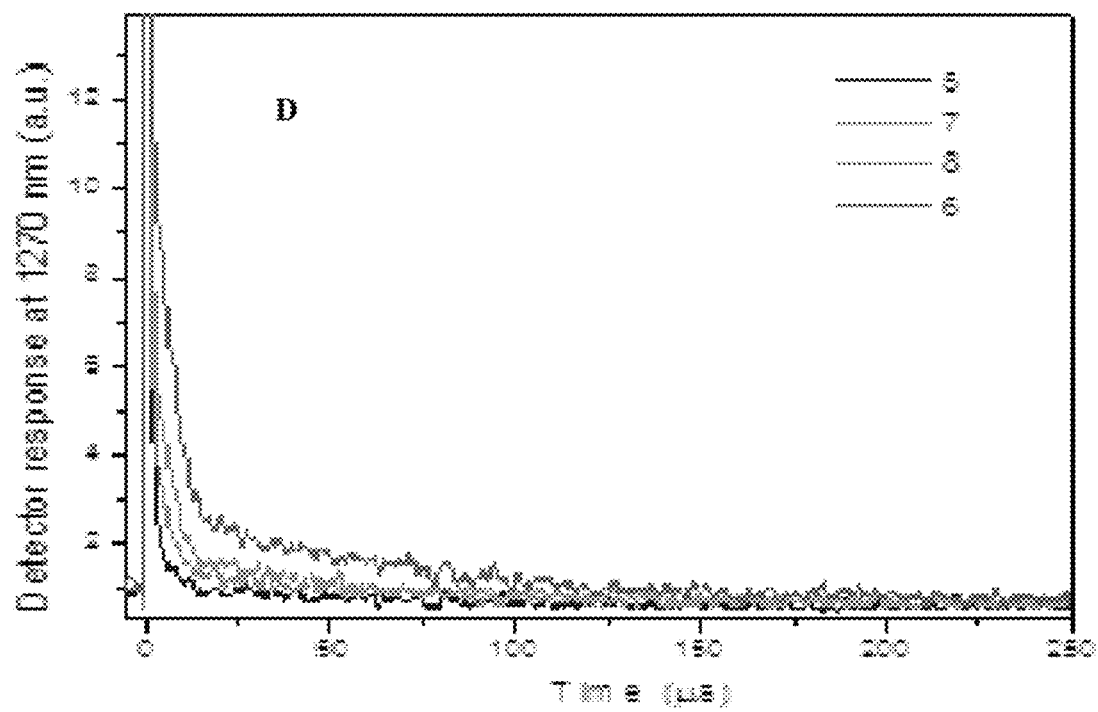
FIG. 21D shows detector response for constructs 5, 6, 7, and 8 illustrating singlet oxygen decay rates.

To confirm that the more efficient PS→CD energy transfer in the nanoconstructs correlates with a less efficient production of singlet oxygen, we compared the singlet oxygen generation yield of the nanoconstructs using the singlet oxygen phosphorescence spectroscopy. Phosphorescence decays are shown in FIG. 21D and demonstrate two clearly distinguishable decay rates for the singlet oxygen. One is shorter with a lifetime of ~4 μs (which is close to the lifetime of singlet oxygen in water[31]) suggesting that it is derived from the excited oxygen molecules decaying in aqueous environment. The second decay rate is much longer with a lifetime of ~100 μs, which is apparently associated with singlet oxygen decaying within the PAA matrix. The production of singlet oxygen was highest for the PS only formulation (nanoconstruct 6) and decreases for three others in the order of 8>7>5. We assume that the production of singlet oxygen by 5 was negligible since it dose not contain PS; thus the decay curve for 5 practically depicts the Instrument Response Function of the setup. These results were understandable since there was twice the amount of PS in nanoconstruct 8 which should produce more singlet oxygen, even if energy transfer from PS is more efficient in 8 than in 7. Overall, it is important to stress that both 8 and 7 nanoconstructs showed singlet oxygen production comparable with that from the PS nanoparticle formulation, nanoconstruct 6. These and our current results demonstrate that in a two-chromophore system, an increase in FRET and/or energy percolation increases the fluorescence intensity of the acceptor or longer wavelength (lower energy) chromophore, which decreases singlet oxygen production.[18,19]

Comparative in vivo PDT efficacy of PAA NPs containing HPPH and CD in variable ratios (Nanoconstructs 6-10 vs. PS 1)

Specifically, FIGS. 21A to 21D show: 21A) Electronic absorption spectra of nanoconstructs 5, 6, 7, and 8 in water. 21B) Fluorescence emission of nanoconstructs 5, 6, 7, and 8 excited at 532 nm in water. 21C) Fluorescence emission of nanoconstructs 5, 7, and 8 excited at 785 nm. 21D) The singlet oxygen production of nanoconstructs 5, 6, 7, and 8 in water was detected by measuring the phosphorescence of singlet oxygen, $^1O_2$, at 1270 nm upon excitation by a 532 nm laser. Nanoconstruct 5 was used as the instrument response function (IRF) as it does not produce $^1O_2$.

HPPH, derived from chlorophyll-a, is an effective PDT agent with low skin phototoxicity and, in BALB/c mice bearing Colon 26 tumors, a complete PDT response of 40% was observed at a dose of 0.47 moles/kg on exposing the tumors with light at 665 nm, delivered at a fluence and fluence-rate of 135 J/cm$^2$ and 75 mW/cm$^2$ 24 hours post-injection. To compare the newly developed nanoconstructs with free HPPH, we used similar treatment parameters as described above. In preliminary screening, the PDT response (no tumor regrowth) for HPPH 1, nana-constructs 6, 7, 8, 9 and 10 was 40%, 40%, 60%, 30%, 40%, and 30%, respectively. The nanoconstruct 7 containing HPPH and cyanine dye 3 in a ratio of 2-1 was more effective than PS 1 alone in 1% Tween 80 formulation and nanoformulations 9 and 10, and also provided (i) the ability to both image and treat the tumors, which could be extremely useful for a "See and Treat" approach and (ii) compared to the synthetic HPPH-cyanine dye conjugate in which the imaging dose was 8- to 10-fold lower than the therapeutic dose, a single dose (0.47 moles/kg) of nanoconstruct 7 can be used for both tumor imaging and PDT.

Figure 22A:
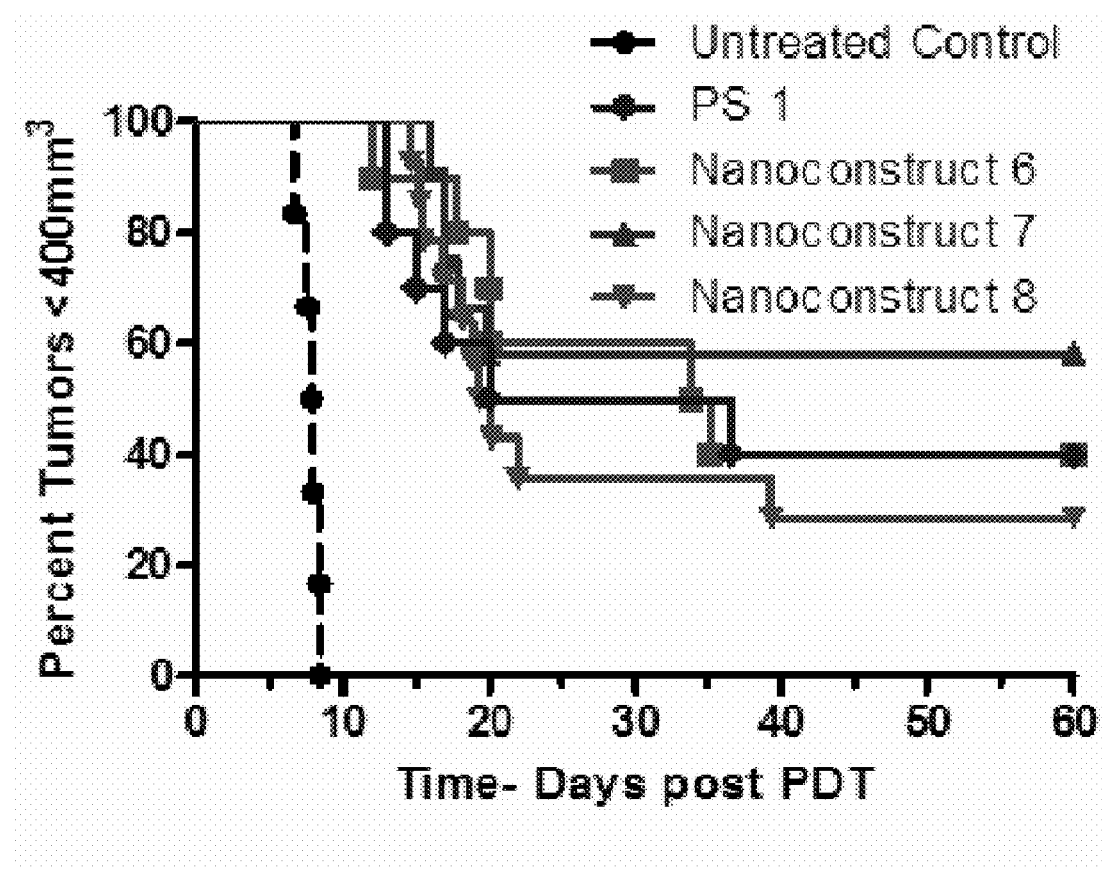
FIG. 22A shows tumor response versus time for untreated control, PS1 (HPPH), and nanoconstructs 6, 7, and 8.
Figure 22B:
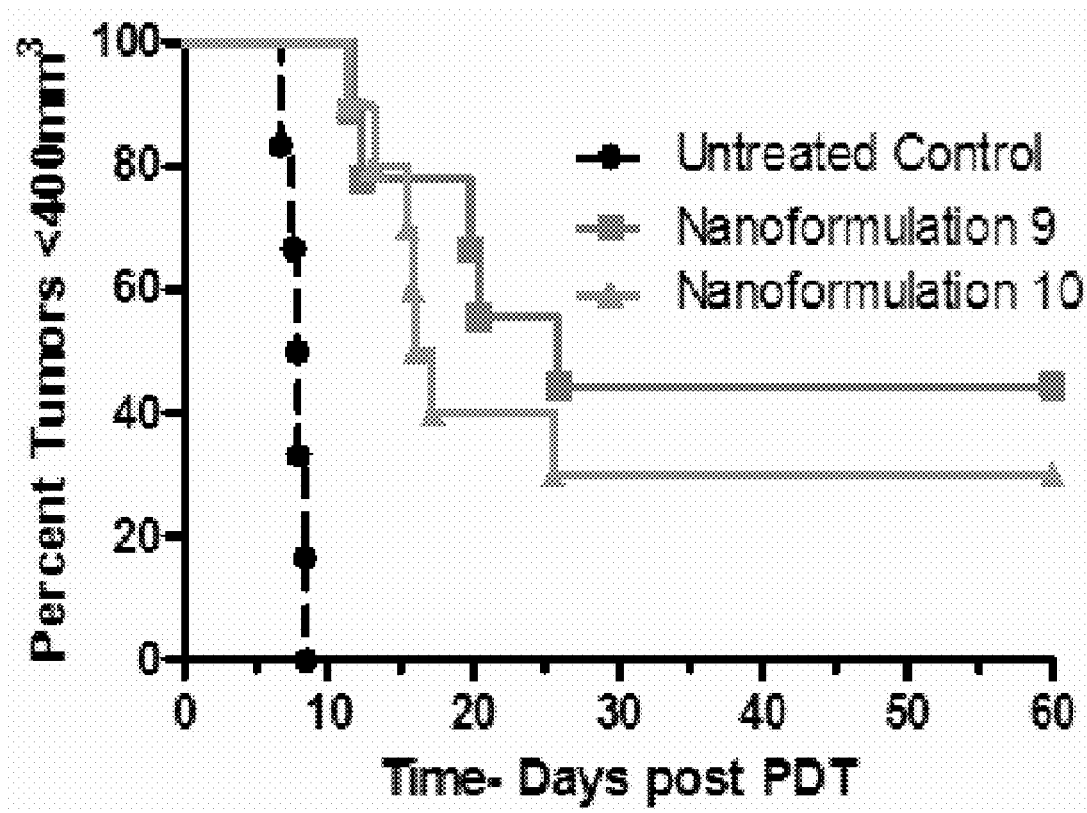
FIG. 22B shows tumor response versus time for untreated control, nanoformulation 9 and nanoformulation 10.

To demonstrate both tumor imaging and PDT using the same compositions, BALB/c mice bearing subcutanaceous Colon-6 tumors were treated as shown in FIGS. 22A and 22B. FIGS. 22A and 22B show Kaplan-Meier plots for BALB/c mice bearing subcutaneous Colon-26 tumors treated with PS 1 and various nanoconstructs at the PS dose of 0.47 mol/kg. The tumors were exposed to light at the light fluence and fluence rate of 135 J/cm$^2$ @ 75 mW/cm$^2$. Under same treatment parameters nanoconstruct 7 (containing HPPH and CD in a ratio of 2:1) showed the best long term PDT efficacy (6/10 mice were tumor-free on day 60).

Compared to encapsulation, the post-loading approach was more effective when hydrophobic compounds were used in conjunction with PAA nanoparticles. PAA NPs provide a great platform for post-loading because of the porous nature of the polyacrylamide-based hydrogels, wherein the hydrophobic part of the molecule may interact preferentially. We have found that the surfactant Tween-80 plays an important role in efficient retention of the compounds within the NPs. Its presence in an aqueous solution apparently causes formation of a micellar layer on the nanoconstruct surface whereby the polyethers form the outer hydrophobic layer and the oleic acid forms the inner, more hydrophobic layer of the construct.

Among all organic NIR fluorophores, cyanine dyes in general have shown great potential for fluorescence imaging. In this series of compounds, IR-820, a near-infrared (NIR) cyanine dye, is of particular interest due to its inherent desirable photophysical characteristics, namely excitation and emission in the NIR range beyond 750 nm, which allows for deeper tissue penetration of activating light; however, its tumor uptake is known to be low.

It has been shown that when Cy5 was encapsulated within PEG-coated silica nanoparticles (3.3 and 6.0 nm diameter, respectively), the fluorescence intensity of the dye increased by 2.0-2.5 times, compared to that of the free dye. This prompted us to investigate the utility of PAA nanoconstructs for the delivery of both imaging and therapeutic agents. We found that the newly constructed nanoparticles were capable of delivering a high payload of both the PS and the CD molecules to the tumor. This is likely due to the "Enhanced Permeability and Retention" (EPR) effect.

The UV-Visible and fluorescence spectrometry studies confirmed that both hydrophobic PS and hydrophilic fluorophores related to cyanine dyes can be co-loaded into amine functionalized PAA nanoconstructs and maintain their photophysical characteristics. The DLS and SEM images show that upon co-post-loading, the diameter and spherical shape of the NPs remain intact. The in vitro spectroscopic measurements show that excitation of nanoconstruct 8 channels more energy transport/FRET from HPPH to cyanine dye 7, resulting in reduced efficiency of 1 for PDT efficacy. In contrast to synthetic HPPH-cyanine dye conjugates, a single dose of the PAA nanoconstruct can be used simultaneously for tumor imaging and for efficient long-term tumor cure by PDT. Additionally, nanoconstructs 9 and 10 produced lower in vivo FRET signal as compared to nanoconstructs 7 and 8, however the nanoconstruct 7 still provided the best PDT outcome (60% for PS 1 vs. 40% for nanoconstruct 6). Further studies to improve the target-specificity of the nanoconstructs by introducing certain target-specific agents at the periphery of the PAA NPs are in progress.

Details For Preparation of Compounds and Constructs are as Follows:

Materials:

Acrylamide, N,N,N',N'-tetraethylmethylenediamine (TEMED), ammonium persulfate (APS), polyethylene glycol dodecyl ether (Brij 30), 3-(acryloyloxy)-2-hydroxypropyl methacrylate (AHM), hexane, and dioctyl sulfosuccinate (AOT) were purchased from Sigma-Aldrich (USA). 3-(aminopropyl)methacrylamide (APMA) was obtained from Polysciences Inc., USA, and ethanol (190 proof) was obtained from Fisher Scientific, USA. Nanosep 100K Omega filters were purchased from Pall USA. Amicon ultra-filtration cell equipped with a Biomax 500 kDa cutoff membrane was purchased from Millipore, USA Synthesis of Blank Amine Functionalized Polyacrylamide Nanoparticles (AFPAA):

The synthesis was similar to the previously reported method by Wisner et al.[26] In brief, hexane (45 ml, VWR, USA) was added into a dried 100 ml round bottom flask and stirred under a constant purge of argon. Suitable amounts of AOT (1.6 g, Sigma-Aldrich, USA) and Brij 30 (3.1 g, Sigma-Aldrich, USA) were added to the reaction flask and stirring was continued under argon protection for 20 min. Acrylamide (711 mg), 3-(aminopropyl)methacrylamide (89 mg) and biodegradable 3-(acryloyloxy)-2-hydroxypropyl methacrylate (428 mg) were dissolved in phosphate buffered saline (2 ml) (PBS, pH=7.4) in a glass vial by sonication to obtain a uniform solution. The solution was then added to the hexane reaction mixture and vigorously stirred for another 20 min at room temperature. Polymerization was initiated by adding freshly prepared ammonium persulfate aqueous solution (10% w/v aqueous solution, 40 l) and TEMED (40 l). The resulting solution was stirred vigorously overnight. At the completion of polymerization, hexane was removed by rotary evaporation and the particles were precipitated by addition of ethanol (50 ml). The surfactant and residual monomers were washed away from the particles with ethanol (150 ml) followed by washing with water (100 ml) 5 times each in an Amicon ultra-filtration cell equipped with a Biomax 500 kDa cutoff membrane. The concentrated nanoparticles were lyophilized for two days for storage, and reconstituted by suspending in water before use.

Characterization of Size and Dispersion of AFPAA:

The dynamic light scattering measurements were performed on a Nicomp 370 Submicron Particle Sizer (Nicomp, Santa Barbara, Calif.). The NP solution was placed in a borosilicate glass capillary tube, and diluted with water to an intensity reading of 300 kHz. The readings were performed in triplicate with each run set for 5 minutes. The volume weighted Gaussian or Nicomp's proprietary analysis mode was utilized to determine the mean hydrodynamic diameter. The morphology and size of the dried NP were characterized by scanning electron microscope (SEM). The NP solution of 0.2 mg/ml was prepared in water and a drop of the NP solution was placed on the SEM aluminium specimen mount (aluminum) and dried gradually at room temperature. The sample was then sputter coated with gold and the SEM images were taken on the Philips ESEM XL30.

Post-Loading of the photosensitizer 1, and the cyanine dyes 2, and 3 to blank AFPAA to create nanoconstructs 4, 5, 6, 9, and 10: 10 mg of lyophilized PAA NPs were dissolved in 1 ml of 1% Tween-80/18 MΩ water solution. Prior to post-loading with the NPs, the hydrodynamic diameter was measured to ensure that the NPs are of the appropriate diameter and that the NPs are not aggregated. When they are aggregated, the hydrodynamic diameter increases. The NPs can be sonicated in a water bath sonicator for several minutes to disperse the aggregates. To post-load, 10 μl of 1, 2, or 3 was added to the NP solution and magnetically stirred at a constant rpm for at least 2 hours. Excess DMSO, Tween-80, and 1, 2, or 3 that did not post-load was removed via centrifuge filtration (Amicon Ultra-15 30 kDa centrifuge filter), for 30 minutes at 5,000 rpm. The filtrate was measured spectrophotometically and if 1, 2, or 3 was detected; the retentate was reconstituted to the original volume with water and recentrifuged. This step was repeated until no absorbance for 1, 2, or 3 was detected in the filtrate. The concentration of 1, 2, and 3 was measured spectrophotometrically in ethyl alcohol according to the Beer's-Lambert law using 47,500, 200,000, and 207,455 (L mol$^{-1}$ cm$^{-1}$) as the molar extinction coefficient for 1, 2, and 3, respectively, after they were syringe filtered with a 0.2 μm regenerated cellulose syringe filter. If scattering was present in the absorbance spectra, the NPs were centrifuged in a microfuge membrane-filter (Nanosep 100K Omega) at 14,000 RPM for 10 minutes. The filtrate was used to calculate the concentration of 1, 2, or 3. To create nanoconstrust 9 and 10, nanoconstruct 6 and nanoconstrust 3 are mixed together such that the molar ratio of PS 1 and cyanine dye 3 is 2-1 and 4-1, respectively. The NPs are stored at 4° C. until further use.

Post-Loading of the Photosensitizer 1 and the Cyanine Dye 3 to Blank AFPAA to Create Nanoconstructs 7 and 8:

The lyophilized AFPAA NPs were dissolved in 1% Tween-80 to a final concentration of 10 mg of NPs/1 ml of 1% Tween-80. The hydrodynamic diameter of the blank PAA NPs were measured by DLS prior to use to ensure the NPs are of appropriate size. If aggregation is present, the hydrodynamic diameter may increase; therefore the NPs were sonicated in a water bath sonicator for several minutes to disperse the aggregation. Prior to post-loading, 1 and 3 were dissolved in DMSO to prepare 20 mM solutions. For 2 ml of NP solution, 20 or 40 μl of 1 was post-loaded as the first step of making nanoconstructs 7 and 8, respectively, and excess reagents were removed by centrifuge filtration as before until no PS 1 is detected in the filtrate. The concentration of PS 1 was measured spectrophotometrically. If scattering is observed (determined spectrophotometrically), the NPs in ethanol were centrifuged in a microfuge membrane-filter at 14,000 RPM for 10 minutes to remove PS 1 from the NPs. The filtrate was used for calculating the concentration of the PS. The concentration of the PS 1 and 3 in nanoconstructs 7 and 8 was 200 and 400 μM respectively. To 7 and 8, 20 μA of 3 in 20 mM DMSO was added and magnetically stirred for 2 hours. The same centrifuge filtration steps used for 1 were employed for 3. The concentration of 1 and 3 was measured spectrophotometrically (as described above), after they were syringe filtered with a 0.2 μm regenerated cellulose syringe filter. The ratio of 1 to 3 in nanoconstructs 7 and 8 was 2-1 and 4-1, respectively. The NPs are stored at 4° C. until further use.

Whole-Body Fluorescence Imaging:

The first group of BALB/c mice were imaged with cyanine dye 2 and the nanoconstruct 4 post loaded with cyanine dye 2 (dose: 0.3 μmoles/kg). The second group of mice was imaged with cyanine dye 3 and nanoconstruct 5 (dose: 0.3 μmoles/kg). The third and fourth groups of mice were imaged with nanoconstruct 7 containing the cyanine dye 3 post-loaded (dose: 0.216 moles/kg) and the PS 1 post-loaded (dose: 0.47 μmoles/kg) and the nanoconstruct 8 containing the cyanine dye 3 post-loaded (dose: 0.108 μmoles/kg) and PS 1 post-loaded (dose: 0.47 μmoles/kg). The fifth and sixth groups of mice were imaged post with nanoconstruct 9 containing the cyanine dye 3 post-loaded (dose: 0.236 μmoles/kg) and the PS 1 postloaded (dose: 0.47 μmoles/kg), and the nanoconstruct 10 contained 3 post-loaded (dose: 0.127 μmoles/kg) and the PS 1 post-loaded (dose: 0.47 μmoles/kg).

Optical Imaging Setup:

The fluorescence imaging was conducted in accordance with a protocol approved by the Institutional Animal Care and Use Committee IACUC at Roswell Park Cancer Institute and the Guide for the Use of Laboratory Animals. BALB/c mice (3 mice/group) bearing subcutaneous Colon 26 tumors on the right shoulder were injected i. v. (tail-vein) with either cyanine dyes or nanoconstructs/formulations. At 24, 48 and 72 h post-injection, mice were anesthetized with ketamine/xylazine by intraperitonial injection and imaged with a monochrome scientific grade CCD camera CRI (Nuance, Woburn, Mass.). For tumor imaging with cyanine dyes 2 and 3, the CCD camera was employed in the mono mode and a 782 nm BWF light source (B&W-Tek, Newark, Del.) continuous wave laser was used for excitation. The fluorescence emission was collected with an 800 and 830 nm long pass filters in series. To image the in vivo fluorescence resonance energy transfer (FRET) or energy transfer (ET) from the PS 1 to cyanine dye 3, 1 was excited at 665 nm from a pumped argon-dye laser, and the fluorescence emission of 3 was collected with an 800 and 830 nm long pass filters in series. Fluorescent images for each group were set to the same lookup table (LUT, royal) and signal intensity in ImageJ (NIH, USA).

Figure 23A:
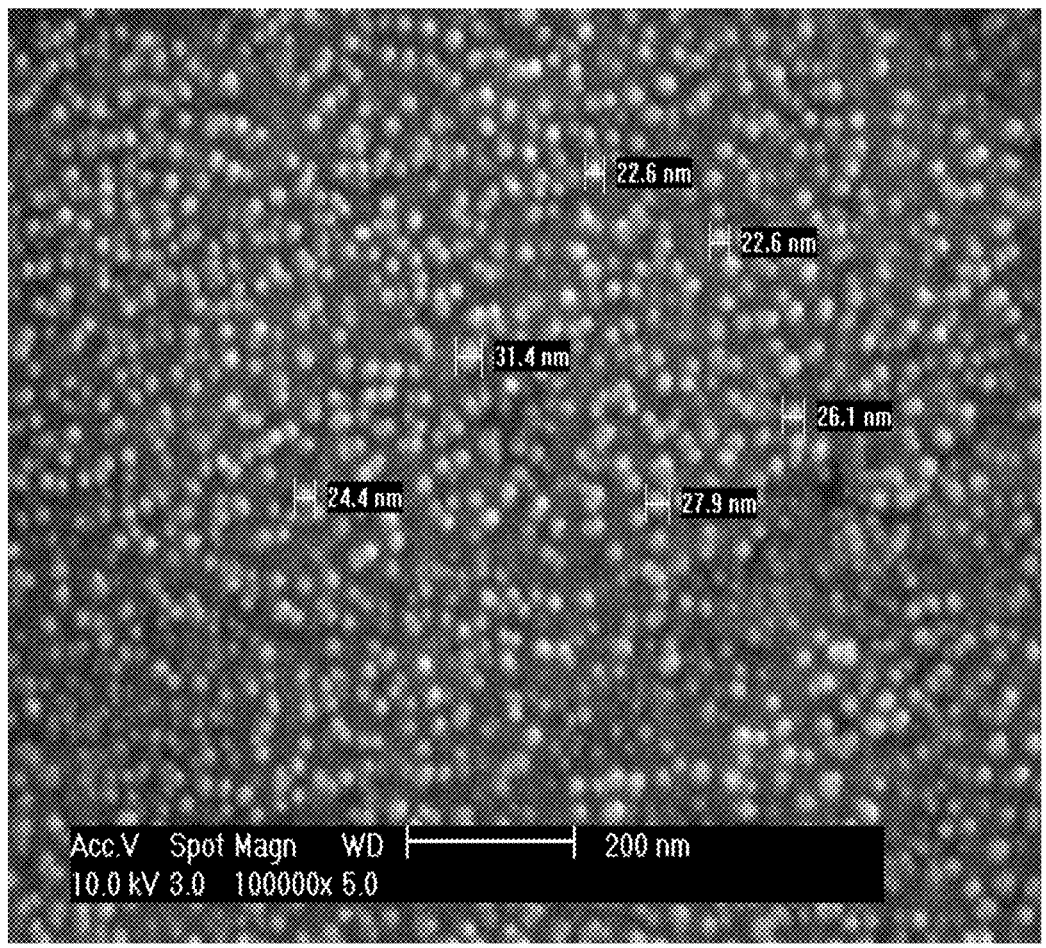
FIG. 23A shows an SEM for nanoconstruct 7 (representative of all groups).
Figure 23B:
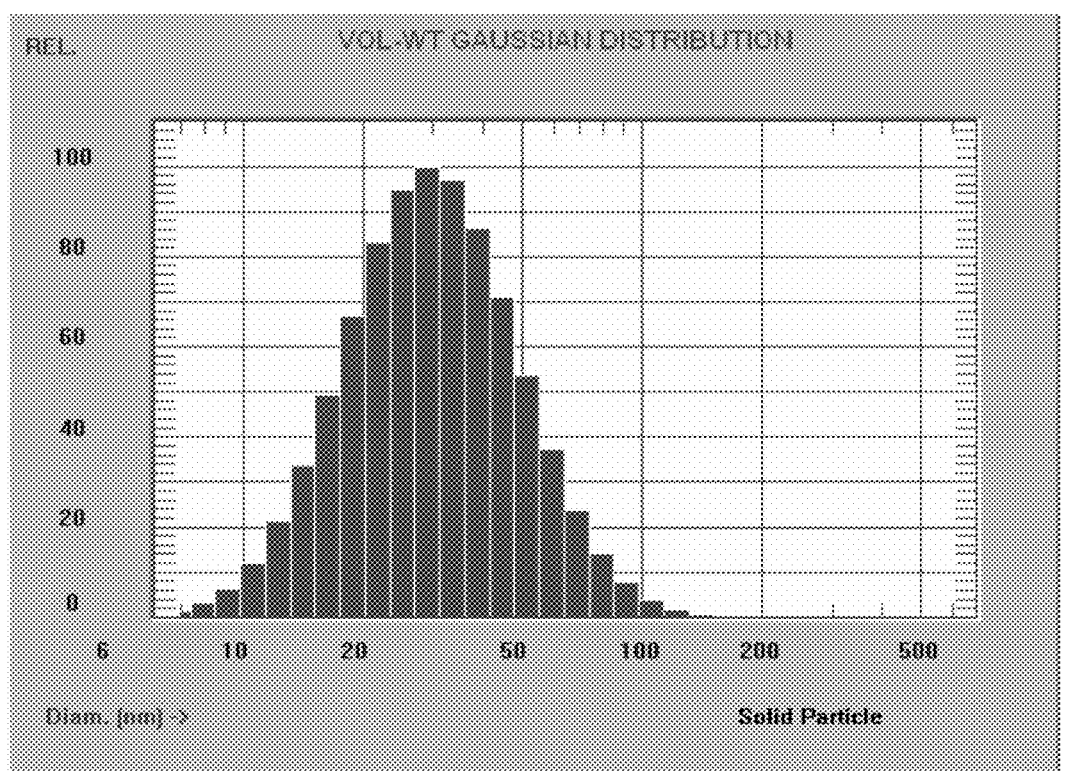
FIG. 23B shows a DLS particle size distribution for Blank PAA NPs. The mean diameter is 33.5 nm.
Figure 23C:
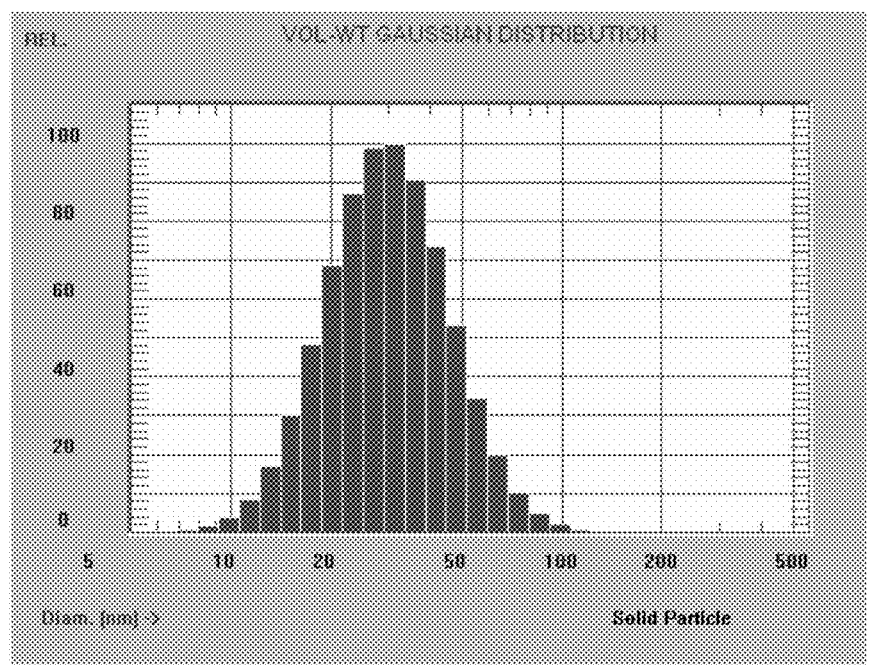
FIG. 23C shows a particle size distribution for nanoconstruct 6. The mean diameter is 32.5 nm.
Figure 23D:
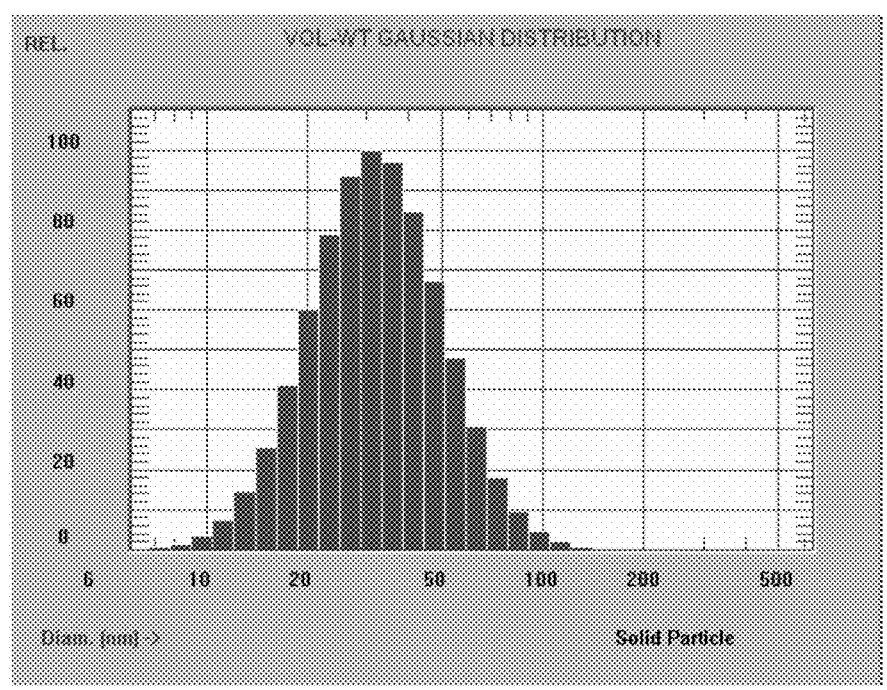
FIG. 23D shows a particle size distribution for nanoconstruct 5. The mean diameter is 35.2 nm.

FIGS. 23A-23D: FIG. 23A shows an SEM for nanoconstruct 7 (representative of all groups) and FIG. 23 B shows a DLS particle size distribution for Blank PAA NPs, FIG. 23C shows a particle size distribution for nanoconstruct 6, and FIG. 23D shows a particle size distribution for nanoconstruct 5 in Tween-80/water (concentration of Tween-80 is <1%). The mean diameter is 33.5 nm, 32.5 nm, and 35.2 nm for FIG. 23B, FIG. 23C, and FIG. 23D, respectively. The mean hydrodynamic diameter as determined by DLS is similar for all nanoconstruct/formulations.

Figure 24A:
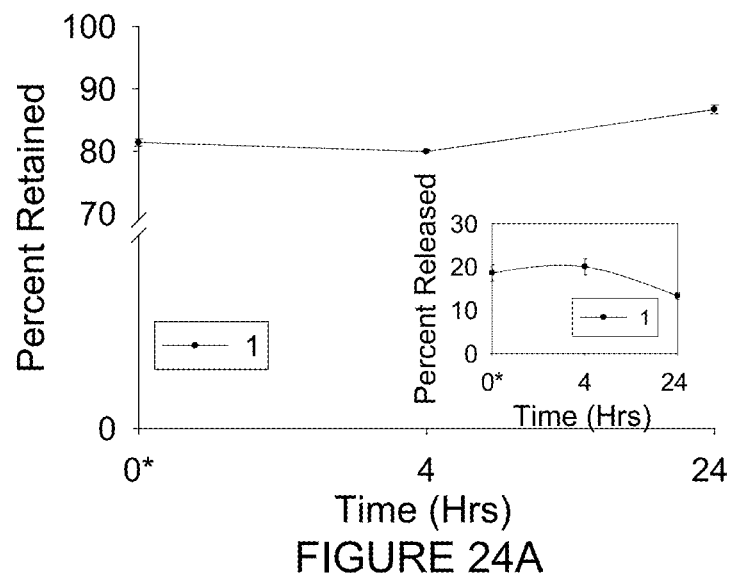
FIGS. 24A-24L show Release/Retention Profiles of PS 1 (24A, 24C, 24E, 24G, & 24I) and/or cyanine dye 3 (24B, 24D, 24F, 24H, & 24J) from nanoconstructs 5, 6, 7, 8, 9, and 10 in a 1% Human Serum Albumin (HSA) solution.
Figure 24B:
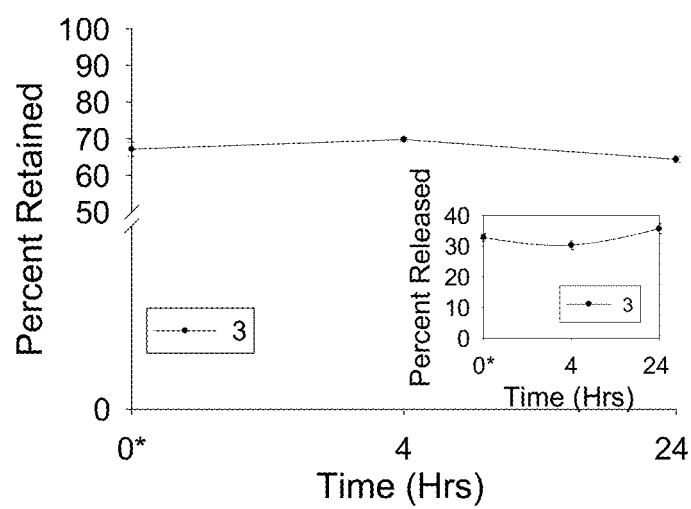
Figure 24C:
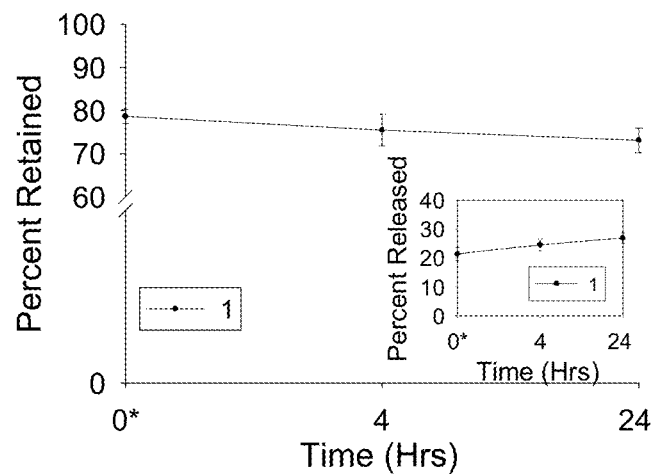
Figure 24D:
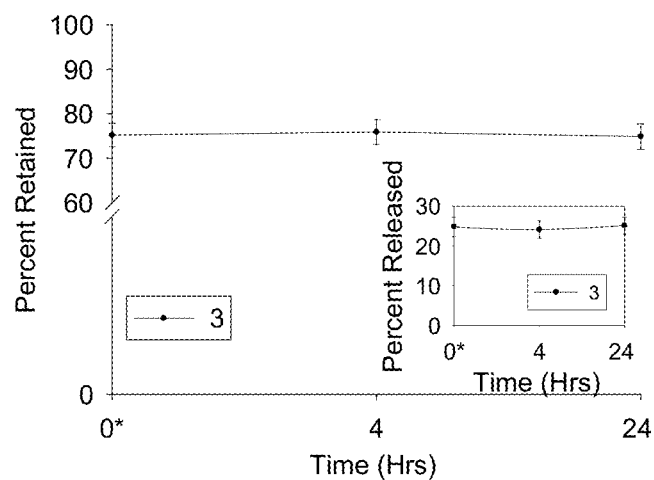
Figure 24:
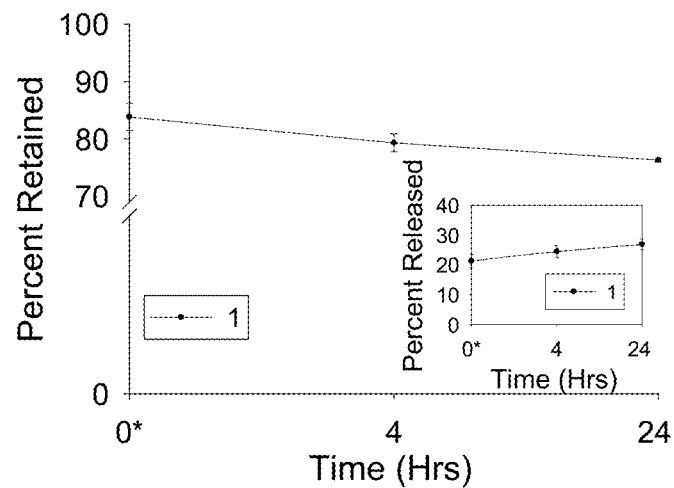
Figure 24F:
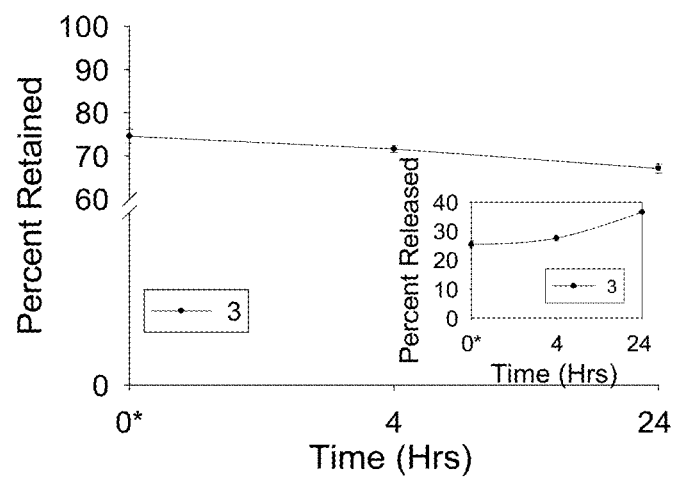
Figure 24G:
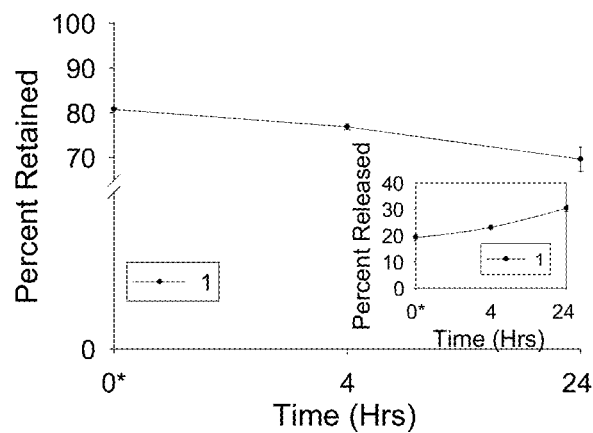
Figure 24H:
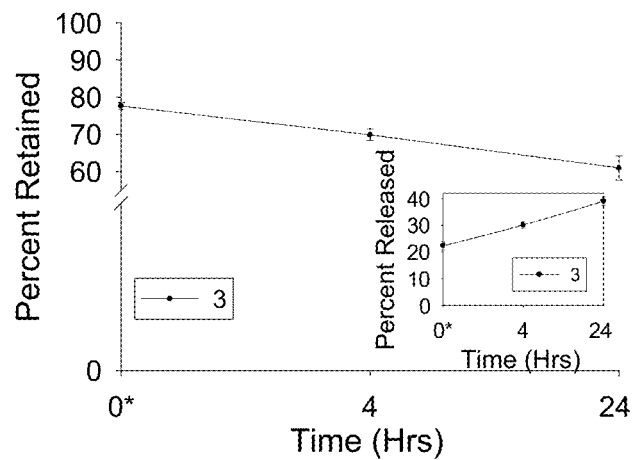
Figure 24I:
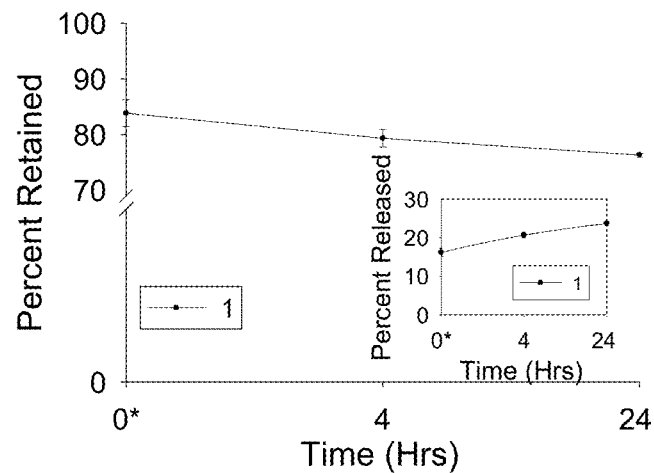
Figure 24J:
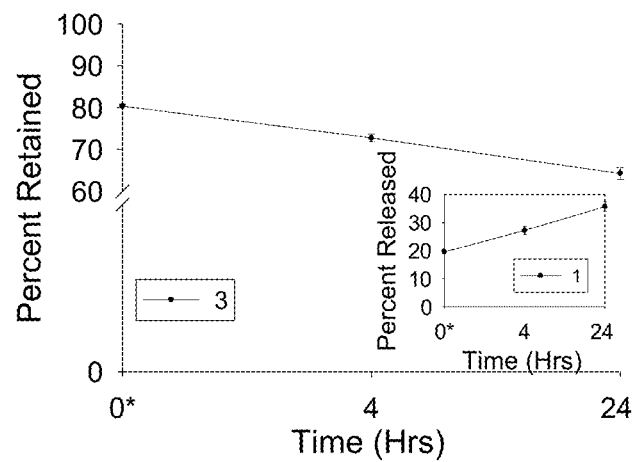
Figure 24K:
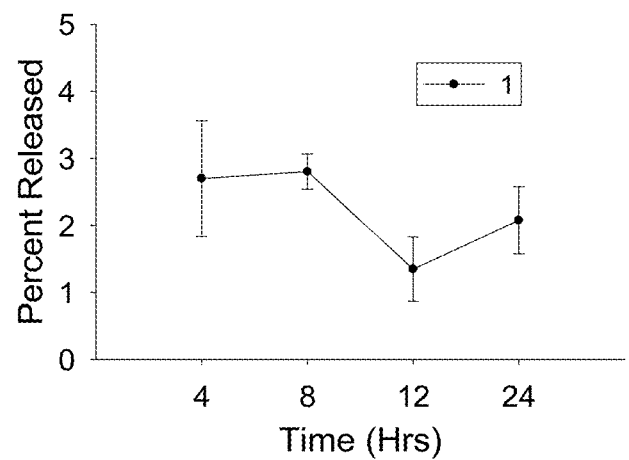
Figure 24L:
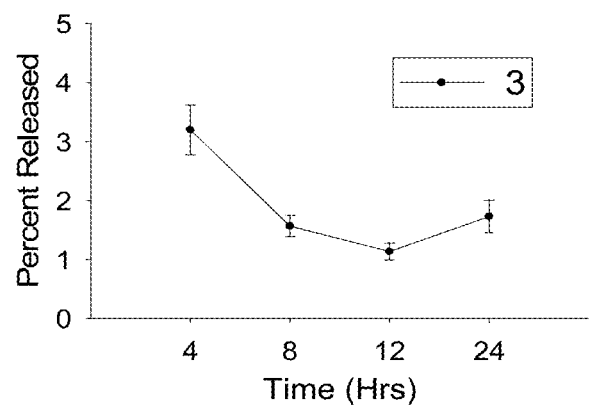

FIGS. 24A-24L show Release/Retention Profiles of PS 1 (24A, 24C, 24E, 24G, & 24I) and/or cyanine dye 3 (24B, 24D, 24F, 24H, & 24J) from nanoconstructs 5, 6, 7, 8, 9, and 10 in a 1% Human Serum Albumin (HSA) solution. The release/retention was measured immediately upon addition of the various nanoconstucts in 1% HSA (*), 4, and 24 hours post-addition of the nanoconstructs in a 1% HSA solution. Each experiment was done in triplicate with the symbols representing the mean. The error bars are standard error of the mean. FIGS. 24K and 24L show Release Profiles of PS 1 and cyanine dye 3 from nanoconstruct 7 in a 25% Bovine Calf Serum (BCS) solution at 37° C. The release was measured 4, 8, 12, and 24 hours post-addition of nanoconstruct 7 in 25% BCS. Each experiment was done in triplicate with the symbols representing the mean. The error bars are standard error of the mean.

What is claimed is:

1. A composition comprising a plurality of polyacrylamide nanoparticles, at least some of said nanoparticles having a tetrapyrollic photosensitizer for photodynamic therapy postloaded onto the nanoparticle after nanoparticle formation, and at least some of said nanoparticles containing an imaging agent, said tetrapyrollic photosensitizer having the structural formula:

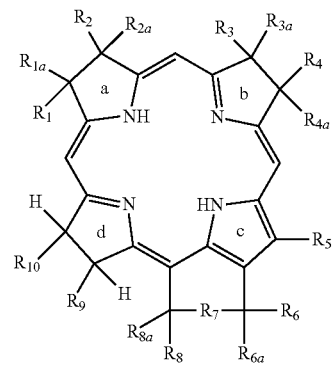

$R_1$ and $R_2$ are each independently substituted or unsubstituted alkyl, substituted or unsubstituted alkenyl, —C(O)$R_a$ or —COOR$_a$ or —CH(CH$_3$)(OR$_a$) or —CH(CH$_3$)(O(CH$_2$)$_n$XR$_a$) where $R_a$ is hydrogen, substituted or unsubstituted alkyl, substituted or unsubstituted alkenyl, substituted or unsubstituted alkynyl, or substituted or unsubstituted cycloalkyl; where $R_2$ may be —CH=CH$_2$, —CH(OR$_{20}$)CH$_3$, —C(O)Me, —C(NR$_{21}$)CH$_3$ or —CH(NHR$_{21}$)CH$_3$ where X is an aryl or heteroaryl group;

n is an integer of 0 to 6;

where $R_{20}$ is methyl, butyl, heptyl, docecyl or 3,5-bis(trifluoromethyl)-benzyl; and $R_{21}$ is 3,5,-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaralkyl or =NR$_{20}$ where $R_{20}$ in =NR$_{20}$ is 3,5-bis(tri-fluoromethyl)benzyl or —CH$_2$X—R$^1$ or —YR$^1$ where Y is an aryl or heteroaryl group;

$R_8$ and $R_{8a}$ are each independently hydrogen or substituted or unsubstituted alkyl or together form =O;

$R_9$ and $R_{10}$ are each independently hydrogen, or substituted or unsubstituted alkyl and $R_9$ may be —CH$_2$CH$_2$COOR$^2$ where $R^2$ is an alkyl group that may optionally substituted with one or more fluorine atoms;

each of $R_1$-$R_{10}$, when substituted, is substituted with one or more substituents each independently selected from Q, where Q is alkyl, haloalkyl, halo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, allkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue.

2. The composition of claim 1 wherein the imaging agent is a cyanine dye.

3. The composition of claim 2 wherein the cyanine dye is postloaded onto the nanoparticle after nanoparticle formation.

4. The composition of claim 1 wherein the imaging agent is a $^{124}$I labeled compound.

5. The composition of claim 1 wherein the imaging agent is a PET, fluorescence or MR imaging agent.

6. The composition of claim 1 wherein at least some of the nanoparticles contain a targeting moiety.

7. The composition of claim 6 wherein the targeting moiety is a peptide, folic acid or a carbohydrate.

8. The composition of claim 2 where the cyanine dye is conjugated with the nanoparticle.

9. The composition of claim 1 where the photosensitizer is

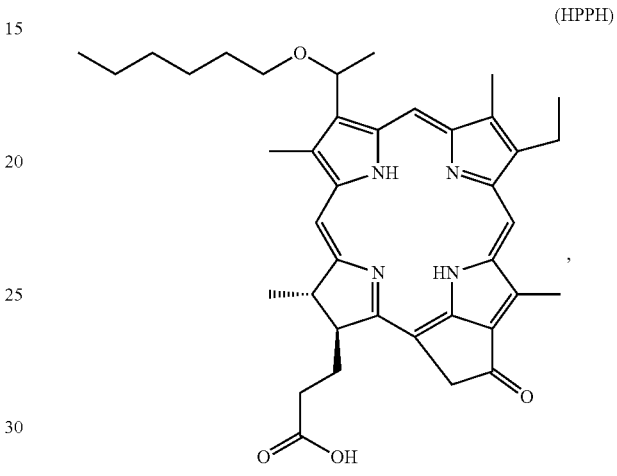

(HPPH)

purpurinimide having an absorbance between 680 and 720 nm, bacteriopurpurinimide having an absorbance between 780 and 800 nm or mixtures thereof.

10. The composition of claim 2 where the numerical ratio of postloaded photosensitizer moieties to cyanine dye moieties is from 1 to 1 to 10 to 1.

11. The composition of claim 10 where the numerical ratio of postloaded photosensitizer moieties to cyanine dye moieties is from 2 to 1 to 4 to 1.

12. The composition of claim 2 where the cyanine dye has the structural formula:

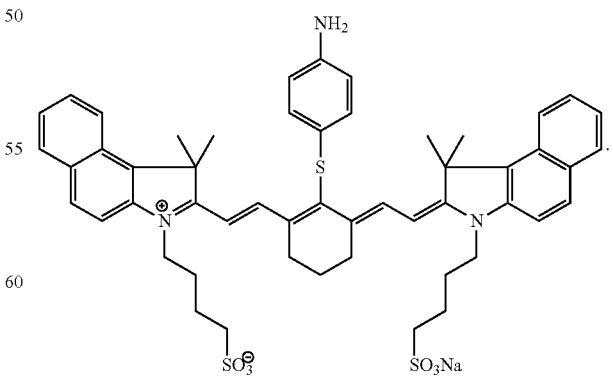

13. The composition of claim 1 where the photosensitizer is

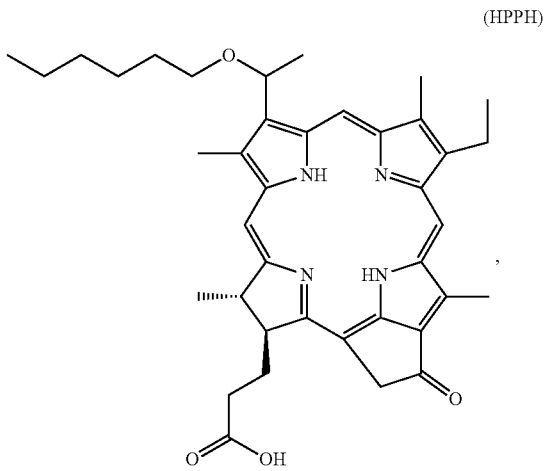 [SMILES: CCCCCCOC(C)c1c(C)c2cc3nc(c4c5[nH]c(cc6nc(cc1[nH]2)C(C)=C6CC)c(C)c5C(=O)C4)[C@@H](CCC(=O)O)[C@@H]3C]

(HPPH)

14. The composition of claim 1 comprising a mixture of different nanoparticles, at least one of which contains a posdtloaded photosensitizer and at least one of which contains a postloaded cyanine dye.

15. The composition of claim 14 wherein the photosensitizer is (HPPH)

a purpurinimide having an absorbance between 680 and 720 nm, bacteriopurpurinimide having an absorbance between 780 and 800 nm or mixtures thereof.

16. A composition according to claim 1 comprising polyacrylamide nanoparticles, containing a tetrapyrollic photosensitizer postloaded to the nanoparticles after nanoparticle formation and an imaging agent covalently bonded to the nanoparticles and a tumor targeting moiety covalently bonded to the nanoparticles.

17. The composition of claim 16 wherein the photosensitizer is a pyropheophorbide-a, a purpurinimide, or a bacteriopurpurinimde.

18. The composition of claim 16 wherein the imaging agent is a cyanine dye.

19. The composition of claim 16 wherein the imaging agent is a [124]I labeled compound.

20. The composition of claim 16 wherein the imaging agent is a PET, fluorescence or MR imaging agent.

21. The composition of claim 16 wherein the targeting moiety is selected from the group consisting of ROD and F3-Cys peptide.

22. The composition of claim 6 where the targeting moiety is a tumor targeting moiety selected from the group consisting of an RGD and F3-Cys peptide.

23. Polyacrylamide nanoparticles according to claim 1 wherein the photosensitizer is selected from the group consisting of pyropheophorbides, purpurinimides and bacteriopurpurinimides and tetrapyrollic derivatives thereof.

24. Nanoparticles according to claim 23 where the imaging agent is selected from the group consisting of a cyanine dye, an [124]I labeled compound, a PET, fluorescence and MR imaging agent.

25. Nanoparticles according to claim 24 where the nanoparticles further comprise a tumor-targeting moiety.

26. Nanoparticles according to claim 25 where the tumor targeting moiety is selected from the group consisting of peptides, folic acid, and carbohydrates.

27. Nanoparticles according to claim 26 where the tumor targeting many is selected from the group consisting of ROD and F3-Cys peptide.

28. Nanoparticles according to claim 23 where the polyacrylamide (PAA) nanoparticle is a polyacrylamide hydrogel.

* * * * *